United States Patent
Andersen

(10) Patent No.: US 10,736,950 B2
(45) Date of Patent: Aug. 11, 2020

(54) VACCINE COMPOSITIONS COMPRISING TRYPTOPHAN 2,3-DIOXYGENASE OR FRAGMENTS THEREOF

(71) Applicant: Herlev Hospital, Herlev (DK)

(72) Inventor: Mads Hald Andersen, Nærum (DK)

(73) Assignee: Herlev Hospital, Herlev (DK)

( * ) Notice: Subject to any disclaimer, the term of this patent is extended or adjusted under 35 U.S.C. 154(b) by 168 days.

(21) Appl. No.: 15/509,443

(22) PCT Filed: Sep. 15, 2015

(86) PCT No.: PCT/DK2015/050274
§ 371 (c)(1),
(2) Date: Mar. 7, 2017

(87) PCT Pub. No.: WO2016/041560
PCT Pub. Date: Mar. 24, 2016

(65) Prior Publication Data
US 2017/0239337 A1    Aug. 24, 2017

(30) Foreign Application Priority Data
Sep. 17, 2014    (DK) .................................. 2014 70571

(51) Int. Cl.
| | | |
|---|---|---|
| A61K 39/00 | (2006.01) | |
| A61K 39/39 | (2006.01) | |
| A61K 45/06 | (2006.01) | |
| C07K 14/725 | (2006.01) | |
| C07K 14/74 | (2006.01) | |
| C12N 9/02 | (2006.01) | |
| G01N 33/564 | (2006.01) | |

(52) U.S. Cl.
CPC .......... *A61K 39/0011* (2013.01); *A61K 39/39* (2013.01); *A61K 45/06* (2013.01); *C07K 14/7051* (2013.01); *C07K 14/70539* (2013.01); *C12N 9/0069* (2013.01); *C12Y 113/11011* (2013.01); *G01N 33/564* (2013.01); *A61K 2039/5154* (2013.01); *A61K 2039/53* (2013.01); *A61K 2039/545* (2013.01); *A61K 2039/55522* (2013.01); *A61K 2039/55527* (2013.01); *A61K 2039/55533* (2013.01); *A61K 2039/55566* (2013.01); *G01N 2333/90241* (2013.01)

(58) Field of Classification Search
None
See application file for complete search history.

(56) References Cited

U.S. PATENT DOCUMENTS

2011/0159017 A1* 6/2011 Van Den Eynde .. C12Q 1/6886
424/174.1

FOREIGN PATENT DOCUMENTS

EP    1 522 594    *  4/2005  .............. C12Q 1/68
WO    2009143843 A1    12/2009

OTHER PUBLICATIONS

Chauhan et al, Biochemistry, 47:4761-4769, 2008.*
Basran et al, Biochemistry, 47:4752-4760, 2008.*
Pantouris et al, Biochem Biophys Res Comm, 443:28-31, Jan. 2014.*
Iverson et al, Clin Cancer Res, 20:221-232, 2013.*
Cox and Coulter. Vaccine. Feb. 1997;15(3): 248-56.
Nicolette et al. Vaccine. Sep. 27, 2007;25 Suppl 2:B47-60. Epub Jun. 21, 2007.
Rammensee et al. Immunogenetics. Nov. 1999;50(3-4): 213-9.
Toebes et al. Nat Med. Feb. 2006;12(2): 246-51.
Morgan et al. Science. Oct. 6, 2006;314(5796):126-9.
Pilotte et al. Proc Natl Acad Sci U S A. Feb. 14, 2012;109(7): 2497-502.
Sorensen et al. PLoS One. Sep. 7, 2009;4(9): e6910.
Walter et al. N Engl J Med. Oct. 19, 1995;333(16):1038-44.
Zeeberg Iversen et al. Clin Cancer Res. Jan. 1, 2014;20(1): 221-32.
van der Burg, et al.; PNAS, 2007; vol. 104, No. 29; pp. 12087-12092.
Jandus, et al.; Cancer Research, 2009; vol. 69, No. 20; pp. 8085-8093.
Sharma, et al.; Immunity, 2010; vol. 33, No. 6; pp. 942-954.
Emmerich, et al.; Cancer Research, 2012; vol. 72, No. 14; pp. 3570-3581.
Cui, et al.; Immunity, 2011; vol. 35, No. 5; pp. 792-805.
Laidlaw, et al.; Nat. Immunol., 2015; vol. 16, No. 8; pp. 871-879.
Fourcade, et al.; J.. Immunol., 2010; vol. 184; pp. 6709-6718.
Bonertz, et al.; The Journal of Clinical Investigation, 2009; vol. 119, No. 11; pp. 3311-3321.

(Continued)

*Primary Examiner* — Mark Halvorson
(74) *Attorney, Agent, or Firm* — Dinsmore & Shohl LLP; Weston R. Gould

(57) ABSTRACT

The invention relates to prophylaxis and therapy of cancer. In particular there is provided a protein Tryptophan2,3-dioxygenase (TDO) or peptide fragments here of that are capable of eliciting anti-cancer immune responses. Specifically, the invention relates to the use of TDO or peptides derived thereof or TDO specific T-cells for treatment of cancer. The invention thus relates to an anti-cancer vaccine which optionally may be used in combination with other immunotherapies and to TDO specific T-cells adoptively transferred or induced in vivo by vaccination as a treatment of cancer. It is an aspect of the invention that the medicaments herein provided may be used in combination with cancer chemotherapy treatment. A further aspect relates to the prophylaxis and therapy of infections by the same means as described above.

13 Claims, 20 Drawing Sheets

Specification includes a Sequence Listing.

(56) References Cited

OTHER PUBLICATIONS

Lehe, et al.; Cancer Research, 2008; vol. 68, No. 15; pp. 6350-6359.
Geginat, et al.; Cytokine Growth Factor Reviews, 2016; pp. 1-7, http://dx.doi.org/10.1016/j.cytogfr.2016.02.003.
Hjortsø, et al.; OncoImmunology, 2015; vol. 4, Iss. 1; pp. 1-11, e968480.
Bijker, et al; The Journal of Immunology, 2007; vol. 179; pp. 5033-5040.

* cited by examiner

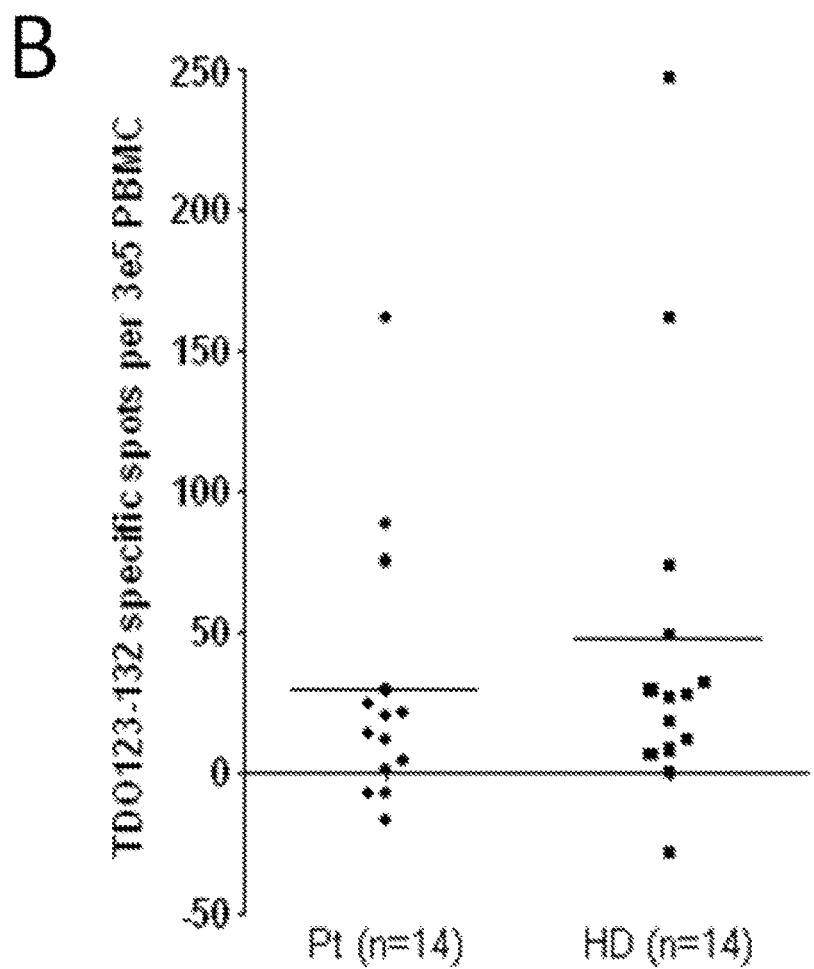
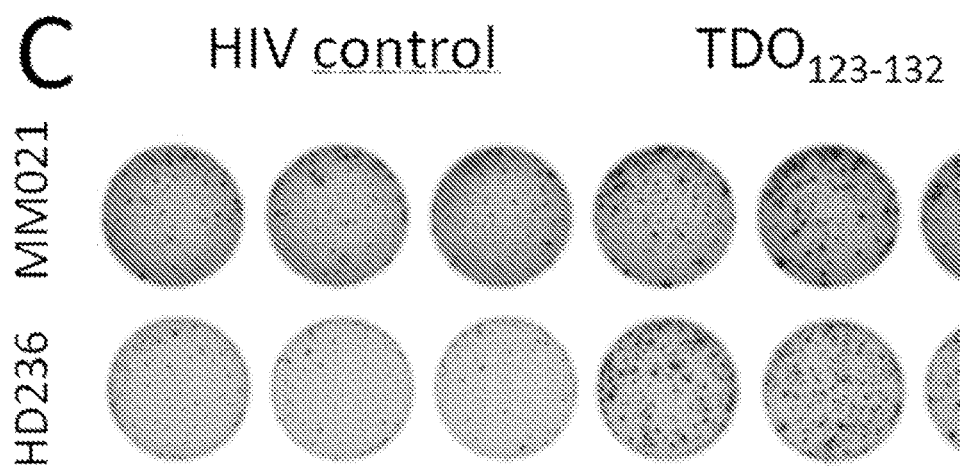
Fig. 1b-c

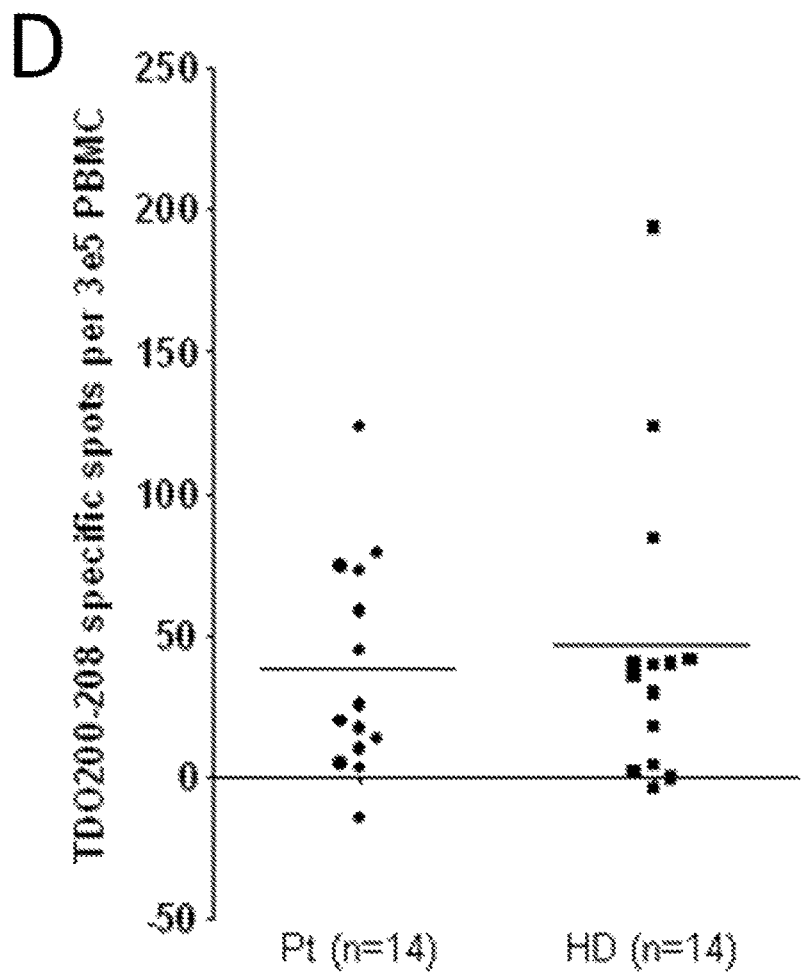
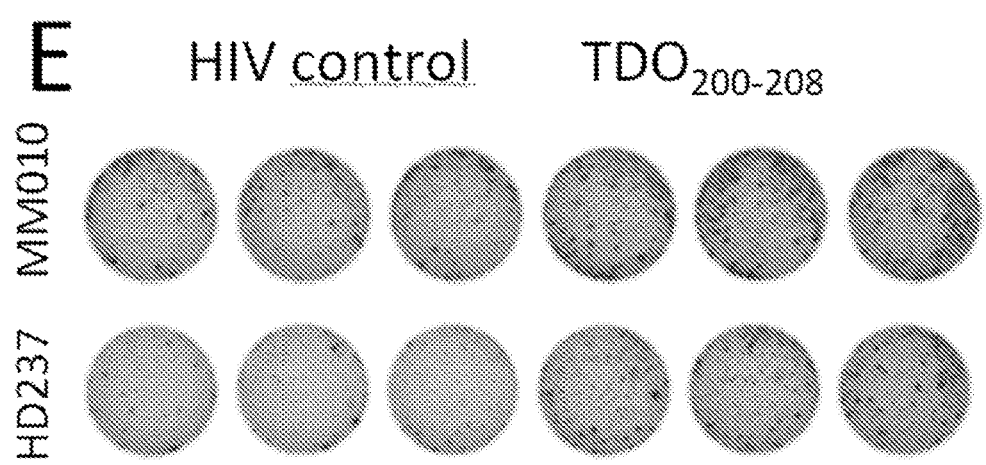
Fig. 1d-e

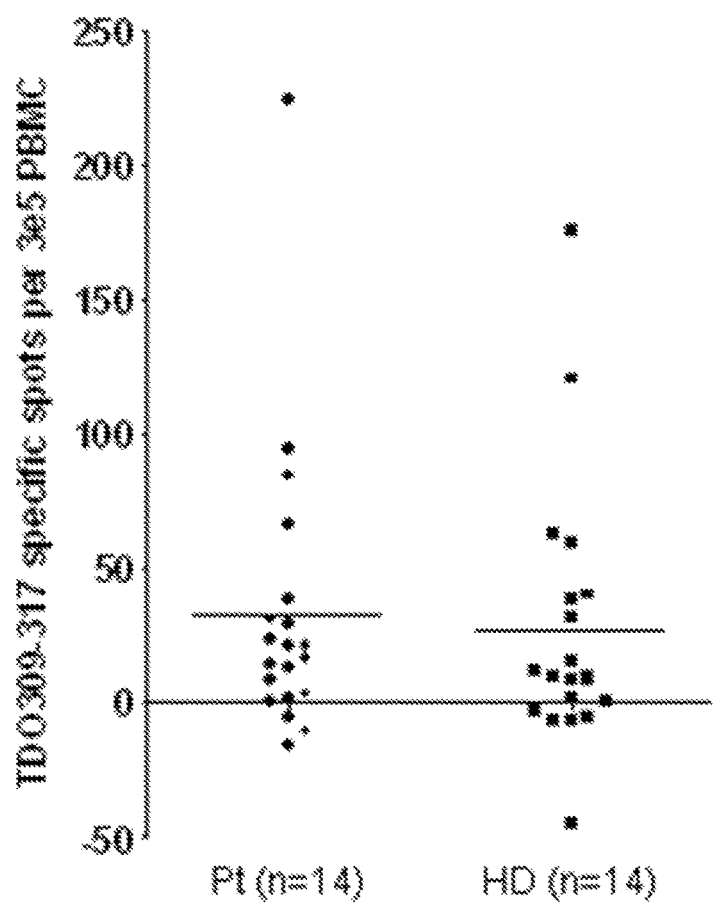
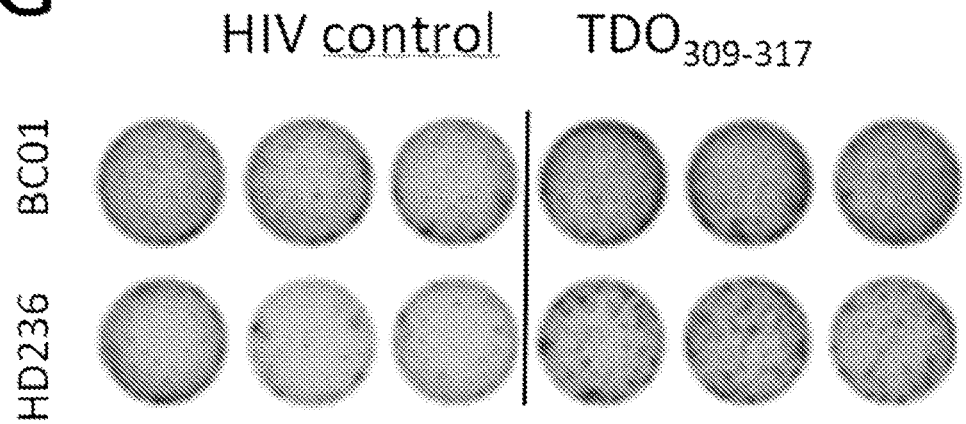
Fig. 1f-g

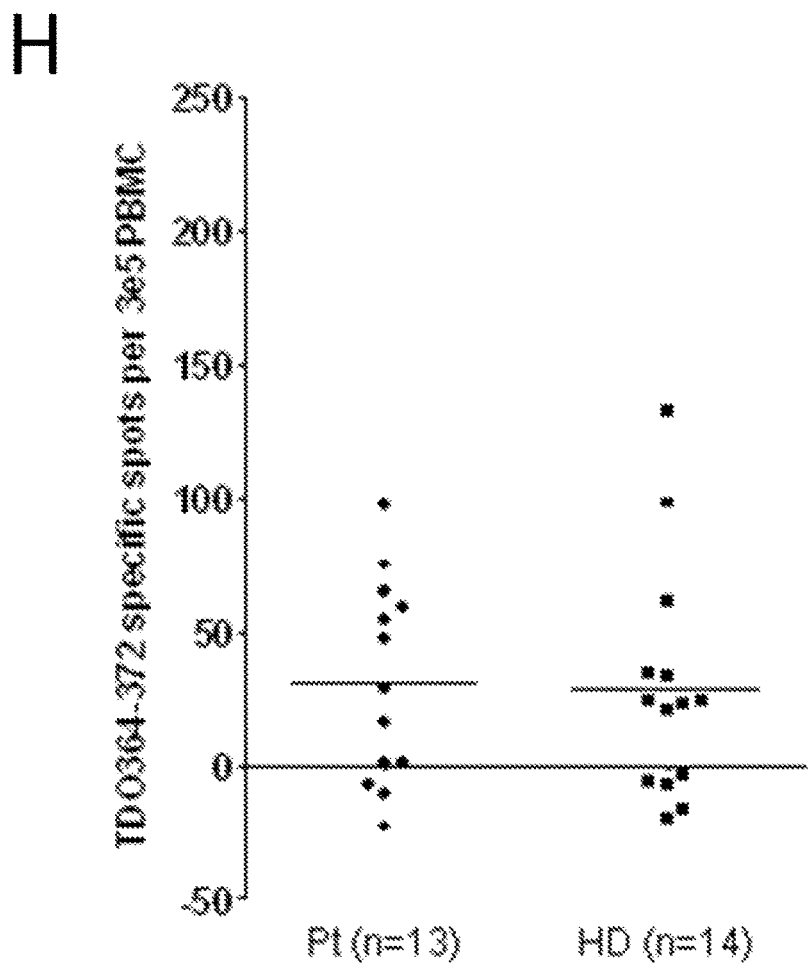
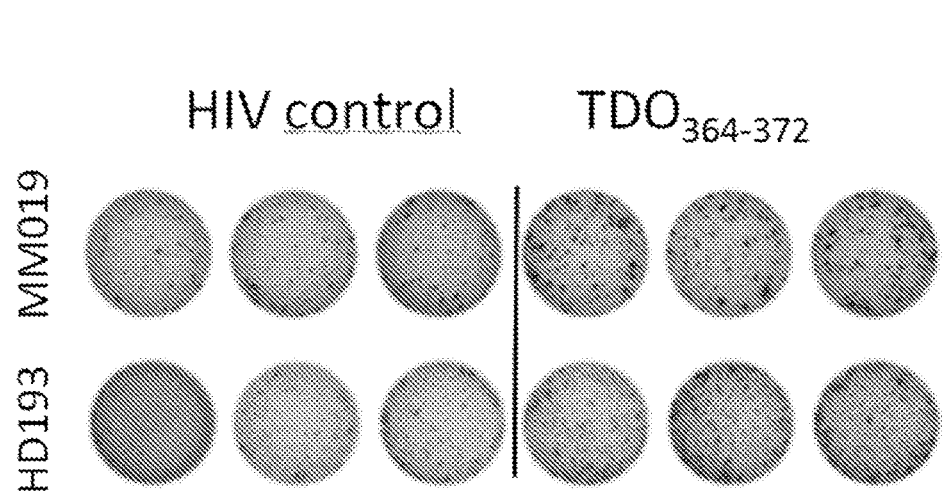
Fig. 1h-i

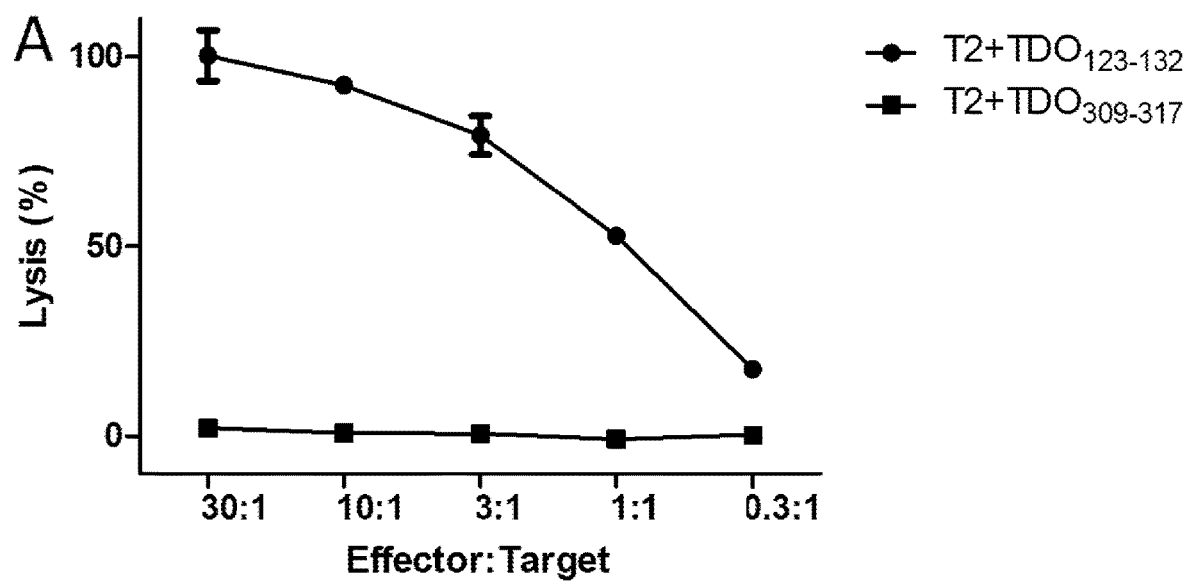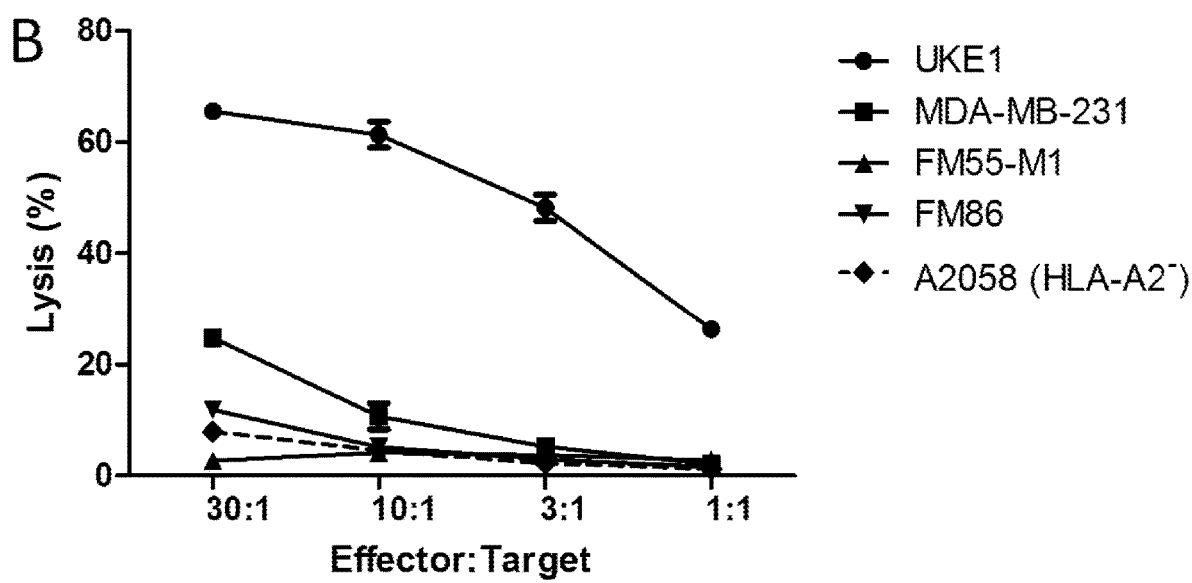
Fig. 3a-b

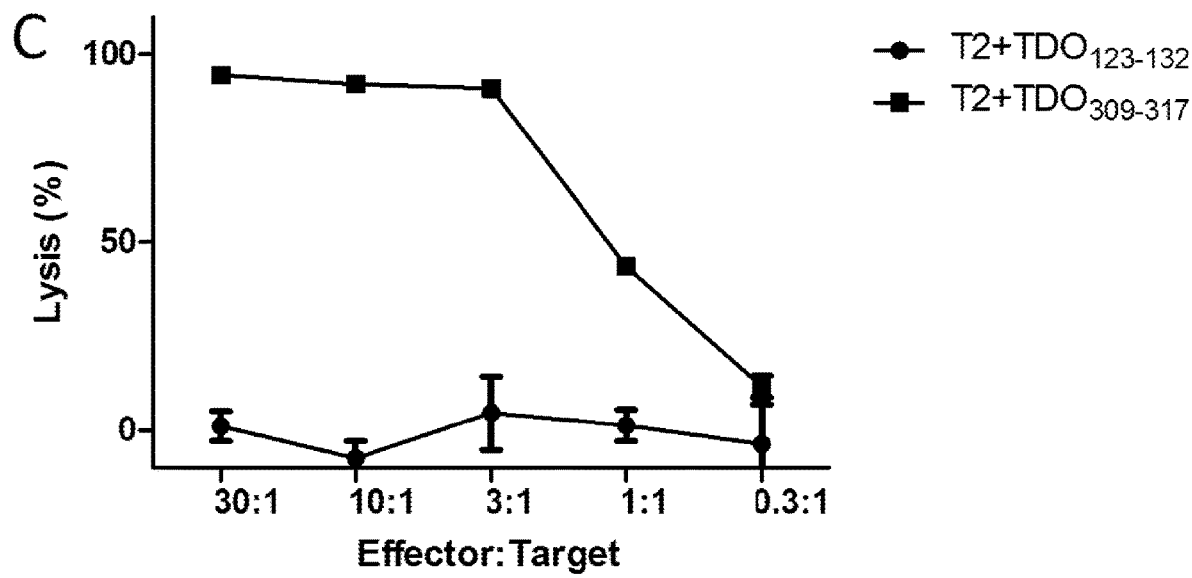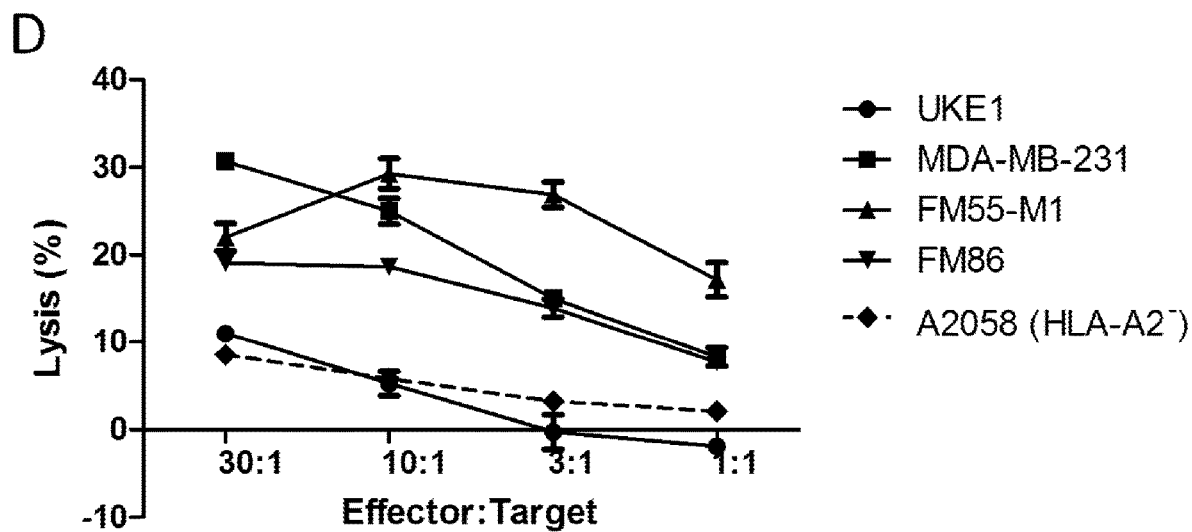
Fig. 3c-d

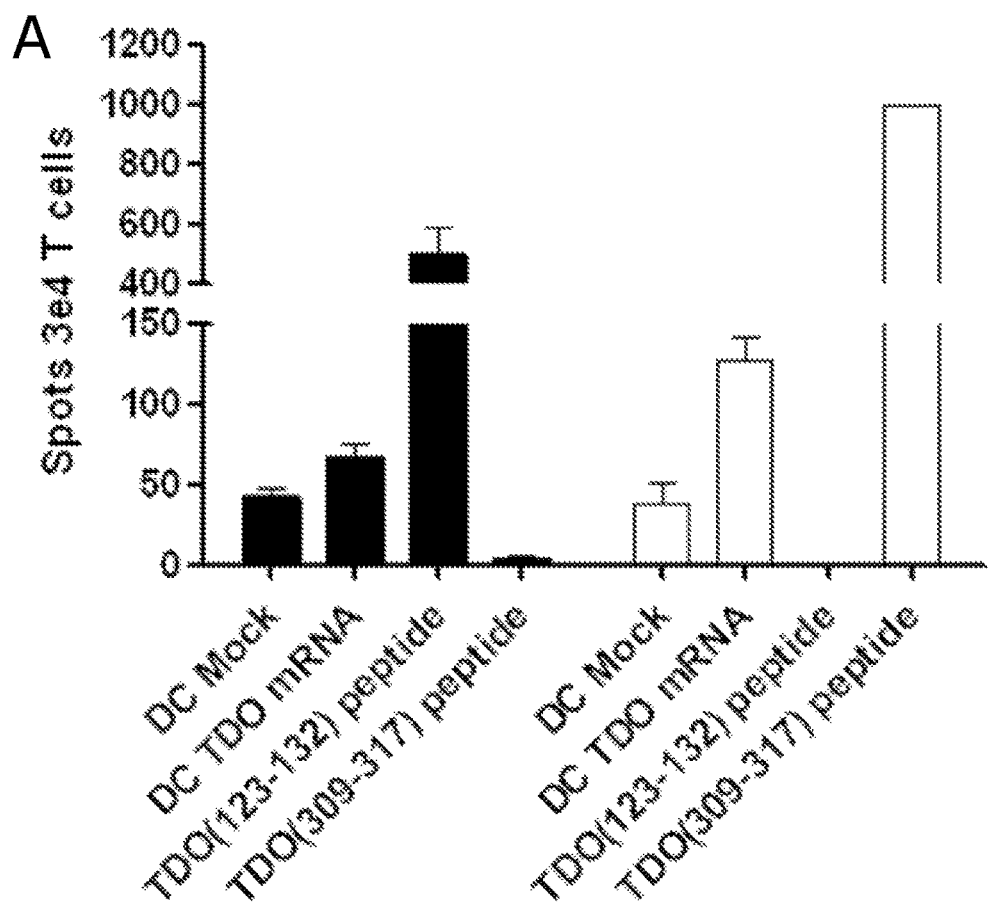
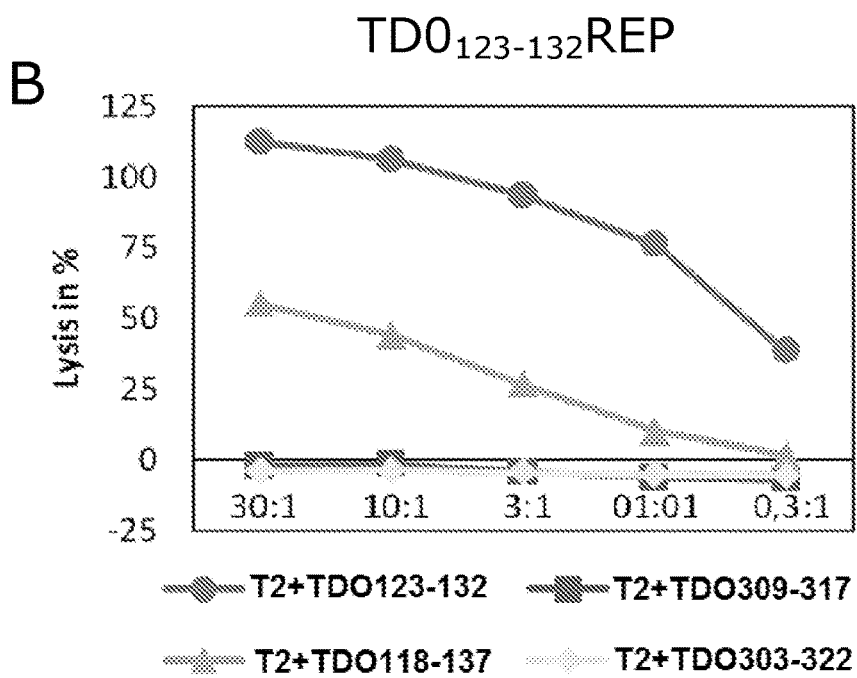
Fig. 4a-b

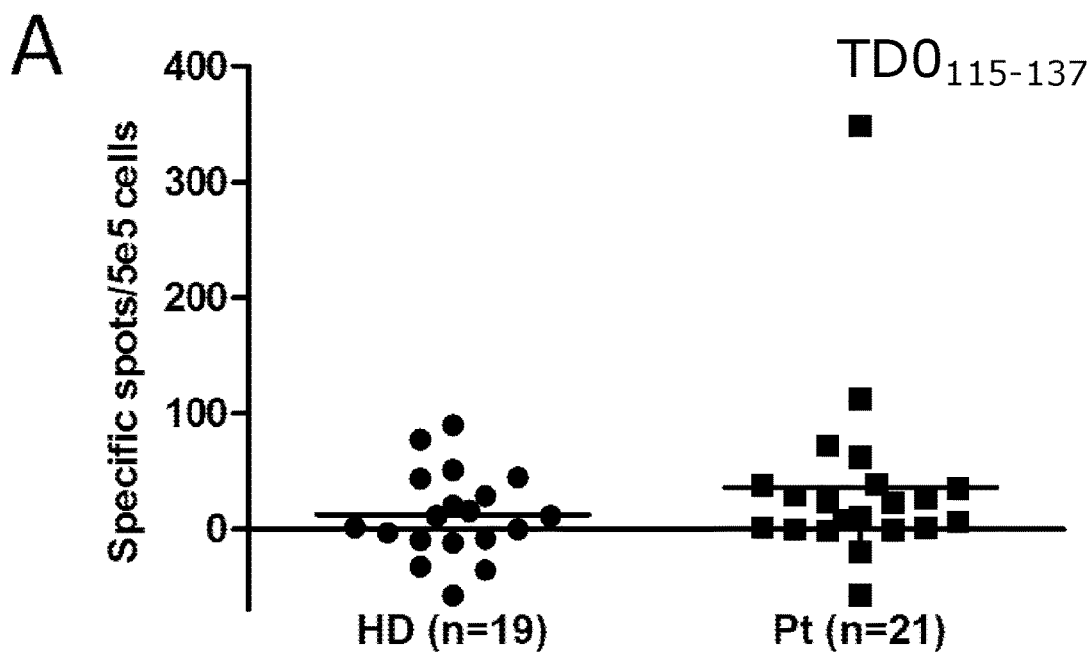
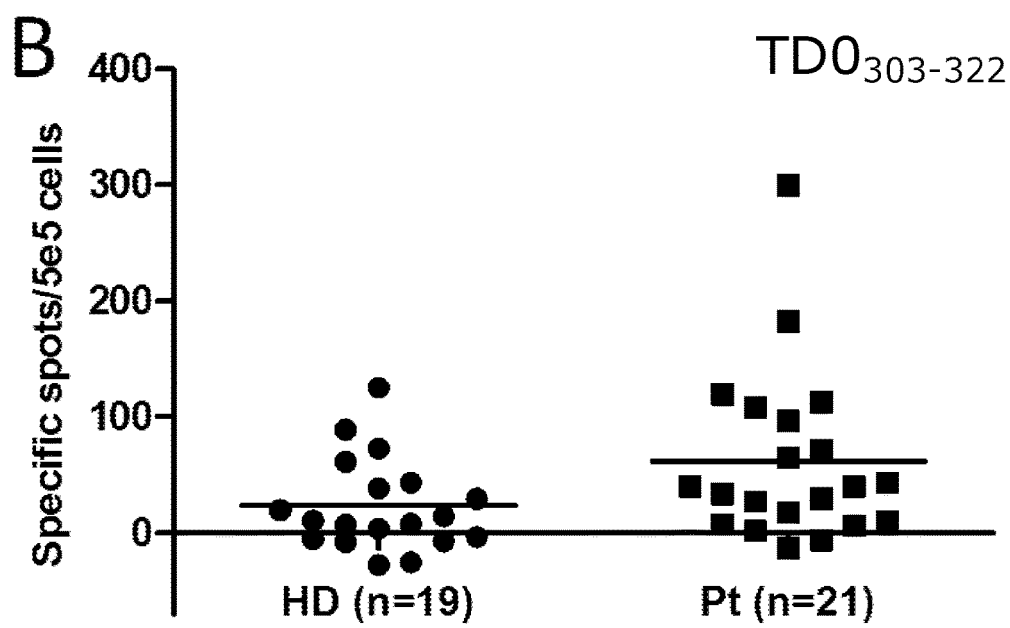
Fig. 5a-b IFNγ

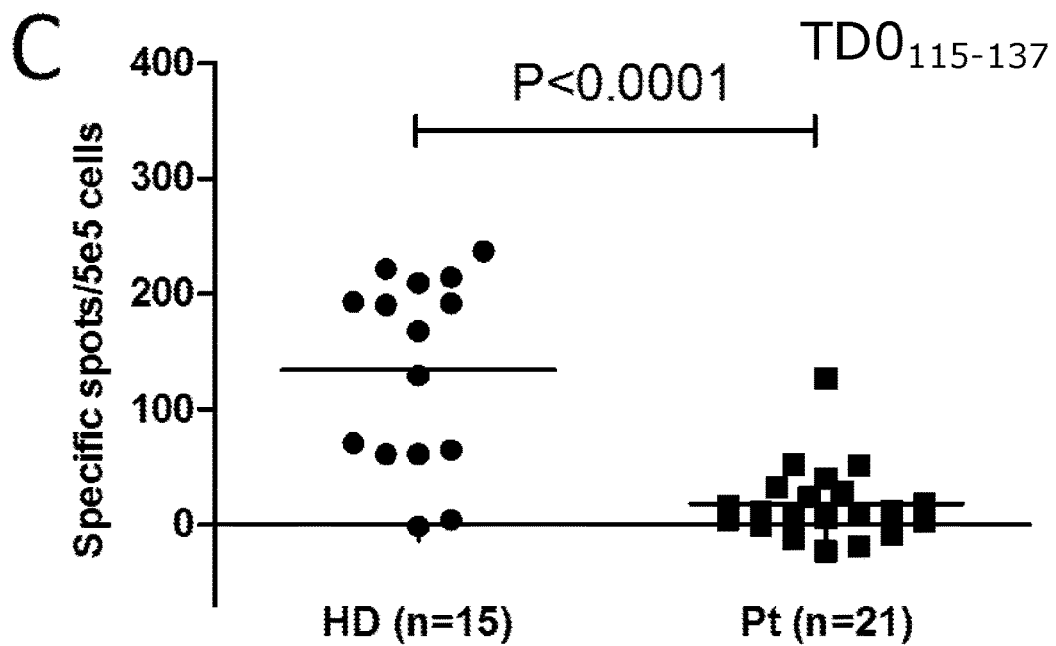
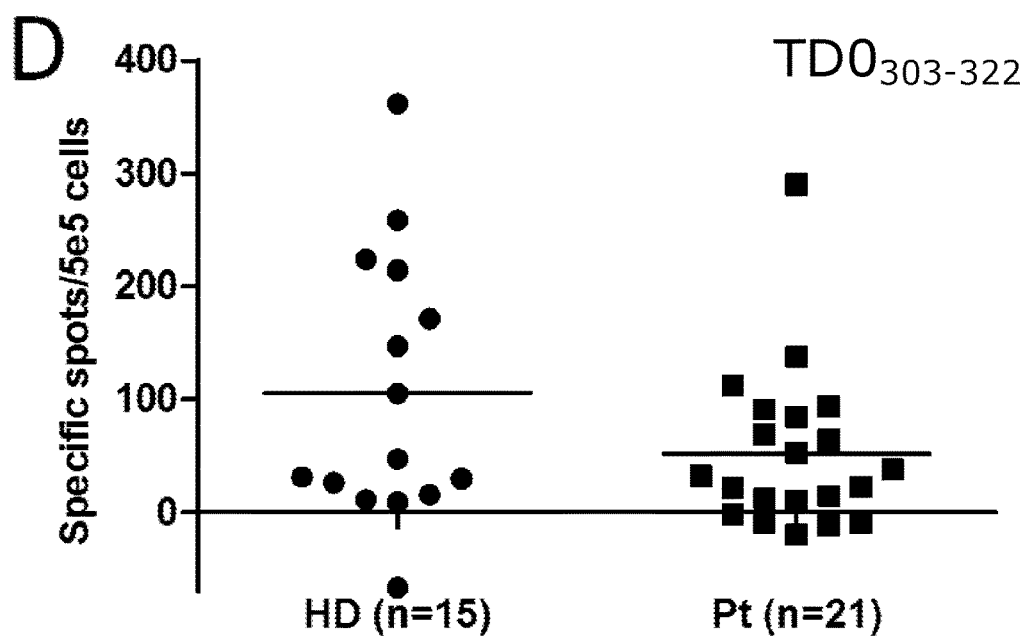
Fig. 5c-d TNFα

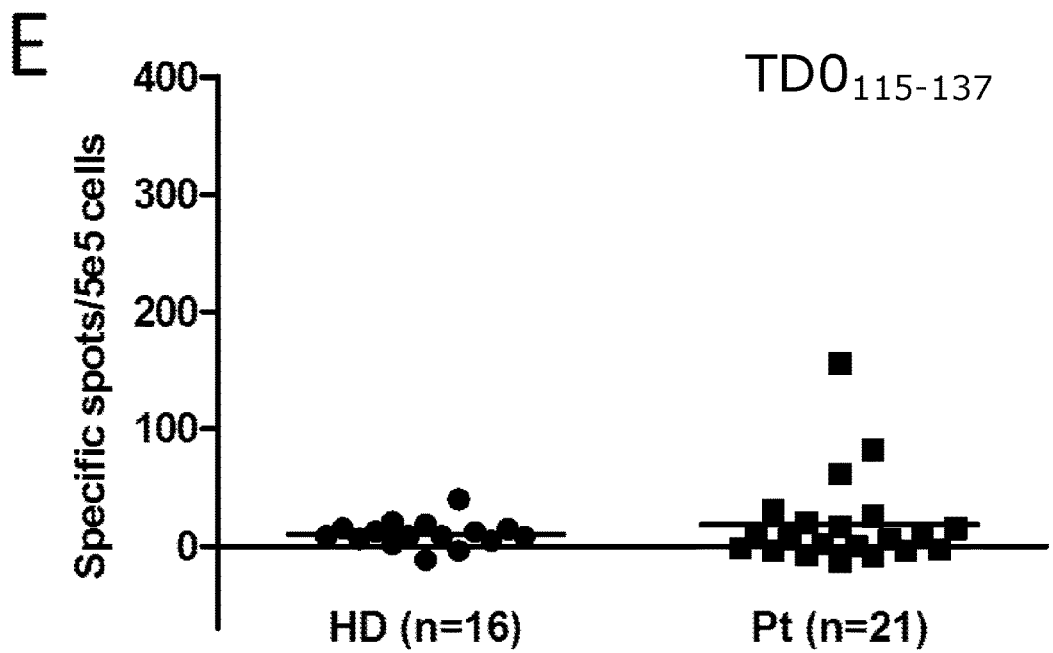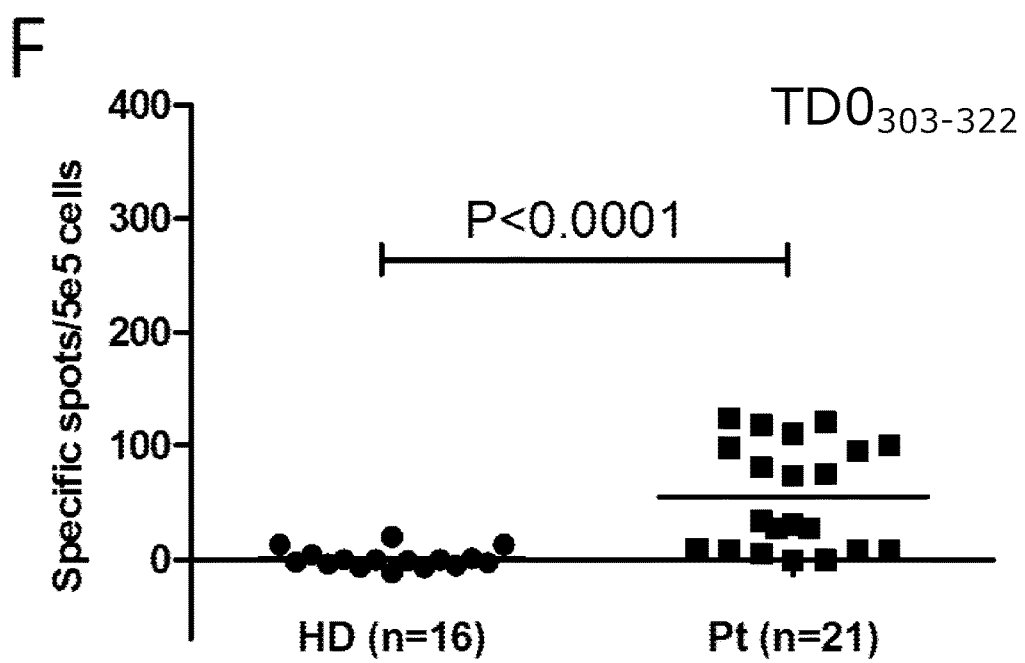
Fig. 5e-f IL-17

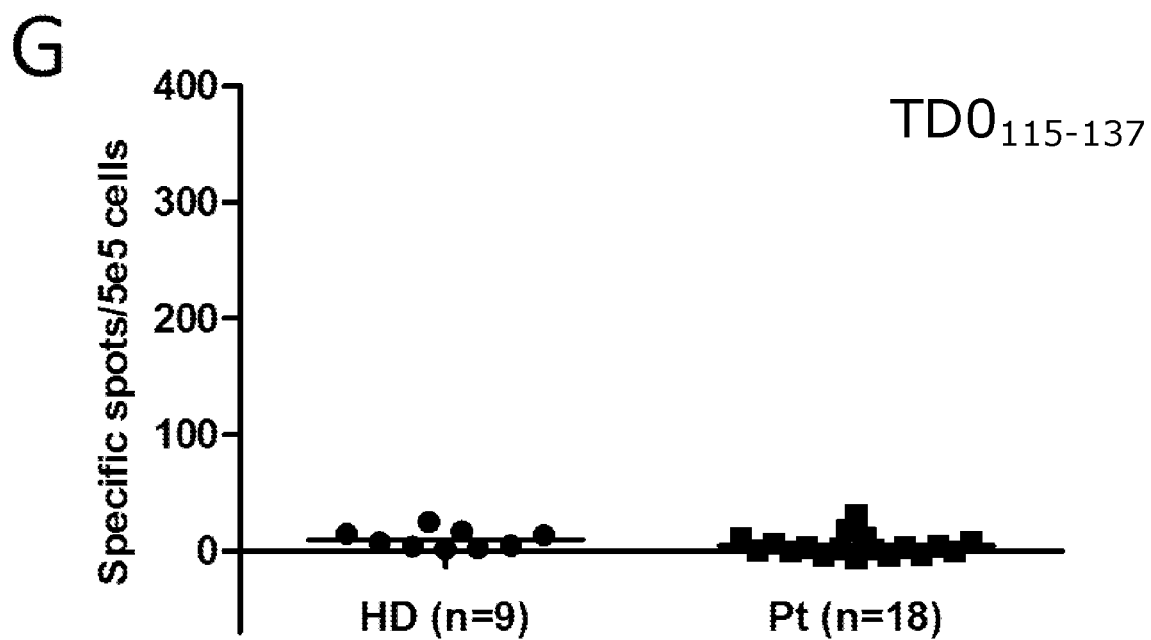
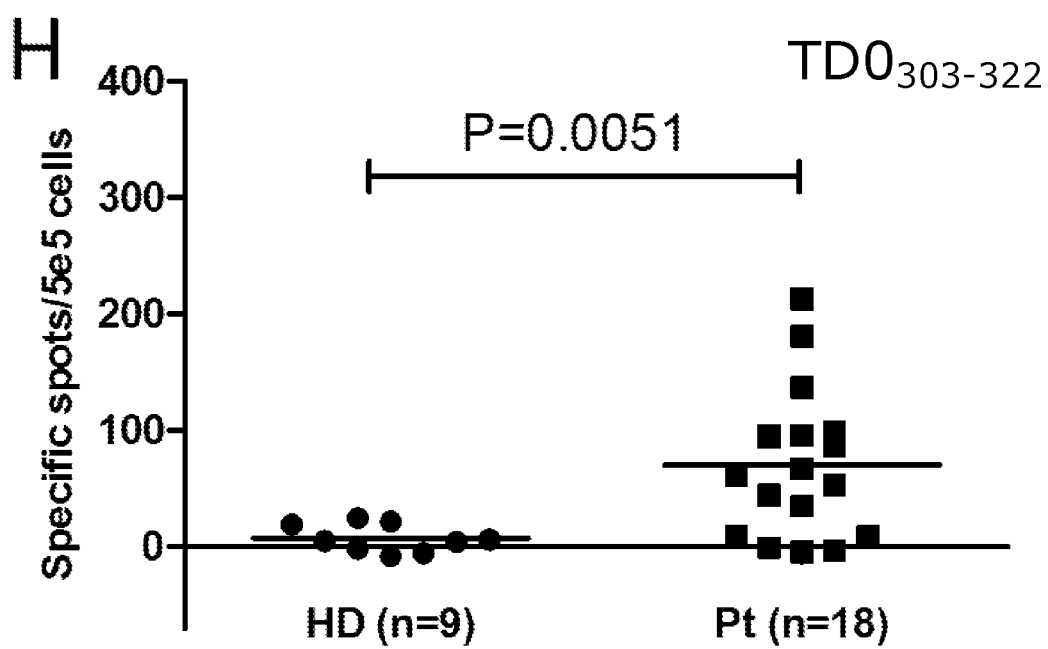
Fig. 5g-h IL-10

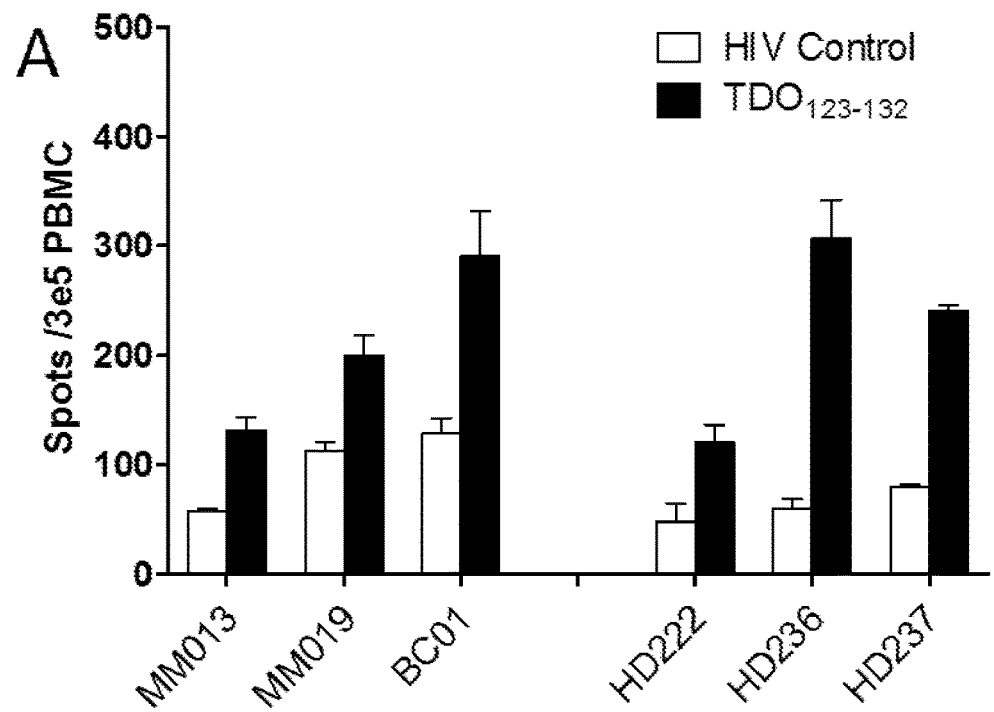
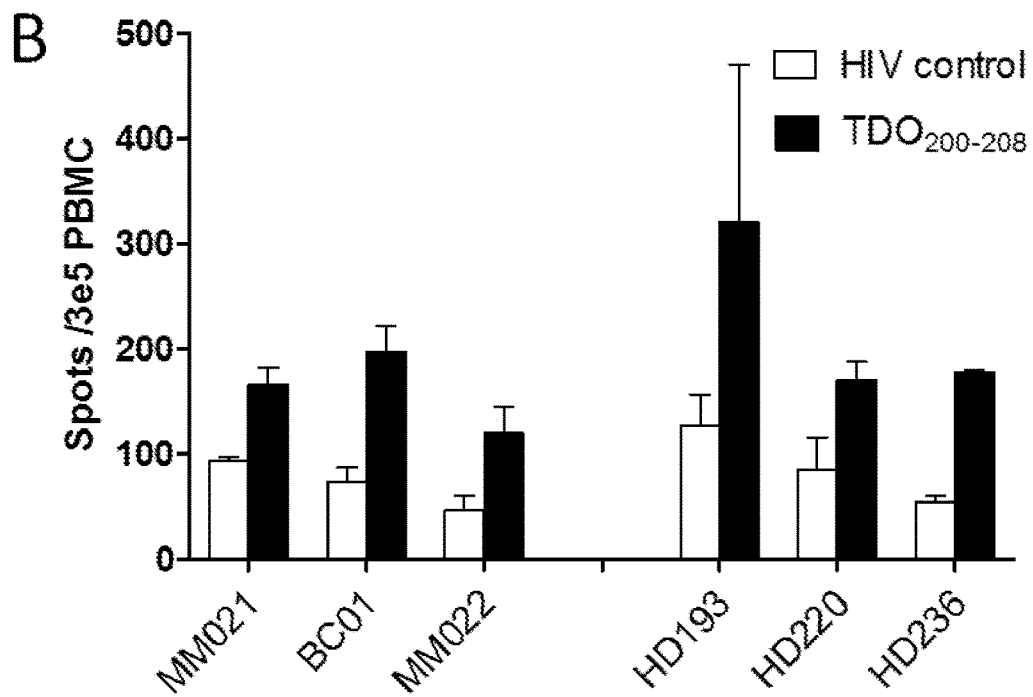
Fig. 7a-b

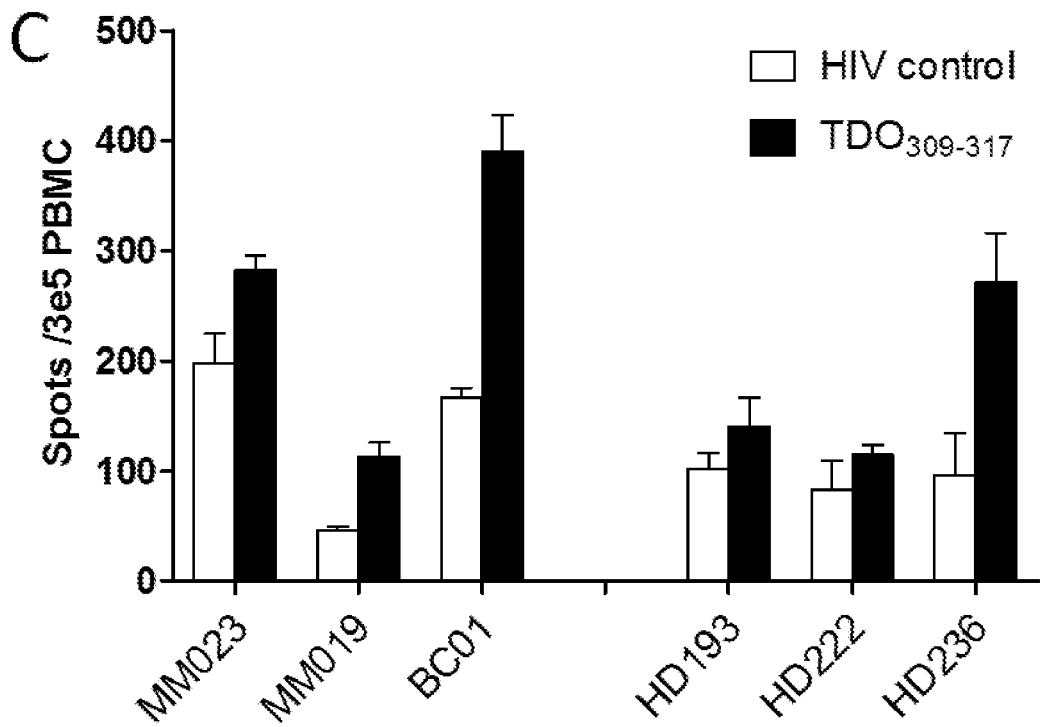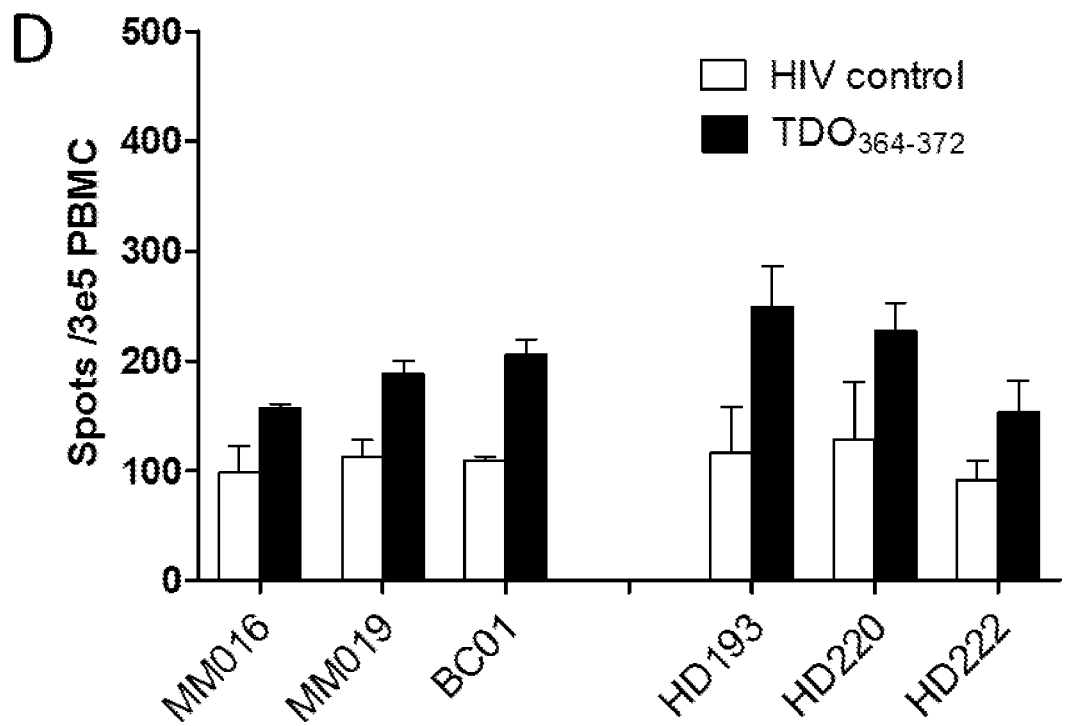
Fig. 7c-d

VACCINE COMPOSITIONS COMPRISING TRYPTOPHAN 2,3-DIOXYGENASE OR FRAGMENTS THEREOF

CROSS-REFERENCE TO RELATED APPLICATIONS

This application is the U.S. National Stage of International Application No. PCT/DK2015/050274, filed Sep. 15, 2015, which claims priority to Denmark Application No. PA 2014 70571, filed Sep. 17, 2014, both of which are hereby incorporated by reference in their entirety.

FIELD OF INVENTION

The present invention relates to the field of prophylaxis and therapy of cancer. In particular there is provided a protein Tryptophan 2,3-dioxygenase (TDO) or peptide fragments here of that are capable of eliciting anti-cancer immune responses. Specifically, the invention relates to the use of TDO or peptides derived thereof or TDO specific T-cells for treatment of cancer. The invention thus relates to an anti-cancer vaccine which optionally may be used in combination with other immunotherapies and to TDO specific T-cells adoptively transferred or induced in vivo by vaccination as a treatment of cancer. It is an aspect of the invention that the medicaments herein provided may be used in combination with cancer chemotherapy treatment. A further aspect relates to the prophylaxis and therapy of infections by the same means as described above.

The use of TDO and immunogenic peptide fragments hereof in cancer and infection treatment, diagnosis and prognosis is also provided.

BACKGROUND OF INVENTION

The immune system is tightly controlled to avoid the occurrence of autoimmunity when responding to various pathogens. This enantiostasis, allowing at the same time destruction of infected or transformed cells and self-tolerance, is guarded by several feedback mechanisms. Unfortunately, some of the mechanisms preventing auto-immunity are hijacked by cancers to attain immune escape. This evasion of immune destruction is based on several mechanisms including depletion of essential nutrients as well as accumulation of immunosuppressive metabolites. Thus, metabolic changes within the tumor microenvironment help to evade antigenic specific immune responses. In this respect, aberrations of the metabolism of the essential amino acid L-tryptophan have been described in various cancers. Notably, controlling the level of tryptophan is an important part of the host defense against invading pathogens as microbes need high concentrations of available tryptophan for optimal growth.

The degradation of L-(and D-) tryptophan to N-formylkynurenine is catalyzed by the heme dioxygenases tryptophan 2,3-dioxygenase (TDO) and indoleamine 2,3-dioxygenase (IDO). TDO and IDO do not share sequence homology. Although by distinct mechanisms, both TDO and IDO catalyze the first and rate-limiting step of tryptophan oxidation yielding kynurenine. Moreover, as IDO is upregulated by inflammatory cytokines such as type I and II interferon's, it is thought to be an important counter-regulatory enzyme, which controls disproportionate immune responses.

The impact of tryptophan metabolism on immune responses is well established. T cells sense low levels of tryptophan via the serine/threonine-protein kinase GCN2, which is then triggering proliferative arrest. Moreover, the tryptophan degradation product kynurenine binds the aryl hydrocarbon receptor (AHR); activation of AHR signaling induces formation of regulatory T cells.

Little is known about the function of TDO in cancer. Under physiologic conditions TDO is almost exclusively expressed at high amounts in the liver and—in lower levels—in the brain. Recently, it was described that tumors of different origin express TDO, especially melanoma, bladder cancer, hepatocellular carcinoma and glioblastoma (Pilotte et al., 2012). In a series of 104 human tumor cell lines of various histological types, 20 tumors expressed only TDO, 17 only IDO and 16 both enzymes (Pilotte et al., 2012). Moreover, in a preclinical model, TDO expression by tumors prevented their rejection by immunized mice (Pilotte et al., 2012).

SUMMARY OF INVENTION

The expression of TDO and the potential TDO induced cancer immunosuppression poses a problem in the treatment of cancer.

The problem of cancer immunosuppression is solved by the present invention, which provides TDO as a novel T cell target. Instead of inhibiting the function of TDO, the present invention provides peptides and compositions capable of activating TDO-specific T-cells, which recognizes cells expressing TDO.

Thus, the present invention provides materials and methods for treatment of cancer diseases by targeting TDO expressing cancer cells directly and by killing TDO expressing cancer cells. This is done by enabling T cells to recognize the TDO expressing cells. Interestingly, the present invention discloses that cytotoxic immune responses against TDO expressing cells can be raised even though TDO expressing cells may antagonize the desired effects of other immunotherapeutic approaches.

Likewise, the invention provides materials and methods for treatment of other diseases, which normally may invoke an immune response, e.g. infections. In the methods of the invention T cells are enabled to kill TDO expressing APCs/DCs.

Thus, the invention exploits expression of the immune suppressing enzyme TDO in cancer cells and targets these TDO expressing cells.

Interestingly, the present invention demonstrates that T cells specifically recognizing TDO can be found in healthy individuals (see Example 1 below). This indicates a loss of tolerance to the self-protein TDO. The invention takes advantage of this loss of tolerance to TDO, and it is thus an aspect of the invention to provide vaccine compositions which surprisingly can generate an immune response against the self-protein TDO.

The present invention provides vaccine compositions comprising
  a) one or more of the following:
    (i) tryptophan 2,3-dioxygenase (TDO) of SEQ ID NO:1;
    (ii) an immunogenically active peptide fragment of TDO comprising a consecutive sequence of amino acids of TDO of SEQ ID NO:1;
    (iii) an immunogenically active peptide fragments of TDO, which is an MHC Class I-restricted peptide fragment or MHC Class II-restricted peptide fragment;

(iv) a functional homologue of the polypeptides under (i), (ii) and (iii), wherein said functional homologue shares at least 70% sequence identity with SEQ ID NO:1 and/or said functional homologue is an immunogenically active polypeptide consisting of a sequence identical to a consecutive sequence of amino acids of SEQ ID NO:1, except that at the most three amino acids have been substituted;

(v) a polypeptide comprising any of the polypeptides under (i), (ii), (iii) or (iv);

(vi) a nucleic acid encoding any of the polypeptides under 1), 2), 3) and 4); and b) an adjuvant.

The vaccine compositions may be used as a medicament, and may for example be for treatment of a cancer disease where TDO is expressed or for treatment of an infection causing TDO expression in APCs.

The invention also provides kit-of-parts comprising the vaccine composition and a second active ingredient.

The invention also provides compositions for ex vivo or in situ diagnosis of the presence in an individual suffering from a clinical condition of T cells in PBL or in tumor tissue that is reactive with TDO, the composition comprising a peptide fragment of TDO, e.g. any of the peptide fragments of TDO described herein below in the sections "Immunogenically active peptide fragment of TDO", "Polypeptide comprising TDO or a fragment thereof" and "MHC".

The invention further provides diagnostic kits for ex vivo or in situ diagnosis of the presence in an individual suffering from a clinical condition of T cells in PBL or in tumor tissue that is reactive with TDO, the kit comprising a peptide fragment of TDO, e.g. any of the peptide fragments of TDO described herein below in the sections "Immuno-genically active peptide fragment of TDO", "Polypeptide comprising TDO or a fragment thereof" and "MHC".

The invention also describes complexes of a peptide fragment of TDO and a Class I HLA or a Class II HLA molecule or a fragment of such molecule. Said peptide fragment may e.g. be any of the peptide fragments of TDO described herein below in the sections "Immunogenically active peptide fragment of TDO", "Polypeptide comprising TDO or a fragment thereof" and "MHC".

The invention further discloses methods of detecting in an individual suffering from a clinical condition the presence of TDO reactive T-cells, the method comprising contacting a tumor tissue or a blood sample with the complex comprising peptide fragments of TDO described above and detecting binding of the complex to the tissue or the blood cells.

The invention also discloses molecules that are capable of binding specifically to a peptide fragment of TDO e.g. be any of the peptide fragments of TDO described herein below in the sections "Immunogenically active peptide fragment of TDO", "Polypeptide comprising TDO or a fragment thereof" and "MHC".

The invention also provides methods of treating a clinical condition characterized by the expression of TDO, the method comprising administering to an individual suffering from said clinical condition an effective amount of the vaccine compositions of the invention, of a kit-of-parts of the invention, of a composition of the invention and/or of an immunogenically active peptide fragment of TDO, e.g. be any of the peptide fragments of TDO described herein below in the sections "Immunogenically active peptide fragment of TDO", "Polypeptide comprising TDO or a fragment thereof" and "MHC".

The invention also provides use of the vaccine compositions of the invention in the manufacture of a medicament for the treatment or prevention of a clinical condition, e.g. cancer and/or inflammations.

The invention also provides methods of monitoring immunization, said method comprising the steps of c) providing a blood sample from an individual d) providing TDO of SEQ ID NO:1 or a functional homologue thereof having at least 70% identity thereto or an immunogenically active peptide fragment comprising a consecutive sequence of said TDO or said functional homologue thereof or a nucleic acid encoding said TDO or said peptide fragment.

e) determining whether said blood sample comprises antibodies or T-cells comprising T-cell receptors specifically binding the protein or peptide f) thereby determining whether an immune response to said protein or peptide has been raised in said individual.

Further, the invention provides immunogenically active TDO peptide fragments comprising a consecutive sequence of TDO of SEQ ID NO:1 or a functional homologue thereof, said functional homologue being a polypeptide of identical sequence except that at the most three amino acids have been substituted, or a nucleic acid encoding said TDO peptide fragment for use in the treatment or prevention of clinical conditions associated with expression of TDO, such as cancer and/or infections.

DESCRIPTION OF DRAWINGS

FIG. 3 shows cytolytic capacity of TDO-specific T cells. (A), The lysis of T2-cells pulsed with either relevant $TDO_{123-132}$ peptide (dots) or an irrelevant TDO peptide $TDO_{309-317}$ (squares) by the $TDO_{123-132}$-specific T-cell culture as examined by $^{51}$Cr-release assay. X-axis designate effector:target ratio. (B), Lysis by $TDO_{123-132}$-specific T cells of the HLA-A2$^+$ melanoma cell lines FM-55M1 and FM-86, the breast cancer cell line MDA-MB 231, and the AML cell line UKE-1 at different effector to target ratios as assayed by $^{51}$Cr-release. In addition the Melanoma cell line A2058 (HLA-A2 negative) was examined as negative control. (C) The lysis of T2-cells pulsed with either relevant $TDO_{309-317}$ peptide (squares) or an irrelevant TDO peptide $TDO_{123-132}$ (dots) by the $TDO_{309-317}$-specific T-cell culture as examined by $^{51}$Cr-release assay. (D), Lysis by $TDO_{309-317}$-specific T cells of the HLA-A2$^+$ melanoma cell lines FM-55M1 and FM-86, the breast cancer cell line MDA-MB 231, and the AML cell line UKE-1 at different effector to target ratios as assayed by $^{51}$Cr-release. In addition the Melanoma cell line A2058 (HLA-A2 negative) was examined as negative control.

FIG. 4 shows A ELISPOT responses against autologous dendritic cells transfected with TDO mRNA or Mock as well as control wells with addition of only peptides $TDO_{123-132}$ or $TDO_{309-317}$. B cytotoxicity of the $TDO_{123-132}$ specific IL2 expanded T cell cultures against T2 cells loaded with $TDO_{123-132}$, $TDO_{309-317}$ or the corresponding long peptides $TDO_{118-137}$ and $TDO_{303-322}$, respectively. Short peptides were added immediately before the assay and longer peptides were added the night before. X-axis denote Effector: target ratio.

FIG. 5 shows natural CD4$^+$ T-cell responses against TDO in healthy and cancer patients. T-cell responses against $TDO_{118-137}$ (A, C, E, G), or $TDO_{303-322}$ (B, D, F, H) were measured by IFNγ (A, B), TNFα (C, D), IL-17 (E, F) or IL-10 (G, H) ELISPOT. The average number of TDO-specific cells from triplicate experiments (after subtraction of background) was calculated per $5\times10^5$ PBMC for each patient. PBMC from 19 healthy individuals (HD), 21 cancer patients (Pt) (twenty patients with MM and one BC) were analyzed. Only p-values (p<0,05) by a Mann-Whitney test are revealed.

FIG. 7 shows examples of statistically significant TDO responses shown by ELISPOT. The non-parametric distribution free resampling (DFR) method allowed statistical comparison of antigen-stimulated wells and negative control. The bars represent mean spot count in wells with control peptide ($HIVpol_{468-476}$) (white) or a TDO-derived peptide (black) for (A) $TDO_{123-132}$, (B) $TDO_{200-208}$, (C) $TDO_{309-317}$, (D) $TDO_{364-372}$ (black). Error bars represent standard deviation. The cell numbers were $3*10^5$ cells/well.

DETAILED DESCRIPTION OF THE INVENTION

Figure 1A:
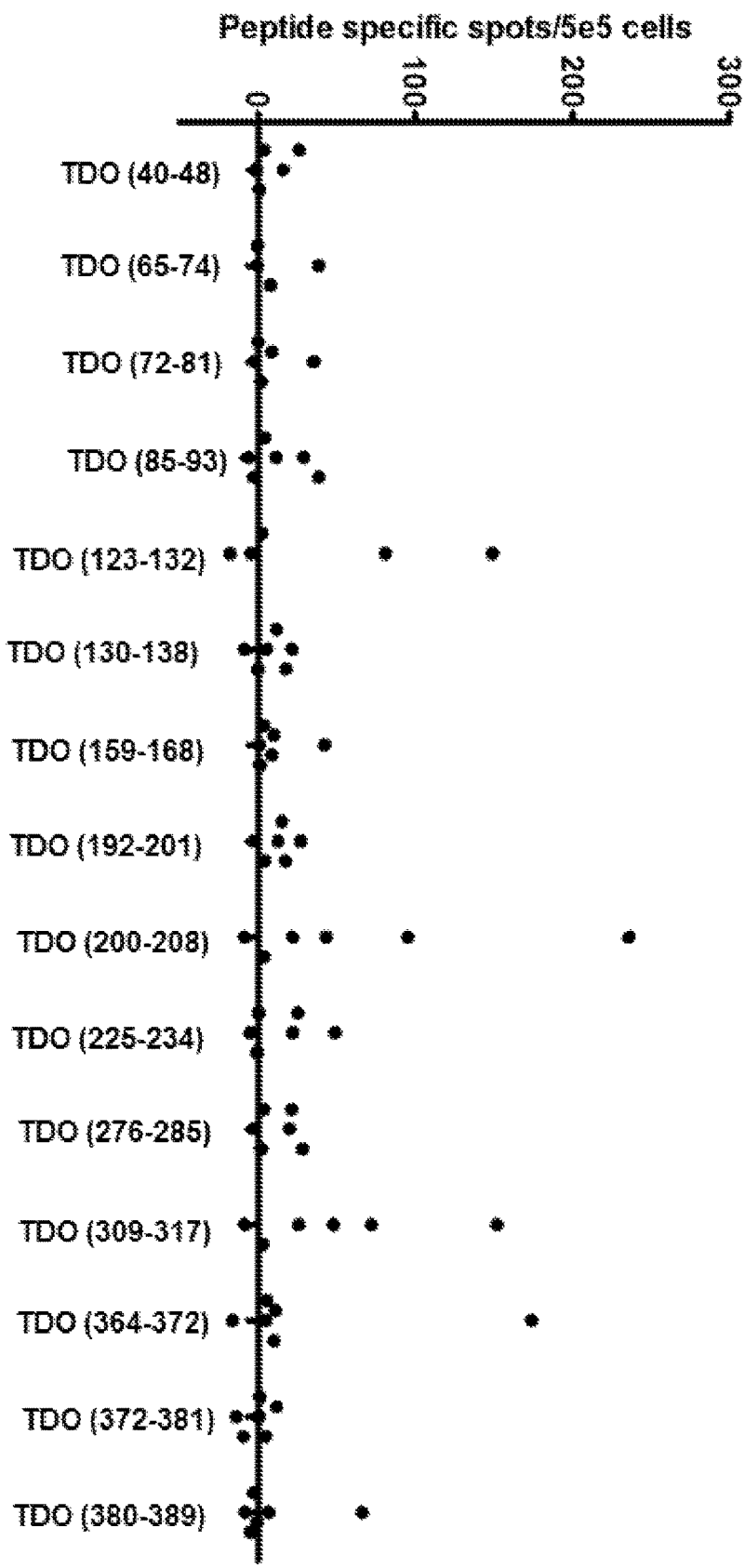
FIG. 1 shows natural T-cell responses against TDO. (A), In order to detect TDO-specific CD8$^+$ T-cell responses, 15 predicted HLA-A2 restricted T-cell epitopes were synthesized to examine peripheral blood mononuclear cells (PBMC) from six, HLA-A2$^+$ cancer patients. PBMC samples were stimulated once in vitro with peptide and IL-2 for one week before being plated in an IFNγ ELISPOT assay at 5×10$^5$ cells per well in triplicates with or without a relevant TDO peptide. The average number of TDO-specific, IFNγ-releasing cells was calculated per 5×10$^5$ PBMC. IFNγ ELISPOT responses against $TDO_{123-132}$ (KLLVQQF-SIL) were examined in 14 cancer patients and 14 healthy donors. T cells were stimulated once with peptide before being plated in an IFNγ ELISPOT assay at 3×10$^5$ cells per well in triplicates with the $TDO_{123-132}$ (B), $TDO_{200-208}$ (D), $TDO_{309-317}$ (F), $TDO_{364-372}$ (H), or a negative control peptide ($HIV_{pol476-484}$ (ILKEPVHGV)). The dot plots designate mean spot count of triplicate positive wells with subtraction of background. Examples of ELISPOT experiments against $TDO_{123-132}$ (C), $TDO_{200-208}$ (E), $TDO_{309-317}$ (G), $TDO_{364-372}$ (I), and $HIV_{pol476-484}$ in PBMC from different cancer patients or healthy donors.

It is a major objective of the present invention to provide a vaccine composition comprising Tryptophan 2,3-dioxygenase (TDO) or an immunologically active polypeptide fragment hereof, polyppetides comprising same or nucleic acids encoding same for use as a medicament in the prevention of, reduction of risk of, or treatment of any proliferative disorder, such as cancer.

Definitions

Adjuvant: Any substance whose admixture with an administered immunogenic determinant/antigen/nucleic acid construct increases or otherwise modifies the immune response to said determinant.

Antigen: Any substance that can bind to a clonally distributed immune receptor (T-cell or B-cell receptor). Usually a peptide, polypeptide or a multimeric polypeptide. Antigens are preferably capable of eliciting an immune response.

APC: Antigen-presenting cell. An APC is a cell that displays foreign antigen complexed with MHC on its surface. T-cells may recognize this complex using their T-cell receptor (TCR). APCs fall into two categories: professional, (of which there are three types: Dendritic cells, macrophages and B-cells) or non-professional (does not constitutively express the Major histocompatibility complex proteins required for interaction with naive T cells; these are expressed only upon stimulation of the non-professional APC by certain cytokines such as IFN-γ).

Boost: To boost by a booster shot or dose is to administer an additional dose of an immunizing agent, such as a vaccine, administered at a time after the initial dose to sustain the immune response elicited by the previous dose of the same agent.

Carrier: Entity or compound to which antigens are coupled to aid in the induction of an immune response.

Chimeric protein: A genetically engineered protein that is encoded by a nucleotide sequence made by a splicing together of two or more complete or partial genes or a series of (non)random nucleic acids.

Clinical condition: A condition that requires medical attention, herein especially conditions associated with the expression of TDO. Examples of such conditions include: proliferative disorders, such as cancers and infections.

Complement: A complex series of blood proteins whose action "complements" the work of antibodies. Complement destroys bacteria, produces inflammation, and regulates immune reactions.

CTL: Cytotoxic T lymphocyte. A sub group of T-cells expressing CD8 along with the T-cell receptor and therefore able to respond to antigens presented by class I molecules.

Delivery vehicle: An entity whereby a nucleotide sequence or polypeptide or both can be transported from at least one media to another.

DC: Dendritic cell. (DCs) are immune cells and form part of the mammalian immune system. Their main function is to process antigen material and present it on the surface to other cells of the immune system, thus functioning as antigen-presenting cells (APCs).

Fragment: is used to indicate a non-full length part of a nucleic acid or polypeptide. Thus, a fragment is itself also a nucleic acid or polypeptide, respectively.

Functional homologue: A functional homologue may be any polypeptide that exhibits at least some sequence identity with a wild type version of a polypeptide and has retained at least one aspect of the original functionality. Herein a functional homologue of TDO is a polypeptide sharing at least some sequence identity with TDO and which has the capability to induce an immune response to cells expressing TDO. A functional homologue of an immunogenically active peptide fragment of TDO is a peptide sharing at least some sequence identity with a peptide fragment of TDO and which has the capability to induce an immune response to cells expressing TDO.

Immunogenically active peptide: Peptide capable of eliciting an immune response in at least one individual after administration to said individual.

Individual: Generally any species or subspecies of bird, mammal, fish, amphibian, or reptile, preferably a mammal, most preferably a human being.

Infection: Herein the term "infection" relates to any kind of clinical condition involving an invasion of the host organism by disease-causing agents. In particular, infection refers to a clinical condition involving invasion of an individual by a pathogen.

Isolated: used in connection with nucleic acids, polypeptides, and antibodies disclosed herein 'isolated' refers to these having been identified and separated and/or recovered from a component of their natural, typically cellular, environment. Nucleic acids, polypeptides, and antibodies of the invention are preferably isolated, and vaccines and other compositions of the invention preferably comprise isolated nucleic acids, polypeptides or isolated antibodies.

MHC: Major histocompatibility complex, two main subclasses of MHC, Class I and Class II exist.

Nucleic acid: A chain or sequence of nucleotides that convey genetic information. In regards to the present invention the nucleic acid is generally a deoxyribonucleic acid (DNA).

Nucleic acid construct: A genetically engineered nucleic acid. Typically comprising several elements such as genes or fragments of same, cDNAs, promoters, enhancers, terminators, polyA tails, linkers, polylinkers, operative linkers, multiple cloning sites (MCS), markers, STOP codons, other regulatory elements, internal ribosomal entry sites (IRES) or others.

Operative linker: A sequence of nucleotides or amino acid residues that bind together two parts of a nucleic acid construct or (chimeric) polypeptide in a manner securing the biological processing of the nucleic acid or polypeptide.

Pathogen: a specific causative agent of disease, especially a biological agent such as a virus, bacteria, prion or parasite that can cause disease to its host, also referred to as an infectious agent.

PBL: Peripheral blood cells are the cellular components of blood, consisting of red blood cells, white blood cells, and platelets, which are found within the circulating pool of blood and not sequestered within the lymphatic system, spleen, liver, or bone marrow.

PBMC: A Peripheral Blood Mononuclear Cell (PBMC) is a blood cell having a round nucleus, such as a lymphocyte or a monocyte. These blood cells are a critical component in the immune system to fight infection and adapt to intruders. The lymphocyte population consists of T cells (CD4 and CD8 positive ~75%), B cells and NK cells (~25% combined).

Polypeptide: Plurality of covalently linked amino acid residues defining a sequence and linked by amide bonds. The term is used analogously with oligopeptide and peptide. The term polypeptide also embraces post-translational modifications introduced by chemical or enzyme-catalyzed reactions, as are known in the art. The term can refer to a variant or fragment of a polypeptide.

Pharmaceutical carriers: also termed excipients, or stabilizers are non-toxic to the cell or individual being exposed thereto at the dosages and concentrations employed. Often the pharmaceutical carrier is an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN.™., polyethylene glycol (PEG), and PLURONICS.™.

Plurality: At least two.

Proliferative disorder: Herein any preneoplastic or neoplastic disease, benign or malignant, where "neoplastic" refers to an abnormal proliferation of cells. A non-limiting example of a proliferative disorder is cancer.

Promoter: A binding site in a DNA chain at which RNA polymerase binds to initiate transcription of messenger RNA by one or more nearby structural genes.

Signal peptide: A short sequence of amino acids that determine the eventual location of a protein in the cell, also referred to as sorting peptide.

Surfactant: A surface active agent capable of reducing the surface tension of a liquid in which it is dissolved. A surfactant is a compound containing a polar group which is hydrophilic and a non-polar group which is hydrophobic and often composed of a fatty chain.

TDO: Tryptophan 2,3-dioxygenase. Wild type human TDO is identified herein as SEQ ID NOs: 1.

$TDO_{xxx-yyy}$: As used herein this nomenclature refers to a polypeptide fragment of TDO consisting of amino acid xxx-yyy of SEQ ID NO:1.

Treg: Regulatory T cells/T lymphocytes

Treatment: The term "treatment" as used herein may refer to curative treatment and/or to ameliorating treatment and/or to treatment reducing symptoms of disease and/or treatment delaying disease progression.

Vaccine: A substance or composition capable of inducing an immune response in an individual, and in particularly in a mammal, preferably in a human being. Also referred to as an immunogenic composition in the present text. An immune response against an agent is a humoral, antibody and/or cellular response inducing memory in an organism, resulting in that said agent is being met by a secondary rather than a primary response, thus reducing its impact on the host organism. Said agent may be pathogen. In the context of the present invention the agent is preferably a cancer cell. A vaccine of the present invention may be given as a prophylaxis, in order to reduce the risk of encountering a clinical condition and/or as a therapeutic medicament for treatment of a clinical condition. The composition may comprise one or more of the following: antigen(s), nucleic acid constructs encoding one or more antigens, carriers, adjuvants and pharmaceutical carriers.

Variant: a 'variant' of a given reference nucleic acid or polypeptide refers to a nucleic acid or polypeptide that displays a certain degree of sequence homology/identity to said reference nucleic acid or polypeptide but is not identical to said reference nucleic acid or polypeptide.

Vaccine Composition

It is one of aspect of the present invention to provide a vaccine composition comprising one or more of the following:
1) Tryptophan 2,3-dioxygenase (TDO), which may be any of the TDOs described herein below in the section "Tryptophan 2,3-dioxygenase";
2) An immunogenically active peptide fragment of TDO comprising a consecutive sequence of amino acids of TDO, which may be any of the peptides described herein below in the section "Immunogenically active peptide fragment of TDO".
3) An immunogenially active peptide fragments of TDO, which is an MHC Class I-restricted peptide fragment or MHC Class II-restricted peptide fragment, such as any of the an MHC Class I-restricted peptide fragments or MHC Class II-restricted peptide fragments described in the section "MHC";
4) A functional homologue of the polypeptides under 1), 2) and 3);
5) A polypeptide comprising any of polypeptides under 1), 2), 3) and 4), which may be any of the polypeptides described herein below in the section "Polypeptides comprising TDO or a fragment thereof";
6) A nucleic acid encoding any of the polypeptides under 1), 2), 3) and 4).

In addition to the above-mentioned 1) to 4) said vaccine composition preferably also comprises an adjuvant, which for example may be any of the adjuvants described herein below in the section "Adjuvant".

Peptide fragments of TDO, which can be comprised in the vaccines of the invention are for example described herein below in the sections "Immunogenically active peptide fragment of TDO" and "Polypeptides comprising TDO or a fragment thereof". Functional homologues, which may be used in the vaccine compositions of the invention are described herein below in the sections "Tryptophan 2,3-dioxygenase"; "Immunogenically active peptide fragment of TDO" and "Functional homologues" and "Polypeptides comprising TDO or a fragment thereof".

Tryptophan 2,3-dioxygenase

Tryptophan 2,3-dioxygenase (TDO) is an enzyme involved in degradation of L-trypto-phan to N-formylkynurenine. The catabolism of tryptophan causes a depletion of tryptophan which suppresses T-cell responses and promotes immune tolerance in mammalian pregnancy, tumor resistance, chronic infection, autoimmunity and allergic inflammation.

In particular, TDO may be an enzyme capable of catalyzing the following reaction:

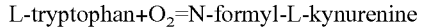
L-tryptophan+$O_2$=N-formyl-L-kynurenine

TDO according to the present invention may be any useful TDO. In general it is preferred that the TDO is TDO of the same species which is intended to treat with the vaccine compositions of the invention. In preferred embodiments of the invention, the vaccine composition is intended for administration to a human being, and hence TDO may be human TDO. The amino acid sequence of wild type human TDO is presented as SEQ ID NO:1 herein.

Thus, TDO may preferably be TDO of SEQ ID NO:1 or a functional homologue thereof sharing at least 70% sequence identity to TDO of SEQ ID NO: 1, and accordingly, functional homologuea preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example at least 99% sequence identity with human TDO of SEQ ID NO:1.

Functional homologues of TDO and methods for determining sequence identity are described in more detail in the section "Functional homologues" herein below.

Since TDO potentially may have unwanted activity, then in one embodiment of the invention, the vaccine composition comprises mutant TDO, which is not capable of catalyzing above-mentioned reaction, or which only catalyzing above-mentioned reaction with an activity at the most 10% of the TDO of SEQ ID NO:1. Such mutant TDO may in particular be TDO of SEQ ID NO:1 wherein one or more of the amino acids 144, 151, 328 and/or 342 have been mutated to another amino acid or are deleted. In the context of the present invention a "functional homologue" of TDO may be mutant TDO, which do not have the catalytic activity of wild type TDO, but which has the capability to induce an immune response to cells expressing TDO Immunogenically Active Peptide Fragment of TDO The wild-type human TDO i.e. the naturally occurring non-mutated version of the protein is identified in SEQ ID NO: 1. The present invention covers vaccine compositions comprising TDO; immunologically active peptide fragments of TDO; peptide fragments of TDO, wherein at the most two amino acids have been substituted; and/or functional homologues of TDO comprising a sequence identity of at least 70% to SEQ ID NO: 1. The term polypeptide fragment is used herein to define any non-full length (as compared to SEQ ID NO: 1) string of amino acid residues that are directly derived from or synthesized to be identical with SEQ ID NO:1.

A functional homologue can be defined as a full length or fragment of TDO that differs in sequence from the wild-type TDO, such as wild-type human TDO, but is still capable of inducing an immune response against TDO expressing cells such as cancer cells and DCs. The TDO expressed in these cells may be wild type or endogenously mutated (such as a congenital mutant or a mutation induced during cell division or other). A functional homologue may be a mutated version or an alternative splice variant of the wild-type TDO. In another aspect, functional homologues of TDO are defined as described herein below. A functional homologue may be, but is not limited to, a recombinant version of full length or fragmented TDO with one or more mutations and/or one or more sequence deletions and/or additions introduced ex vivo.

Accordingly, in a specific embodiment the immunogenically active peptide fragment of the invention consists of at the most 400 amino acid residues, such as of the most 300 amino acids residues, for example at the most 200 amino acid residues, such as at the most 100 amino acid residues, for example at the most 50 amino acid residues, for example at the most 45 amino acid residues, such as at the most 40 amino acid residues, for example at the most 35 amino acid residues, such as at the most 30 amino acid residues, for example at the most 25 amino acid residues, such as 18 to 25 consecutive amino acids of TDO as identified in SEQ ID NO: 1 or a functional homologue thereof; the functional homologue being a polypeptide of identical sequence except that at the most three amino acids have been substituted, such as at the most two amino acids have been substituted, such as at the most one amino acid has been substituted. Said immunogenically active peptide fragment may also consists of at the most 400 amino acid residues, such as of the most 300 amino acids residues, for example at the most 200 amino acid residues, such as at the most 100 amino acid residues, for example at the most 50 amino acid residues, for example at the most 45 amino acid residues, such as at the most 40 amino acid residues, for example at the most 35 amino acid residues, such as at the most 30 amino acid residues, for example at the most 25 amino acid residues, such as 18 to 25 consecutive amino acids of TDO as identified in SEQ ID NO: 1, wherein one or more of the amino acids 144, 151, 328 and/or 342 have been mutated to another amino acid or are deleted.

In one preferred embodiment of the invention, the immunogenically active peptide fragment consists of in the range of 18 to 25 amino acids, preferably of 20 consecutive amino acids of TDO as identified in SEQ ID NO: 1 or a functional homologue thereof; the functional homologue being a polypeptide of identical sequence except that at the most three amino acids have been substituted, such as at the most two amino acids have been substituted, such as at the most one amino acid has been substituted.

Accordingly in another specific embodiment the immunogenically active peptide fragment of the invention consists of the most 25 amino acid residues, such as at the most 24 amino acid residues, such as at the most 23 amino acid residues, such as at the most 22 amino acid residues, such as at the most 21 amino acid residues, such as at the most 20 amino acid residues, for example at the most 19 amino acid residues, such as at the most 18 amino acid residues, for example at the most 17 amino acid residues, such as at the most 16 amino acid residues, for example at the most 15 amino acid residues, such as at the most 14 amino acid residues, for example at the most 13 amino acid residues, such as at the most 12 amino acid residues, for example at the most 11 amino acid residues, such as 8 to 10 consecutive amino acids from TDO of SEQ ID NO: 1 or a functional homologue thereof; the functional homologue being a polypeptide of identical sequence except that at the most three amino acids have been substituted, such as at the most two amino acids have been substituted, such as at the most one amino acid has been substituted.

In one preferred embodiment of the invention, the immunogenically active peptide peptide comprises at the most 10 consecutive amino acid residues from TDO, such as at the most 9 consecutive amino acid residues, such as 8 consecutive amino acid residues, such as 7 consecutive amino acid residues from TDO as identified in SEQ ID NO: 1 or a functional homologue thereof; the functional homologue being a polypeptide of identical sequence except that at the most three amino acids have been substituted, such as at the most two amino acids have been substituted, such as at the most one amino acid has been substituted. In particular, the immunogenically active peptide may consist of 10 consecutive amino acid residues from TDO of SEQ ID NO:1 or the immunogenically active peptide may consist of 9 consecutive amino acid residues from TDO of SEQ ID NO:1.

In some embodiments of the invention the immunogenically active peptide may be selected from the group consisting of peptides listed in Table 1 or a functional homologue thereof; the functional homologue being a polypeptide of identical sequence except that at the most three amino acids have been substituted, such as at the most two amino acids have been substituted, such as at the most one amino acid has been substituted.

TABLE 1

Useful TDO peptides

| SEQ ID NO | Name | Amino acid numbers in SEQ ID NO: 1 | Sequence |
|---|---|---|---|
| SEQ ID NO: 2 | TDO1 | $TDO_{159-168}$ | RLLENKIGVL |
| SEQ ID NO: 3 | TDO2 | $TDO_{200-208}$ | TLLELVEAWL |
| SEQ ID NO: 4 | TDO3 | $TDO_{72-81}$ | FIITHQAYEL |
| SEQ ID NO: 5 | TDO4 | $TDO_{40-48}$ | LIYGNYLHL |
| SEQ ID NO: 6 | TDO5 | $TDO_{123-132}$ | KLLVQQFSIL |
| SEQ ID NO: 7 | TDO6 | $TDO_{65-74}$ | KIHDEHLFII |
| SEQ ID NO: 8 | TDO7 | $TDO_{192-201}$ | LLKSEQEKTL |
| SEQ ID NO: 9 | TDO8 | $TDO_{309-317}$ | QLLTSLMDI |
| SEQ ID NO: 10 | TDO9 | $TDO_{85-93}$ | QILWELDSV |
| SEQ ID NO: 11 | TDO10 | $TDO_{130-138}$ | SILETMTAL |
| SEQ ID NO: 12 | TDO11 | $TDO_{276-284}$ | LLSKGERRL |
| SEQ ID NO: 13 | TDO12 | $TDO_{364-372}$ | DLFNLSTYL |
| SEQ ID NO: 14 | TDO13 | $TDO_{225-234}$ | KLEKNITRGL |
| SEQ ID NO: 15 | TDO14 | $TDO_{372-381}$ | LIPRHWIPKM |
| SEQ ID NO: 16 | TDO15 | $TDO_{380-389}$ | KMNPTIHKFL |
| SEQ ID NO: 17 | | $TDO_{118-137}$ | VSVILKLLVQQFSILETMTA |
| SEQ ID NO: 18 | | $TDO_{303-322}$ | RFQVPFQLLTSLMDIDSLMT |

In a preferred embodiment of the invention the immunogenically active peptide is selected from the group consisting of:
a) SEQ ID NO:3 ($TDO_{200-208}$);
b) SEQ ID NO:6 ($TDO_{123-132}$);
c) SEQ ID NO:9 ($TDO_{309-317}$);
d) SEQ ID NO:13 ($TDO_{364-372}$);
e) SEQ ID NO:17 ($TDO_{118-137}$);
f) SEQ ID NO:18 ($TDO_{303-322}$); and
g) a functional homologue of the polypeptide according to any of a) to f); the functional homologue being a polypeptide of identical sequence except that at the most three amino acids have been substituted, such as at the most two amino acids have been substituted, such as at the most one amino acid has been substituted.

Other peptides of the invention comprise (or more preferably consist of) between 4 and 120, preferably between 8 and 100, more preferably between 10 and 75, yet more preferably between 12 and 60, even more preferably between 15 and 40, such as between 18 and 25 contiguous amino acids of TDO of SEQ ID NO: 1 or a functional homologue thereof having at least 70%, preferably at least 80%, more preferably at least 90%, even more preferably at least 95%, yet more preferably at least 98%, for example at least 99% sequence identity to SEQ ID NO: 1.

Functional Homologues

Functional homologues of TDO or immunogenically active fragments thereof, are polypeptides, which also are immunogenically active, and which shares at least some degree of sequence identity with TDO, and in particular with TDO of SEQ ID NO:1.

For shorter polypeptides, such as for polypeptide shorter than 100 amino acids, such as shorter than 50 amino acids, for example shorter than 25 amino acids, then functional homologues may be an immunogenically active polypeptide of identical sequence except that at the most three amino acids have been substituted, such as at the most two amino acids have been substituted, such as at the most one amino acid has been substituted.

Alternatively, a functional homologue may be an immunogenically active polypeptide sharing at least 70% sequence identity to TDO of SEQ ID NO: 1, and accordingly, functional homologuea preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with human TDO of SEQ ID NO:1.

Sequence identity can be calculated using a number of well-known algorithms and applying a number of different gap penalties. The sequence identity is calculated relative to full-length reference sequence, e.g. to full length SEQ ID NO: 1. Any sequence alignment tool, such as but not limited to FASTA, BLAST, or LALIGN may be used for searching homologues and calculating sequence identity. Moreover, when appropriate any commonly known substitution matrix, such as but not limited to PAM, BLOSSUM or PSSM matrices may be applied with the search algorithm. For example, a PSSM (position specific scoring matrix) may be applied via the PSI-BLAST program. Moreover, sequence alignments may be performed using a range of penalties for gap opening and extension. For example, the BLAST algorithm may be used with a gap opening penalty in the range 5-12, and a gap extension penalty in the range 1-2.

Functional homologues may further comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins, however it is preferred that the functional equivalent does not contain chemical modifications.

Any changes made to the sequence of amino acid residues compared to that of TDO of SEQ ID NO: 1 are preferably conservative substitutions. A person skilled in the art will know how to make and assess 'conservative' amino acid substitutions, by which one amino acid is substituted for another with one or more shared chemical and/or physical characteristics. Conservative amino acid substitutions are less likely to affect the functionality of the protein. Amino acids may be grouped according to shared characteristics. A conservative amino acid substitution is a substitution of one amino acid within a predetermined group of amino acids for another amino acid within the same group, wherein the amino acids within a predetermined groups exhibit similar or substantially similar characteristics.

Thus, in an embodiment of the present invention, the vaccine composition comprises a polypeptide consisting of a consecutive sequence of TDO of SEQ ID NO: 1 in the range of 8 to 50 amino acids, preferably in the range of 8 to 10 or 20 to 25 amino acids, wherein at the most three amino acid has been substituted, and where the substitution preferably is conservative.

Polypeptides Comprising TDO or a Fragment Thereof

It is also comprised within the invention that the vaccine compositions of the invention may comprise a polypeptide comprising either TDO or a fragment thereof. Thus, the immunogenically active peptide fragment of TDO may for example be any of the polypeptides comprising a TDO fragment described herein in this section.

In particular, such polypeptides may comprise full length TDO, such as any of the TDOs described herein above in the section "Tryptophan 2,3-doxygenase". For example the polypeptide may comprise TDO of SEQ ID NO:1 or a functional homologue thereof sharing at least 70%, such as atleast 80%, for example at least 90%, such as at least 95% sequence identity therewith. In particular, such polypeptides may comprise at the most 100, such as at the most 50, for example at the most 25, such as at the most 10 amino acids in addition to TDO of SEQ ID NO:1.

It is also comprised within the invention that the vaccine compositions may comprise a polypeptide comprising a fragment of TDO, such as any of the fragments described herein above in the section "Immunogenically active peptide fragment of TDO". Said polypeptide may also comprise any of the immunogenically active peptide fragments of TDO, which is an MHC Class I-restricted peptide fragment or MHC Class II-restricted peptide fragment, such as any of the an MHC Class I-restricted peptide fragments or MHC Class II-restricted peptide fragments described in the section "MHC".

Thus, said polypeptide may be a polypeptide of at the most 400 amino acids, such as at the most 300 amino acids, for example at the most 200 amino acids, such as at the most 100 amino acids, for example at the most 50 amino acids comprising a consecutive sequence of amino acids of SEQ ID NO:1, wherein said consecutive sequence of amino acids of SEQ ID NO:1 consists of at the most 50 amino acid residues, for example at the most 45 amino acid residues, such as at the most 40 amino acid residues, for example at the most 35 amino acid residues, such as at the most 30 amino acid residues, for example at the most 25 amino acid residues, such as in the range of 18 to 25, such as in the range of 8 to 10 consecutive amino acids from TDO of SEQ ID NO: 1 or a functional homologue thereof.

In particular, said polypeptide may be a polypeptide of at the most 100 amino acids, such as at the most 80 amino acids, for example at the most 60 amino acids, such as at the most 40 amino acids, for example at the most 30 amino acids comprising a consecutive sequence of amino acids of SEQ ID NO:1, wherein said consecutive sequence of amino acids of SEQ ID NO:1 consists of in the range of 18 to 25, such as of 20 consecutive amino acids from TDO of SEQ ID NO: 1 or a functional homologue thereof. Thus, said polypeptide may be a polypeptide of at the most 100 amino acids, such as at the most 80 amino acids, for example at the most 60 amino acids, such as at the most 40 amino acids, for example at the most 30 amino acids comprising an immunogenically active peptide selected from the group consisting of:

a) SEQ ID NO:3 (TDO$_{200-208}$);
b) SEQ ID NO:6 (TDO$_{123-132}$);
c) SEQ ID NO:9 (TDO$_{309-317}$);
d) SEQ ID NO:13 (TDO$_{364-372}$);
e) SEQ ID NO:17 (TDO$_{118-137}$);
f) SEQ ID NO:18 (TDO$_{303-322}$); and
g) a functional homologue of the polypeptide according to any of a) to f); the functional homologue being a polypeptide of identical sequence except that at the most three amino acids have been substituted, such as at the most two amino acids have been substituted, such as at the most one amino acid has been substituted.

In one embodiment, the immunogenically active peptide fragment of TDO may be a polypeptide comprising or consisting a consecutive sequence of at the most 400 amino acids, such as at the most 300 consecutive amino acids, for example at the most 200 consecutive amino acids, such as at the most 100 consecutive amino acids, for example at the most 50 consecutive amino acids, for example at the most 45 consecutive amino acid residues, such as at the most 40 consecutive amino acid residues, for example at the most 35 consecutive amino acid residues, such as at the most 30 consecutive amino acid residues, for example at the most 25 consecutive amino acid residues, such as in the range of 18 to 25, such as in the range of 8 to 10 consecutive amino acids from TDO of SEQ ID NO: 1 or a functional homologue thereof where at the most three amino acids have been substituted, such as at the most two amino acids have been substituted, such as at the most one amino acid has been substituted, and wherein said peptide fragment of TDO comprises at least one sequence selected from the group consisting of:

a) SEQ ID NO:3 (TDO$_{200-208}$);
b) SEQ ID NO:6 (TDO$_{123-132}$);
c) SEQ ID NO:9 (TDO$_{309-317}$);
d) SEQ ID NO:13 (TDO$_{364-372}$);
e) SEQ ID NO:17 (TDO$_{118-137}$);
f) SEQ ID NO:18 (TDO$_{303-322}$);and
g) a functional homologue of the polypeptide according to any of a) to f); the functional homologue being a polypeptide of identical sequence except that at the most three amino acids have been substituted, such as at the most two amino acids have been substituted, such as at the most one amino acid has been substituted.

Said polypeptide may also be a polypeptide of at the most 100 amino acids, such as at the most 50 amino acids, for example at the most 30 amino acids, such as at the most 20 amino acids, for example at the most 15 amino acids comprising a consecutive sequence of amino acids of SEQ ID NO:1, wherein said consecutive sequence of amino acids of SEQ ID NO:1 consists of in the range of 8 to 10, such as of 9 or 10 consecutive amino acids from TDO of SEQ ID NO: 1 or a functional homologue thereof. Thus, said polypeptide may be a polypeptide of at the most 100 amino acids, such as at the most 50 amino acids, for example at the most 30 amino acids, such as at the most 20 amino acids, for example at the most 15 amino acids comprising an immunogenically active peptide selected from the group consisting of:

a) SEQ ID NO:3 (TDO$_{200-208}$);
b) SEQ ID NO:6 (TDO$_{123-132}$);
c) SEQ ID NO:9 (TDO$_{309-317}$);
d) SEQ ID NO:13 (TDO$_{364-372}$); and
e) a functional homologue of the polypeptide according to any of a) to d); the functional homologue being a polypeptide of identical sequence except that at the most three amino acids have been substituted, such as at the most two amino acids have been substituted, such as at the most one amino acid has been substituted.

MHC

It is comprised within the invention that the immunogenially active peptide fragments of TDO may be an MHC Class I-restricted peptide fragment or MHC Class II-restricted peptide fragment, such as any of the an MHC Class I-restricted peptide fragments or MHC Class II-restricted peptide fragments described in this section.

There are two types of MHC molecules; MHC class I molecules and MHC class II molecules. MHC class I molecules are recognized by CD8 T-cells, which are the principal effector cells of the adaptive immune response. MHC class II molecules are mainly expressed on the surface of antigen presenting cells (APCs), the most important of which appears to be the dendritic cells. APCs stimulate naïve T-cells, as well as other cells in the immune system. They stimulate both CD8 T-cells and CD4 T-cells.

In one embodiment, the invention provides immunogenically active TDO peptides (optionally comprised in larger peptides and/or in vaccine compositions), wherein said immunogenically active TDO peptides are MHC Class I-restricted peptide fragments consisting of 8-10 consecutive amino acids from TDO of SEQ ID NO 1 or a functional homologue thereof, wherein at the most two amino acids of SEQ ID NO 1 have been substituted, which are characterized by having at least one of several features, one of which is the ability to bind to the Class I HLA molecule to which it is restricted at an affinity as measured by the amount of the peptide that is capable of half maximal recovery of the Class I HLA molecule ($C_{50}$ value) which is at the most 50 µM as determined by the assembly binding assay as described herein. This assembly assay is based on stabilization of the HLA molecule after loading of peptide to the peptide transporter deficient cell line T2. Subsequently, correctly folded stable HLA heavy chains are immunoprecipitated using conformation dependent antibodies and the peptide binding is quantitated. The peptides of this embodiment comprises (or more preferably consists of) at the most 200, preferably at the most 100, more preferably at the most 50, yet more preferably at the most 25, even more preferably at the most 20, yet even more preferably at the most 15, such as at the most 10, for example in the range of 8 to 10 consecutive amino acids of TDO of SEQ ID NO 1or a functional homologue thereof wherein at the most two amino acids of SEQ ID NO 1 have been substituted.

This assay provides a simple means of screening candidate peptides for their ability to bind to a given HLA allele molecule at the above affinity. In preferred embodiments, the peptide fragment of the invention in one having a $C_{50}$ value, which is at the most 30 µM, such as a $C_{50}$ value, which is at the most 20 µM including $C_{50}$ values of at the most 10 µM, at the most 5 µM and at the most 2 µM.

In another preferred embodiment, there are provided novel MHC Class II-restricted peptide fragments of TDO of SEQ ID NO 1 or a functional homologue thereof, wherein at the most two amino acids of SEQ ID NO 1 have been substituted, (also referred to herein as "peptides"), which are characterized by having at least one of several features described herein below. The peptides of this embodiment comprises (or more preferably consists of) between 4 and 120, preferably between 8 and 100, more preferably between 10 and 75, yet more preferably between 12 and 60, even more preferably between 15 and 40, such as between 18 and 25 consecutive amino acids of TDO of SEQ ID NO 1 or a functional homologue thereof, wherein at the most two, preferably at the most one amino acids of SEQ ID NO 1 have been substituted, Thus there are provided novel MHC Class I-restricted peptide fragments of 8-10 amino acids or novel MHC Class II-restricted peptide fragments of 18-25 amino acids of TDO of SEQ ID NO 1 or a functional homologue thereof, wherein at the most two amino acids of SEQ ID NO 1 have been substituted, which are characterized by having at least one of several features described herein below, one of which is the ability to bind to the Class I or Class II HLA molecule to which it is restricted.

In particular embodiments there are provided peptide fragments, which is an MHC Class I-restricted peptide or an MHC class II-restricted peptide having at least one of the following characteristics:
(i) capable of eliciting INF-γ-producing cells in a PBL population of at least one cancer patient at a frequency of at least 1 per $10^4$ PBLs as determined by an ELISPOT assay, and/or
(ii) capable of in situ detection in a tumor tissue of CTLs that are reactive with the epitope peptide.
(iii) capable of inducing the growth of TDO specific T-cells in vitro.

More preferred peptides according to the present invention are peptides capable of raising a specific T-cell response as determined by an ELISPOT assay, for example the ELISPOT assay described in Example 1 herein below. Some peptides although they do not bind MHC class I or class II with high affinity, may still give rise to a T-cell response as determined by ELISPOT. Other peptides capable of binding MHC class I or class II with high affinity also give rise to a T-cell response as determined by ELISPOT. Both kinds of peptides are preferred peptides according to the invention.

Hence, preferred peptides according to the present invention are peptides capable of raising a specific T-cell response as measured by an ELISPOT assay, wherein more than 50 peptide specific spots per $10^8$ cells, more preferably per $10^7$, even more preferably per $10^6$, yet more preferably per $10^5$ cells, such as per $10^4$ cells are measured.

Most preferred peptides according to the present invention are peptides that are capable of eliciting a cellular immune response in an individual suffering from a clinical condition characterized by the expression of TDO, the clinical condition preferably being a cancer or infection, and most preferably a cancer.

Preferred peptides according to the present invention are capable of eliciting a specific cellular immune response directed against cells expressing TDO. Thus, the peptides preferably can activate TDO specific T-cells recognizing cells expressing TDO.

As described above, the HLA system represents the human major histocompatibility (MHC) system. Generally, MHC systems control a range of characteristics: transplantation antigens, thymus dependent immune responses, certain complement factors and predisposition for certain diseases. More specifically, the MHC codes for three different types of molecules, i.e. Class I, II and III molecules, which determine the more general characteristics of the MHC. Of these molecules, the Class I molecules are so-called HLA-A, HLA-B and HLA-C molecules that are presented on the surface of most nucleated cells and thrombocytes.

The peptides of the present invention are characterized by their ability to bind to (being restricted by) a particular MHC Class I HLA molecule. Thus, in one embodiment the peptide is one which is restricted by a MHC Class I HLA-A molecule including HLA-A1, HLA-A2, HLA-A3, HLA-A9, HLA-A10, HLA-A11, HLA-Aw19, HLA-A23(9), HLA-A24(9), HLA-A25(10), HLA-A26(10), HLA-A28, HLA-A29(w19), HLA-A30(w19), HLA-A31(w19), HLA-A32 (w19), HLA-Aw33(w19), HLA-Aw34(10), HLA-Aw36, HLA-Aw43, HLA-Aw66(10), HLA-Aw68(28), HLA-A69 (28). More simple designations are also used throughout the literature, where only the primary numeric designation is used, e.g. HLA-A19 or HLA-A24 instead of HLA-Aw19 and HLA-A24(49), respectively. In specific embodiments, the peptide of the invention is restricted a MHC Class I HLA species selected from the group consisting of HLA-A1, HLA-A2, HLA-A3, HLA-A11 and HLA-A24. In specific embodiment, the peptide of the invention is restricted a MHC Class I HLA species HLA-A2 or HLA-A3.

In further useful embodiments, the peptide of the invention is a peptide, which is restricted by a MHC Class I HLA-B molecule including any of the following: HLA-B5, HLA-B7, HLA-B8, HLA-B12, HLA-B13, HLA-B14, HLA-B15, HLA-B16, HLA-B17, HLA-B18, HLA-B21, HLA-Bw22, HLA-B27, HLA-B35, HLA-B37, HLA-B38, HLA-B39, HLA-B40, HLA-Bw41, HLA-Bw42, HLA-B44, HLA-B45, HLA-Bw46 and HLA-Bw47. In specific embodiments of the invention, the MHC Class I HLA-B species to which the peptide of the invention is capable of binding is selected from HLA-B7, HLA-B35, HLA-B44, HLA-B8, HLA-B15, HLA-B27 and HLA-B51.

In further useful embodiments, the peptide of the invention is a peptide, which is restricted by a MHC Class I HLA-C molecule including but not limited to any of the following: HLA-Cw1, HLA-Cw2, HLA-Cw3, HLA-Cw4, HLA-Cw5, HLA-Cw6, HLA-Cw7 and HLA-Cw1.

In further useful embodiments, the peptide of the invention is a peptide, which is restricted by a MHC Class II HLA molecule including but not limited to any of the following: HLA-DPA-1, HLA-DPB-1, HLA-DQA1, HLA-DQB1, HLA-DRA, HLA-DRB and all alleles in these groups and HLA-DM, HLA-DO.

The selection of peptides potentially having the ability to bind to a particular HLA molecule can be made by the alignment of known sequences that bind to a given particular HLA molecule to thereby reveal the predominance of a few related amino acids at particular positions in the peptides. Such predominant amino acid residues are also referred to herein as "anchor residues" or "anchor residue motifs". By following such a relatively simple procedure based on known sequence data that can be found in accessible databases, peptides can be derived from TDO, which are likely to bind to a specific HLA molecule. Representative examples of such analyses for a range of HLA molecules are given in the below table:

TABLE 2

| HLA allele | Position 1 | Position 2 | Position 3 | Position 5 | Position 6 | Position 7 | C-terminal |
|---|---|---|---|---|---|---|---|
| HLA-A1 |  | T, S | D, E |  |  | L | Y |
| HLA-A2 |  | L, M |  |  | V |  | L, V |
| HLA-A3 |  | L, V, M | F, Y |  |  |  | K, Y, F |
| HLA-A11 |  | V, I, F, Y | M, L, F, Y, I |  |  |  | K, R |
| HLA-A23 |  | I, Y |  |  |  |  | W, I |
| HLA-A24 |  | Y |  | I, V | F |  | I, L, F |
| HLA-A25 |  | M, A, T | I |  |  |  | W |
| HLA-A26 | E, D | V, T, I, L, F |  |  | I, L, V |  | Y, F |
| HLA-A28 | E, D | V, A, L |  |  |  |  | A, R |

TABLE 2-continued

| HLA allele | Position 1 | Position 2 | Position 3 | Position 5 | Position 6 | Position 7 | C-terminal |
|---|---|---|---|---|---|---|---|
| HLA-A29 | | E | | | | | Y, L |
| HLA-A30 | | Y, L, F, V | | | | | Y |
| HLA-A31 | | | L, M, F, Y | | | | R |
| HLA-A32 | | I, L | | | | | W |
| HLA-A33 | | Y, I, L, V | | | | | R |
| HLA-A34 | | V, L | | | | | R |
| HLA-A66 | E, D | T, V | | | | | R, K |
| HLA-A68 | E, D | T, V | | | | | R, K |
| HLA-A69 | | V, T, A | | | | | V, L |
| HLA-A74 | | T | | | | | V, L |
| HLA-B5 | | A, P | F, Y | | | | I, L |
| HLA-B7 | * | P | | | | | L, F |
| HLA-B8 | | | K | | K, R | | L |
| HLA-B14 | | R, K | | | | | L, V |
| HLA-B15 (B62) | | Q, L, K, P, H, V, I, M, S, T | | | | | F, Y, W |
| HLA-B17 | | | | | | | L, V |
| HLA-B27 | | R | | | | | Y, K, F, L |
| HLA-B35 | | P | | | | | I, L, M, Y |
| HLA-B37 | | D, E | | | | | I, L, M |
| HLA-B38 | | H | D, E | | | | F, L |
| HLA-B39 | | R, H | | | | | L, F |
| HLA-B40 (B60, 61) | | E | F, I, V | | | | L, V, A, W, M, T, R |
| HLA-B42 | | L, P | | | | | Y, L |
| HLA-B44 | | E | | | | | F, Y, W |
| HLA-B46 | | M, I, L, V | | | | | Y, F |
| HLA-B48 | | Q, K | | | | | L |
| HLA-B51 | | A, P, G | | | | | F, Y, I, V |
| HLA-B52 | | Q | F, Y | | | | I, V |
| HLA-B53 | | P | | | | | W, F, L |
| HLA-B54 | | P | | | | | |
| HLA-B55 | | P | | | | | A, V |
| HLA-B56 | | P | | | | | A, V |
| HLA-B57 | | A, T, S | | | | | F, W, Y |
| HLA-B58 | | A, T, S | | | | | F, W, Y |
| HLA-B67 | | P | | | | | L |
| HLA-B73 | | R | | | | | P |
| HLA-Cw1 | | A, L | | | | | L |
| HLA-Cw2 | | A, L | | | | | F, Y |
| HLA-Cw3 | | A, L | | | | | L, M |
| HLA-Cw4 | | Y, P, F | | | | | L, M, F, Y |
| HLA-Cw6 | | | | | | | L, I, V, Y |
| HLA-Cw6 | | Y | | | | | L, Y, F |
| HLA-Cw8 | | Y | | | | | L, I, |
| HLA-Cw16 | | A, L | | | | | L, V |

*In one embodiment there is no specific anchor residue for this position, however in a preferred embodiment the anchor residue is R or A.

Thus, as an example, nonapeptides potentially having the ability to bind to HLA-A3 would have one of the following sequences: Xaa-L-Y-Xaa-Xaa-Xaa-Xaa-Xaa-K, Xaa-L-Y-Xaa-Xaa-Xaa-Xaa-Xaa-Y; Xaa-L-Y-Xaa-Xaa-Xaa-Xaa-Xaa-F or Xaa-V-Y-Xaa-Xaa-Xaa-Xaa-Xaa-K (Xaa indicating any amino acid residue). In a similar manner, sequences potentially having the ability to bind to any other HLA molecule can be designed. It will be appreciated that the person of ordinary skill in the art will be able to identify further "anchor residue motifs" for a given HLA molecule.

The peptide of the invention may have a sequence which is a native sequence of the TDO from which is derived. However, peptides having a higher affinity to any given HLA molecule may be derived from such a native sequence by modifying the sequence by substituting, deleting or adding at least one amino acid residue, e.g. on the basis of the procedure described above, whereby anchor residue motifs in respect of the given HLA molecule are identified.

Thus, in useful embodiments, the polypeptides of the invention include peptides, the sequences of which comprise, for each of the specific HLA alleles listed in the table, any of the amino acid residues as indicated in the table.

Thus, the peptides of the invention may be any of the above-mentioned peptides comprising consecutive sequences from TDO, wherein in the range of 1 to 10, preferably in the range of 1 to 5, more preferably in the range of 1 to 3, even more preferably in the range of 1 to 2, yet more preferably 1 amino acid has been exchanged for another amino acid, preferably in a manner so that the peptide comprises one or more, preferably all anchor residues of a given HLA-A specific peptide as indicated in the table above.

Examples preferable HLA species include, to which preferred peptides of the present invention are restricted include: a MHC Class I HLA species selected from the group consisting of HLA-A1, HLA-A2, HLA-A3, HLA-A11 and HLA-A24, more preferably the peptide is restricted by HLA-A3 or HLA-A2. Alternatively a preferred HLA species includes MHC Class I HLA-B species selected from the group consisting of HLA-B7, HLA -B35, HLA -B44, HLA-B8, HLA-B15, HLA-B27 and HLA-B51.

An approach to identifying polypeptides of the invention includes the following steps: selecting a particular HLA molecule, e.g. one occurring at a high rate in a given population, carrying out an alignment analysis as described above to identify "anchor residue motifs" in the TDO protein, isolating or constructing peptides of a suitable size that comprise one or more of the identified anchor residues and testing the resulting peptides for the capability of the peptides to elicit INF-γ-producing cells in a PBL population of a cancer patient at a frequency of at least 1 per $10^4$ PBLs as determined by an ELISPOT assay as described in Example 1.

In one aspect of the present invention, TDO-derived peptides longer than 8 to 10 amino acid residues are provided. Polypeptides longer than 8 to 10 amino acids are processed by the proteasome to a shorter length for binding to HLA molecules. Thus, when administering a polypeptide longer than 8 to 10 amino acid residues long, the "long" polypeptide/protein/protein fragment/variant of TDO may be processed in vivo into a series of smaller peptides in the cytosol by the proteasome. An advantage of using a longer polypeptide that may be processed by the proteasome into a variety of different shorter peptides is that more HLA classes may be targeted with one peptide than one 8 to 10 amino acid peptide that is restricted to a particular HLA class.

Surprisingly, some of the peptides of the present invention bind to MHC molecules with an affinity sufficiently high to render substitutions unnecessary and are ready for use as antigens as they are presented here. Preferably, the vaccine composition of the present invention comprises one or more of the following: TDO protein (SEQ ID NO: 1), polypeptide fragments here from, likewise variants, functional homologues of full length and partial length TDO, contiguous peptides of TDO and functional homologues of these. More preferably, the vaccine composition comprises any of the sequences listed in Table 1. Very preferably, the vaccine composition comprises the peptides SEQ ID NO:3 (TDO$_{200-208}$);SEQ ID NO:6 (TDO$_{123-132}$);SEQ ID NO:9 (TDO$_{309-317}$);SEQ ID NO:13 (TDO$_{364-372}$);SEQ ID NO:17 (TDO$_{118-137}$); and/or SEQ ID NO:18 (TDO$_{303-322}$).

A significant feature of the peptide of the invention is its capability to recognize or elicit INF-γ-producing responder T cells, i.e. cytotoxic T cells (CTLs) that specifically recognize the particular peptide in a PBL population, on an APC or tumor/neoplastic cells of an individual suffering from a cancer and/or an infection (target cells). This activity is readily determined by subjecting PBLs, APCs or tumor cells from an individual to an ELISPOT assay. Prior to the assay, it may be advantageous to stimulate the cells to be assayed by contacting the cells with the peptide to be tested. Preferably, the peptide is capable of eliciting or recognizing INF-γ-producing T cells at a frequency of at least 1 per $10^4$ PBLs as determined by an ELISPOT assay as used herein. More preferably the frequency is at least 5 per $10^4$ PBLs, most preferably at least 10 per $10^4$ PBLs, such as at least 50 or 100 per $10^4$ PBLs.

The ELISPOT assay represents a strong tool to monitor TDO peptide specific T-cell responses. A major implication of the findings herein is that the peptides of the invention are expressed and complexed with HLA molecules on cancer cells and/or TDO expressing APCs. This renders these cancer cells susceptible to destruction by CTLs and emphasizes the usefulness of TDO immunization to fight cancer and infections. The presence of spontaneous CTL-responses in PBLs from melanoma patients to HLA-restricted TDO derived peptide epitopes shows the immunotherapeutic potential of TDO immunogenic peptides.

In an embodiment of the present invention the peptide of the invention is capable of eliciting INF-γ-producing cells in a PBL population of an individual suffering from an clinical condition where TDO of SEQ ID NO:1 or a functional homologue thereof having at least 70% identity to SEQ ID NO 1 is expressed. The clinical condition is preferably a cancer or and infection and most preferably a cancer.

Individual

The individual to be treated with the vaccine composition of the present invention is an individual suffering from a clinical condition. The individual is preferably of a mammalian species and most preferably a human being. The individual may be of any age, young or old, and may be either male or female. The clinical condition from which the individual suffers may be a neoplastic disease such as a cancer, or an infection such as a microbial or viral infection e.g. HIV.

An embodiment of the present invention provides a vaccine for the treatment, reduction of risk of, stabilization of or prevention of a cancer. In another embodiment the present invention provides a vaccine for the treatment, reduction of risk of, stabilization of or prevention of a disease stemming from an infection, such as a microbial or viral infection.

Cancer

The vaccine composition of the present invention may be used to prevent, reduce the risk of or treat a clinical condition. Preferably, the clinical condition is associated with or characterized by the expression of TDO. TDO may be TDO as identified in SEQ ID NOs: 1 or may be a homolog sharing at least 70% identity with any of these in their wild type forms, but need not be functional. It is understood hereby that the expression level of TDO (the expression being expression of hnRNA, mRNA, precursor protein, fully processed protein and so on) is the same or higher than in an individual not suffering from a clinical condition.

The one embodiment of the invention the clinical condition is a proliferative disorder, such as a preneoplastic or neoplastic disorder. In a preferred embodiment of the invention, the clinical condition is cancer. Cancer (malignant neoplasm) is a class of diseases in which a group of cells display the traits of uncontrolled growth (growth and division beyond the normal limits), invasion (intrusion on and destruction of adjacent tissues), and sometimes metastasis (spread to other locations in the body via lymph or blood). These three malignant properties of cancers differentiate them from benign tumors, which are self-limited, do not invade or metastasize. Most cancers form a tumor but some, like leukemia, do not.

A non-limiting group of cancers given as examples of cancers that may be treated, managed and/or prevented by administration of the vaccine of the present invention include: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharingioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute mega-karyocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In a preferred embodiment the vaccine composition according to the invention is capable of eliciting a clinical response in subject, wherein the clinical response may be characterized by a stable disease, in a preferred embodiment the clinical response may be characterized by a partial response or preferably the clinical response may be characterized by complete remission of a cancer. Preferably, the cancer is selected from the group of; melanoma, breast cancer, ovarian cancer, lung cancer, pancreatic cancer, hematologic cancers (such as leukemias), colon and renal cell cancers.

In one aspect of the invention the vaccine composition is capable of eliciting a clinical response in an individual. In one embodiment the clinical response may be characterized by a stable disease (no further worsening or progression), in a preferred embodiment the clinical response may be characterized by a partial response or preferably the clinical response may be characterized by complete remission of a cancer or infections. The clinical response may be determined as described herein below.

In another aspect of the invention the vaccine composition is capable of eliciting a clinical response in subject, wherein the clinical response is characterized by a decrease in the sum of the longest diameter of the largest target lesion. The decrease may be determined as described herein below.

All measurable lesions up to a maximum of five lesions per organ and 10 lesions in total, representative of all involved organs should be identified as target lesions and recorded and measured at baseline.

Target lesions should be selected on the basis of their size (lesions with the longest diameter) and their suitability for accurate repeated measurements (either by imaging techniques or clinically).

A sum of the longest diameter (LD) for all target lesions will be calculated and reported as the baseline sum LD. The baseline sum LD will be used as reference by which to characterize the objective tumor.

All other lesions (or sites of disease) should be identified as non-target lesions and should also be recorded at baseline. Measurements of these lesions are not required, but the presence or absence of each should be noted throughout follow-up.

Evaluation of Target Lesions
  Complete Response (CR): Disappearance of all target lesions
  Partial Response (PR): At least a 30% decrease in the sum of the LD of target lesions, taking as reference the baseline sum LD
  Progressive Disease (PD): At least a 20% increase in the sum of the LD of target lesions, taking as reference the smallest sum LD recorded since the treatment started or the appearance of one or more new lesions
  Stable Disease (SD): Neither sufficient shrinkage to qualify for PR nor sufficient increase to qualify for PD, taking as reference the smallest sum LD since the treatment started
Evaluation of Non-target Lesions
  Complete Response (CR): Disappearance of all non-target lesions and normalization of tumor marker level
  Incomplete Response/Stable Disease (SD): Persistence of one or more non-target lesion(s) or/and maintenance of tumor marker level above the normal limits
  Progressive Disease (PD): Appearance of one or more new lesions and/or unequivocal progression of existing non-target lesions In an embodiment of the present invention the vaccine composition comprising any of the herein mentioned proteins and/or polypeptides is capable of eliciting a clinical response in a subject, wherein the clinical response is characterized by a decrease in the sum of the longest diameter of the largest target lesion It is contemplated that the vaccine composition of the invention is capable of eliciting an immune response against a cancer expressing TDO of SEQ ID NO: 1 or a functional homologue thereof having at least 70% identity to SEQ ID NO: 1, when administered to an individual suffering from a cancer expressing TDO. The vaccine composition of the invention is capable of eliciting the production in a vaccinated individual of effector T-cells having a cytotoxic effect against the cancer cells, TDO expressing APCs and/or inducing infiltration of antigen specific T-cells in tumor stroma in a subject.

In addition to their capacity to elicit immune responses in PBL populations it is also contemplated that the peptides of the invention are capable of eliciting cytolytic immune responses in situ, i.e. in solid tumor tissues. This may for example be demonstrated by providing HLA-peptide complexes, e.g. being multimerized and being provided with a detectable label, and using such complexes for immunohistochemistry stainings to detect in a tumor tissue CTLs that are reactive with the epitope peptide of the invention. Accordingly, a further significant feature of the peptide of the invention is that it is capable of in situ detection in a tumor tissue of CTLs that are reactive with the epitope peptide.

It is also contemplated that the peptides of the invention, in addition to their capacity to bind to HLA molecules resulting in the presentation of complexes of HLA and peptides on cell surfaces, which complexes in turn act as epitopes or targets for cytolytic T cells, may elicit other types of immune responses, such as B-cell responses resulting in the production of antibodies against the complexes and/or a Delayed Type Hypersensitivity (DTH) reaction. The latter type of immune response is defined as a redness and palpable induration at the site of injection of the peptide of the invention.

It is an object of the presenting invention to provide a vaccine composition comprising Tryptophan 2,3-dioxygenase (TDO) of SEQ ID NO: 1 or a functional homologue thereof having at least 70% identity to SEQ ID NO: 1 or an immunogenically active peptide fragment comprising a consecutive sequence of said TDO or said functional homologue thereof or a nucleic acid encoding said TDO or said peptide fragment; and an adjuvant, for the prevention of, reduction of risk from or treatment of cancer.

Cancer Combination Treatment

In some cases it will be appropriate to combine the treatment method of the invention with a further cancer treatment such as chemotherapy, radiotherapy, treatment with immunostimulating substances, gene therapy, treatment with antibodies and treatment using dendritic cells.

Since elevated expression of TDO in tumor cells leads to inhibition of the immune system, the combination of a TDO-based immunotherapy as disclosed by the present invention with cytotoxic chemotherapy and or another anticancer immunotherapeutic treatment is an effective approach to treat cancer. These remedies are also referred to herein as "second active ingredients".

Examples of chemotherapeutic agents that are of relevance in regards to co-administration (sequentially or simultaneously) with the vaccine composition of the present invention include, but are not limited to: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

Another second active ingredient may be a kinase inhibitor, for separate, simultaneous or combined use in the treatment of tumors. Suitable kinase inhibitors include those which have been shown to possess anti-tumor activity (such as gefitinib (Iressa) and erlotinib (Tarceva) and these could be used in combination with the peptides. The receptor tyrosine kinase inhibitors, such as Sunitinib malate and Sorafenib which have been shown to be effective in the treatment of renal cell carcinoma are also suitable to be used as second active ingredients.

Further examples of second active ingredients are immunostimulating substances e.g. cytokines and antibodies. Such as cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In an embodiment, the vaccine composition of the present invention, comprising an TDO derived polypeptide, is administered in combination with a second active ingredient, such as an immunostimulatory substance. The immunostimulatory substance is preferably an interleukin such as IL-21 or IL-2 or a chemotherapeutic agent.

The vaccine compositions of the invention may also comprise one or more additional antigens in addition to TDO. Said antigens, may for example be immunogenically active peptides derived from cancer associated proteins.

Thus, the vaccine compositions of the invention may in addition to TDO and/or immunogenically active peptide fragments thereof also comprise one or more of the following:
1) IDO
2) An immunogenically active peptide fragment of IDO
3) A functional homologue of 1) or 2)
4) A polypeptide comprising 1), 2) or 3)
5) A nucleic acid encoding any of 1), 2), 3) or 4).

Said IDO may in particular be IDO of SEQ ID NO:1 of WO 2009/143843, IDO of SEQ ID NO:13 of WO 2009/143843, IDO of SEQ ID NO:14 of WO 2009/143843, IDO of SEQ ID NO:15 of WO 2009/143843 or IDO of SEQ ID NO:16 of WO 2009/143843. Useful immunogenically active peptide fragments of IDO, which can be contained in the vaccine compositions of the present invention are described in WO 2009/143843.

The vaccine compositions of the invention may in addition to TDO and/or immunogenically active peptide fragments thereof also comprise one or more of the following:
1) PD-L1
2) An immunogenically active peptide fragment of PD-L1
3) A functional homologue of 1) or 2)
4) A polypeptide comprising 1), 2) or 3)
5) A nucleic acid encoding any of 1), 2), 3) or 4).

Said PD-L1 may in particular be PD-L1 of SEQ ID NO:1 of WO2013/056716. Useful immunogenically active peptide fragments of PD-L1, which can be contained in the vaccine compositions of the present invention are described in WO2013/056716.

Infections

In another embodiment of the invention, the vaccine compositions disclosed herein are for treatment or prevention of an inflammatory condition.

The term "inflammatory condition" as used herein relates to any kind of clinical condition giving rise to an immune response, such as an inflammation, and therefore includes infectious diseases, chronic infections, autoimmune conditions and allergic inflammations. Thus, inflammatory conditions, such as infectious diseases, chronic infections, autoimmune conditions and allergic inflammations are all clinical conditions of relevance for the present invention, and are dealt with in turn hereunder.

Inflammation is the complex biological response of vascular tissues to harmful stimuli, such as pathogens, damaged cells, or irritants. It is a protective attempt by the organism to remove the injurious stimuli as well as initiate the healing process for the tissue. Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process. In either case, TDO is expressed by cells of the immune system such as the APCs and therefore infections and inflammations are clinical conditions that may be treated, prevented, or from which the risk may be reduced by the administration of the vaccine composition of the present invention. The vaccine composition preferably comprises TDO protein, protein fragments, polypeptide or peptides derived there from or functional homologues of any of these.

Examples of disorders associated with inflammation which are of relevance to the presenting invention include, but are not limited to: Allergic inflammations, Asthma, Autoimmune diseases, Chronic inflammations, Chronic prostatitis, Glomerulonephritis, Hypersensitivities, Infectious diseases, Inflammatory bowel diseases, Pelvic inflammatory disease, Reperfusion injury, Rheumatoid arthritis, Transplant rejection, and Vasculitis.

Chronic Inflammations

Chronic inflammation is especially of relevance in regards to the present invention. A chronic inflammation is a pathological condition characterized by concurrent active inflammation, tissue destruction, and attempts at repair. Chronically inflamed tissue is characterized by the infiltration of mononuclear immune cells (monocytes, macrophages, lymphocytes, and plasma cells), tissue destruction, and attempts at healing, which include angiogenesis and fibrosis.

In acute inflammation, removal of the stimulus halts the recruitment of monocytes (which become macrophages under appropriate activation) into the inflamed tissue, and existing macrophages exit the tissue via lymphatics. However in chronically inflamed tissue the stimulus is persistent, and therefore recruitment of monocytes is maintained, existing macrophages are tethered in place, and proliferation of macrophages is stimulated (especially in atheromatous plaques).

It is an object of the presenting invention to provide a vaccine composition comprising Tryptophan 2,3-dioxygenase (TDO) of SEQ ID NO: 1 or a functional homologue thereof having at least 70% identity to SEQ ID NO: 1 or an immunogenically active peptide fragment comprising a consecutive sequence of said TDO or said functional homologue thereof or a nucleic acid encoding said TDO or said peptide fragment; and an adjuvant, for the prevention of, reduction of risk from or treatment of chronic inflammations.

Infectious Diseases

The vaccine composition of the present invention may be used to prevent, reduce the risk from or treat a clinical condition. In a preferred embodiment of the invention, the clinical condition is an infectious disease. The infectious disease may be promoted by any infectious agent such as bacteria, virus, parasites and or fungi that are capable of inducing an increased expression of TDO in the individual suffering from the infectious disease, preferably, the infectious disease is or is at risk of becoming a chronic disease. As described in the background of invention, the increased expression of TDO has an immediate effect on the microbial agents in the vicinity of the TDO expressing organism by depriving it of tryptophan. However, this approach backfires, as the increased TDO expression induces inhibits the activity of Treg cells, if the TDO expressing cell is an APC. Therefore it is an aspect of the present invention to provide a vaccine composition comprising TDO protein, protein fragments, peptides and or variant of any of these for the treatment, amelioration of (lessening of severity) stabilization and/or prevention of a disease caused by an infectious agent.

An infectious diseases may be caused by a virus, and viral diseases against which the vaccine composition of the present invention may be administered in the treatment of include, but are not limited to the following viral diseases: HIV, AIDS, AIDS Related Complex, Chickenpox (Varicella), Common cold, Cytomegalovirus Infection, Colorado tick fever, Dengue fever, Ebola hemorrhagic fever, Hand, foot and mouth disease, Hepatitis, Herpes simplex, Herpes zoster, HPV (Human papillomavirus), Influenza (Flu), Lassa fever, Measles, Marburg hemorrhagic fever, Infectious mononucleosis, Mumps, Norovirus, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease, and Yellow fever. Preferably, the vaccine composition is administered to individuals suffering from HIV/AIDS and viral infections that may cause cancer. The main viruses associated with human cancers are human papillomavirus, hepatitis B and hepatitis C virus, Epstein-Barr virus, and human T-lymphotropic virus; thus it is an object of the present invention to be administered as the treatment of or as part of the treatment of these viral infections.

Examples of bacterial infections of relevance for the present invention include, but are not limited to: Anthrax, Bacterial Meningitis, Botulism, Brucellosis, Campylobacteriosis, Cat Scratch Disease, Cholera, Diphtheria, Epidemic Typhus, Gonorrhea, Impetigo, Legionellosis, Leprosy (Hansen's Disease), Leptospirosis, Listeriosis, Lyme disease, Melioidosis, Rheumatic Fever, MRSA infection, Nocardiosis, Pertussis (VVhooping Cough), Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus, and Urinary Tract Infections. It is an object of the present invention to provide a vaccine for the treatment and/or prevention and/or reduction of risk from a bacterial infection.

It is a further aspect of the present invention to provide a vaccine composition for the treatment and/or prevention and/or reduction of risk from: Parasitic infectious diseases such as, but not limited to: African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trichomoniasis, and Trypanosomiasis; Fungal infectious diseases such as but not limited to: Aspergillosis, Blastomycosis, Candidiasis, Coccidioidomycosis, Cryptococcosis, Histoplasmosis, Tinea pedis; Prion infectious diseases such as but not limited to: transmissible spongiform encephalopathy, Bovine spongiform encephalopathy, Creutzfeldt-Jakob disease, Kuru—Fatal Familial Insomnia, and Alpers Syndrome; thus it is an object of the present invention to be administered as the treatment of or as part of the treatment of these parasitic, fungal or prion caused infections.

Infectious Disease Combination Treatment

It is further provided for that a treatment of any infectious disease by the administration of the vaccine composition according to the present invention may be given in conjunction with a further (second) active ingredient or in combination with a further treatment such as antibiotic treatment, chemotherapy, treatment with immuno-stimulating substances, treatment using dendritic cells, antiviral agents anti parasitic agents and so forth.

Examples of a second active ingredient that may be used in the treatment of an infectious disease in combination with the vaccine of the present invention include, and are not limited to antibiotics. The term antibiotics herein refers to substances with anti-bacterial, anti-fungal, anti-viral and/or anti-parasitical activity; examples of relevance to the present invention include, but are not limited to: Amikacin, Gentamycin, Kanamycin, Neomycin, Netilmicin, Paromomycin, Streptomycin, Tobramycin, Ertapenem, Imipenem, Meropenem, Chloramphenicol, Fluoroquinolones, Ciprofloxacin, Gatifloxacin, Gemifloxacin, Grepafloxacin, Levofloxacin, Lomefloxacin, Moxifloxacin, Norfloxacin, Ofloxacin, Sparfloxacin, Trovafloxacin, Glycopeptides, Vancomycin, Lincosamides, Clindamycin, Macrolides/Ketolides, Azithromycin, Clarithromycin, Dirithromycin, Erythromycin, Cefadroxil, Cefazolin, Cephalexin, Cephalothin, Cephapirin, Cephradine, Cefaclor, Cefamandole, Cefonicid, Cefotetan, Cefoxitin, Cefprozil, Cefuroxime, Loracarbef, Cefdinir, Cefditoren, Cefixime, Cefoperazone, Cefotaxime, Cefpodoxime, Ceftazidime, Ceftibuten, Ceftizoxime, Ceftriaxone, Cefepime, Monobactams, Aztreonam, Nitroimidazoles, Metronidazole, Oxazolidinones, Linezolid, Penicillins, Amoxicillin, Amoxicillin/Clavulanate, Ampicillin, Sulbactam, Bacampicillin, Carbenicillin, Cloxacillin, Dicloxacillin, Methicillin, Mezlocillin, Nafcillin, Oxacillin, Penicillin G, Penicillin V, Piperacillin, Piperacillin/Tazobactam, Ticarcillin, Ticarcillin/Clavulanate, Streptogramins, Quinupristin, Dalfopristin, Sulfonamide/Sulfamethoxazole, Trimethoprim, Tetracyclines, Demeclocycline, Doxycycline, Minocycline, Tetracycline, Azole antifungals Clotrimazole Fluconazole, Itraconazole, Ketoconazole, Miconazole, Voriconazole, Amphotericin B, Nystatin, Echinocandin, Caspofungin, Micafungin, Ciclopirox, Flucytosine, Griseofulvin, and Terbinafine. Of further relevance are antivirals such as Vidarabine, Acyclovir, Gancyclovir and Valcyte (valganciclovir), Nucleoside-analog reverse transcriptase inhibitors (NRTI): AZT (Zidovudine), ddl (Didanosine), ddC (Zalcitabine), d4T (Stavudine), 3TC (Lamivudine), Non-nucleoside reverse transcriptase inhibitors (NNRTI): Nevirapine, Delavirdine, Protease Inhibitors: Saquinavir, Ritonavir, Indinavir, Nelfinavir, Ribavirin, Amantadine/Rimantadine, Relenza and Tamiflu, Pleconaril, Interferons In an embodiment, the present invention regards a vaccine composition comprising TDO derived proteins, polypeptides and/or functional homologs of these for the treatment of an infectious disease in combination with at least one antibiotic. Preferably, the vaccine composition of the present invention is used for the treatment of chronic infections e.g. HIV and therefore is used in combination with any of the above listed antibiotics such as anti-viral agents.

Autoimmune Diseases

Autoimmune diseases arise when an organism fails to recognize its own constituent parts (down to the sub-molecular levels) as self, which results in an immune response against its own cells and tissues. Any disease that results from such an aberrant immune response is termed an autoimmune disease and is of relevance to the present invention. Examples hereof include but are not limited to: Coeliac disease, diabetes mellitus type 1 (IDDM), systemic lupus erythematosus (SLE), Sjogren's syndrome, multiple sclerosis (MS), Hashimoto's thyroiditis, Graves' disease, idiopathic thrombocytopenic purpura, and rheumatoid arthritis (RA).

It is an object of the present invention to provide a vaccine composition comprising Tryptophan 2,3-dioxygenase (TDO) of SEQ ID NO:1 or a functional homologue thereof having at least 70% identity to SEQ ID NO: 1 or an immunogenically active peptide fragment comprising a consecutive sequence of said TDO or said functional homologue thereof or a nucleic acid encoding said TDO or said peptide fragment; and an adjuvant, for the prevention of, reduction of risk from or treatment of autoimmune diseases.

Autoimmune Disease Combination Treatment

Current treatments for autoimmune disease are usually immunosuppressive, anti-inflammatory, or palliative. Non-immune therapies, such as hormone replacement in Hashimoto's thyroiditis or diabetes mellitus Type 1 treatment outcomes of the auto-aggressive response. Dietary manipulation limits the severity of celiac disease. Steroidal or NSAID treatment limits inflammatory symptoms of many diseases. Intravenous preparations of immune globulin (IVIG) are used for Chronic Inflammatory Demyelinating Polyneuropathy (CIDP) and Guillain-Barré syndrome (GBS). More specific immunomodulatory therapies, such as the TNFα antagonist Etanercept, have been shown to be useful in treating RA. These immunotherapies may be associated with increased risk of adverse effects, such as susceptibility to infection.

Helminthic therapy has developed based on these observations and involves inoculation of the individual with specific parasitic intestinal nematodes (helminths).

There are currently two closely-related treatments available, inoculation with either Necator americanus, commonly known as hookworms, or Trichuris Suis Ova, commonly known as Pig Whipworm Eggs. Research is available that demonstrates this approach is highly effective in treating a variety of autoimmune disorders, including Crohn's, Ulcerative Colitis, Asthma, allergies, Multiple Sclerosis, and chronic inflammatory disorders In an embodiment, the vaccine herein disclosed is used in combination with a second active ingredient such as any of the above mentioned drugs and treatments against autoimmune diseases.

Allergic Inflammation

Allergy is a disorder of the immune system often also referred to as atopy. Allergic reactions occur to environmental substances known as allergens; these reactions are acquired, predictable and rapid. Strictly, allergy is one of four forms of hypersensitivity and is called type I (or immediate) hypersensitivity. It is characterized by excessive activation of certain white blood cells called mast cells and basophils by a type of antibody, known as IgE, resulting in an extreme inflammatory response. Common allergic reactions include eczema, hives, hay fever, asthma, food allergies, and reactions to the venom of stinging insects such as wasps and bees.

Allergic inflammation is an important pathophysiological feature of several disabilities or medical conditions including allergic asthma, atopic dermatitis, allergic rhinitis and several ocular allergic diseases.

It is an object of the present invention to provide a vaccine composition comprising Tryptophan 2,3-dioxygenase (TDO) of SEQ ID NO: 1 or a functional homologue thereof having at least 70% identity to SEQ ID NO: 1 or an immunogenically active peptide fragment comprising a consecutive sequence of said TDO or said functional homologue thereof or a nucleic acid encoding said TDO or said peptide fragment; and an adjuvant, for the prevention of, reduction of risk from or treatment of allergic inflammation.

Allergic Inflammation Combination Treatment

Two types of treatments are available for the treatment of allergic inflammations, pharmacotherapy and immunotherapy: pharmacotherapy and immunotherapy.

Pharmacotherapy, is the use of antagonistic drugs to block the action of allergic mediators, or to prevent activation of cells and degranulation processes. These include antihistamines, cortisone, dexamethasone, hydrocortisone, epinephrine (adrenaline), theophylline, cromolyn sodium and anti-leukotrienes, such as Montelukast (Singulair) or Zafirlukast (Accolate); anti-cholinergics, decongestants, mast cell stabilizers, and other compounds thought to impair eosinophil chemotaxis, are also commonly used.

Immunotherapy is the desensitization or hyposensitization treatment in which the individual is gradually vaccinated with progressively larger doses of the allergen in question. A second form of immunotherapy involves the intravenous injection of monoclonal anti-IgE antibodies. A third type, Sublingual immunotherapy, is an orally-administered therapy which takes advantage of oral immune tolerance to non-pathogenic antigens such as foods and resident bacteria.

In an embodiment, the vaccine herein disclosed is used in combination with a second active ingredient such as any of the above mentioned drugs and treatments against allergic inflammations.

Pharmaceutical Compositions

The present invention regards pharmaceutical compositions capable of treating, reducing the risk of and/or preventing a clinical disorder associated with TDO expression in an individual. Said pharmaceutical composition may in particular be a vaccine composition. The vaccine compositions of the present invention may be "traditional" vaccine compositions comprising antigens such as proteins polypeptides and/or nucleic acid molecules. They may also be in the form of compositions comprising cells, such as modified cells originating from the individual and later processed, or to compositions comprising complex molecules such as antibodies or TCRs.

Generally, a vaccine is a substance or composition capable of inducing an immune response in an individual. The composition may comprise one or more of the following: an "active component" such as an antigen(s) (e.g. protein, polypeptides, peptides, nucleic acids and the like), nucleic acid constructs comprising one or more antigens amongst other elements, cells, (e.g. loaded APC or T cells for adoptive transfer), complex molecules (Antibodies, TCRs and MHC complexes and more), carriers, adjuvants and pharmaceutical carriers. In the following, the various components of a vaccine composition according to the present invention are disclosed in more detail.

The vaccine composition of the invention is capable of eliciting an immune response against a cancer, DC or APC expressing TDO of SEQ ID NO: 1 or a functional homologue thereof having at least 70% identity to SEQ ID NO 1, when administered to an individual suffering from a cancer and/or infection (leading to the expression of TDO). In a preferred embodiment the clinical condition is a cancer. The vaccine composition of the invention is capable of eliciting the production in a vaccinated individual of effector T-cells having a cytotoxic effect against cancer cells, APCs and DCs expressing TDO and/or inducing infiltration of antigen specific T-cells in tumor stroma in a subject.

Antigens and Other Active Components

Protein/Polypeptide Based Vaccine Compositions

Figure 2A:
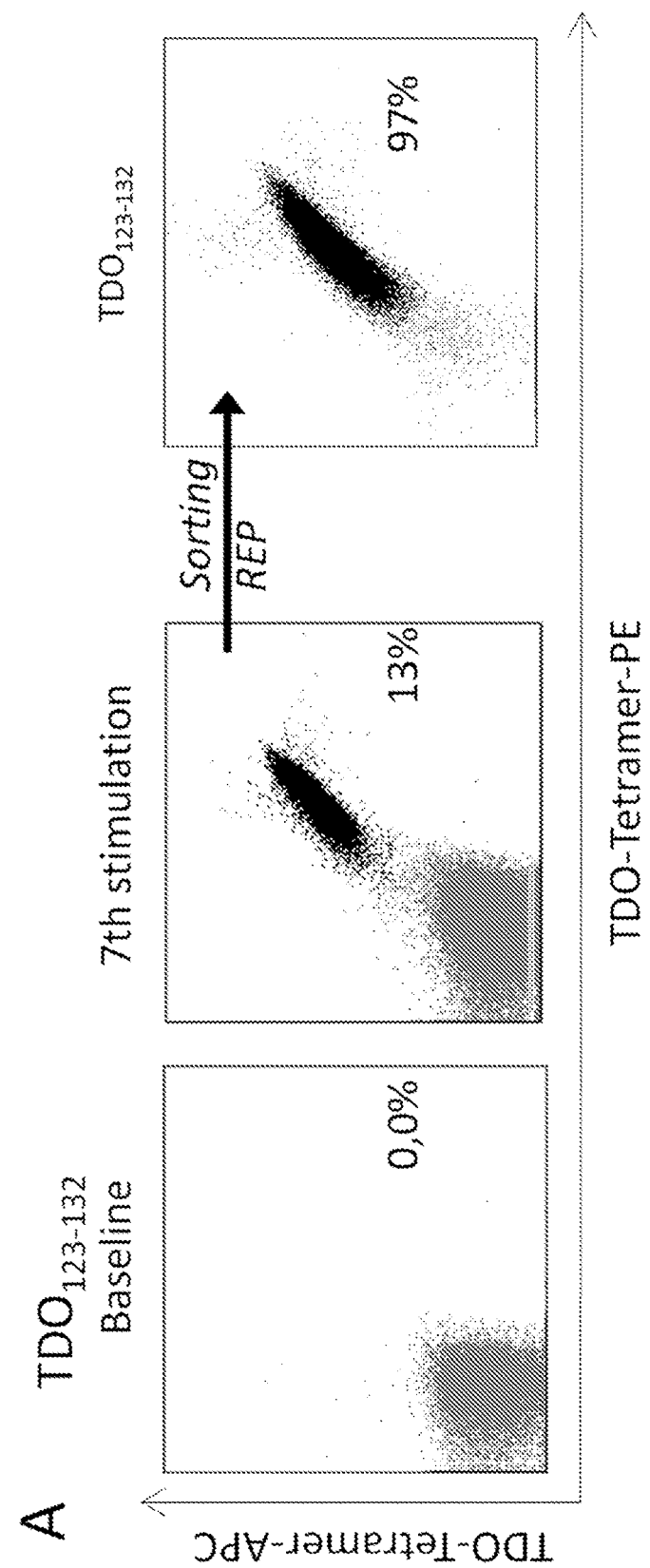
FIG. 2 shows expansion of TDO-specific CD8$^+$ T cells. Tetramer analysis of TDO-specific T-cells; Examples of $TDO_{123-132}$-(A) or $TDO_{309-317}$ (B) -specific CD8$^+$ T-cells among PBMC from a breast cancer patient (BC1) as visualised by flow cytometry staining using the tetramers HLA-A2/$TDO_{123-132}$-PE, HLA-A2/$TDO_{123-132}$-APC. The stainings were performed directly ex vivo (left), after peptide stimulations in vitro (middle), and after sorting and expansion of tetramer-positive cells by FACS (right).
Figure 2B:
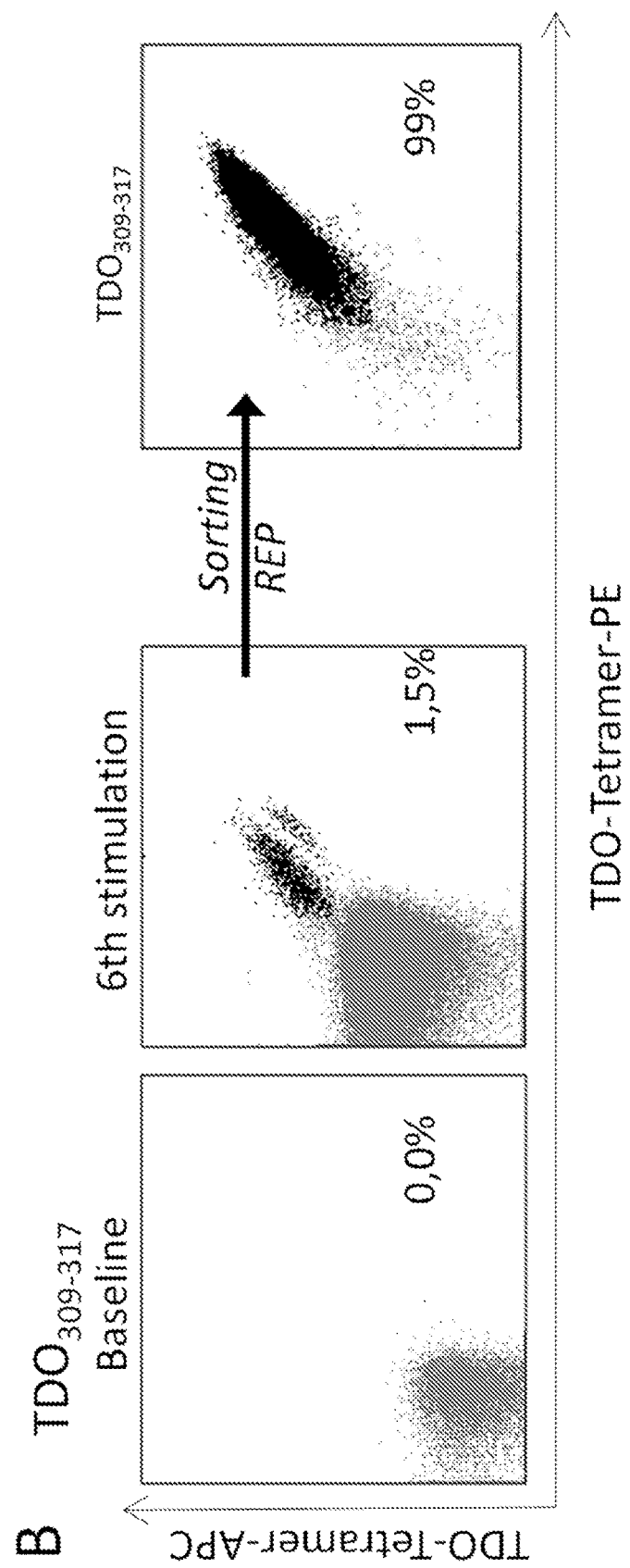

The peptides of the present invention bind with surprisingly high affinity (see FIG. 2) and are ready for use as antigens as they are presented here. Preferably, the vaccine composition of the present invention comprises one or more of the following:

1) Tryptophan 2,3-dioxygenase (TDO), which may be any of the TDOs described herein below in the section "Tryptophan 2,3-dioxygenase";
2) An immunogenically active peptide fragment of TDO comprising a consecutive sequence of amino acids of TDO, which may be any of the peptides described herein below in the section "Immunogenically active peptide fragment of TDO".
3) An immunogenically active peptide fragments of TDO, which is an MHC Class I-restricted peptide fragment or MHC Class II-restricted peptide fragment, such as any of the an MHC Class I-restricted peptide fragments or MHC Class II-restricted peptide fragments described in the section "MHC";
4) A functional homologue of the polypeptides under 1), 2) and 3);
5) A polypeptide comprising any of polypeptides under 1), 2), 3) and 4), which may be any of the polypeptides described herein below in the section "Polypeptides comprising TDO or a fragment thereof";
6) A nucleic acid encoding any of the polypeptides under 1), 2), 3) and 4).

The choice of antigen in the vaccine composition of the invention will depend on parameters determinable by the person of skill in the art. As it has been mentioned, each of the different peptides of the invention is presented on the cell surfaces by a particular HLA molecule. As such, if a subject to be treated is typed with respect to HLA phenotype, a peptide/peptides are selected that is/are known to bind to that particular HLA molecule. Alternatively, the antigen of interest is selected based on the prevalence of the various HLA phenotypes in a given population. As an example, HLA-A2 is the most prevalent phenotype in the Caucasian population, and therefore, a composition containing a peptide binding to HLA-A2 will be active in a large proportion of that population. Furthermore, the antigens/peptides of the present invention may be modified according to the anchor residue motifs presented in Table 2, to enhance binding to particular HLA molecules.

The composition of the invention may also contain a combination of two or more immunogenically active peptide fragments of TDO, e.g. any of the peptides described in the sections "Immunogenically active peptide fragments of TDO", "Polypeptides comprising TDO or a fragment thereof" and "MHC". Said immunogenically active peptide fragments of TDO may each interact specifically with a different HLA molecule so as to cover a larger proportion of the target population. Thus, as examples, the pharmaceutical composition may contain a combination of a peptide restricted by a HLA-A molecule and a peptide restricted by a HLA-B molecule, e.g. including those HLA-A and HLA-B molecules that correspond to the prevalence of HLA phenotypes in the target population, such as e.g. HLA-A2 and HLA-B35. Additionally, the composition may comprise a peptide restricted by an HLA-C molecule.

In the case of peptide-based vaccines, epitopes can be administered in an 'MHC-ready' form, which enables presentation through exogenous loading independently of antigen uptake and processing by host antigen-presenting cells. The peptides of the present invention comprise both peptides in a short 'MHC-ready' form and in a longer form requiring processing by the proteasome thus providing a more complex vaccine composition that can target multiple tumor antigens. The more different HLA groups are targeted by a vaccine, the higher likelihood of the vaccine functioning in diverse populations.

Multi Epitope Vaccine Composition

The invention also relates to highly immunogenic multi-epitope vaccines. Preferably, such vaccines should be designed so as to facilitate a simultaneous delivery of the best-suited immunogenically active peptide fragments of TDO optionally in combination with other suitable peptides and/or adjuvants as described hereinafter. The present invention encompasses such multiepitope vaccines comprising immunogenically active peptide fragments of TDO optionally in combination with further proteins or peptides fragments not belonging to or derived from TDO and/or adjuvants as described hereinafter. An important factor driving the development of vaccines having a more complex composition is the desire to target multiple tumor antigens e.g. by designing vaccines comprising or encoding a collection of carefully selected CTL and $T_h$ cell epitopes. The invention thus in one aspect relates to vaccine compositions comprising both Class I and Class II-restricted TDO epitopes.

The peptides of the present invention thus comprise both peptides in a short 'MHC-ready' form (class I restricted), and in a longer form requiring processing by the proteasome (class II restricted). Thus, the composition according to the present invention may be provided as a multiepitope vaccine comprising class I restricted epitope and/or class II restricted epitopes as defined hereinbefore.

Nucleic Acid Based Vaccine Composition

The vaccine composition according to the present invention may comprise a nucleic acid encoding a TDO polypeptide or an immunologically active peptide fragment thereof. Said nucleic acid may thus encode any of the above-mentioned proteins and peptide fragments. The nucleic acid may for example be DNA, RNA, LNA, HNA, PNA, preferably the nucleic acid is DNA or RNA.

The nucleic acids of the invention may be comprised within any suitable vector, such as an expression vector. Numerous vectors are available and the skilled person will be able to select a useful vector for the specific purpose. The vector may, for example, be in the form of a plasmid, cosmid, viral particle or artificial chromosome. The appropriate nucleic acid sequence may be inserted into the vector by a variety of procedures, for example, DNA may be inserted into an appropriate restriction endonuclease site(s) using techniques well known in the art. Apart from the nucleic acid sequence according to the invention, the vector may furthermore comprise one or more of a signal sequence, an origin of replication, one or more marker genes, an enhancer element, a promoter, and a transcription termination sequence. The vector may also comprise additional sequences, such as enhancers, poly-A tails, linkers, polylinkers, operative linkers, multiple cloning sites (MCS), STOP codons, internal ribosomal entry sites (IRES) and host homologous sequences for integration or other defined elements. Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989). The vector is preferably an expression vector, comprising the nucleic acid operably linked to a regulatory nucleic acid sequence directing expression thereof in a suitable cell. Within the scope of the present invention said regulatory nucleic acid sequence should in general be capable of directing expression in a mammalian cell, preferably a human cell, more preferably in an antigen presenting cell.

In one preferred embodiment the vector is a viral vector. The vector may also be a bacterial vector, such as an attenuated bacterial vector. Attenuated bacterial vectors may be used in order to induce lasting mucosal immune responses at the sites of infection and persistence. Different recombinant bacteria may be used as vectors, for example the bacterial vector may be selected from the group consisting of *Salmonella, Lactococcus*], and Listeria. In general, induction of immunity to the heterologous antigen HPV16 L1 or E7 could be shown, with strong CTL induction and tumor regression in mice. The vector may furthermore comprise a nucleic acid encoding a T-cell stimulatory polypeptide.

Loaded APCs

In useful embodiments an immunogenic response directed against a cancer disease is elicited by administering the peptide of the invention either by loading MHC class I or class II molecules on antigen presenting cells (APCs) from the individual, by isolating PBLs from the individual and incubating the cells with the peptide prior to injecting the cells back into the individual or by isolating precursor APCs from the individual and differentiating the cells into professional APCs using cytokines and antigen before injecting the cells back into the individual.

It is thus an aspect of the invention to provide vaccine compositions comprising antigen presenting cells comprising TDO or an immunologically active peptide fragment thereof or a nucleic acid encoding said protein or said immunologically active peptide fragment. The antigen presenting cell may be any cell capable of presenting an antigen to a T-cell. Preferred antigen presenting cells are dendritic cells. The dendritic cells (DC) may be prepared and used in therapeutic procedure according to any suitable protocol, for example as described herein below. It will be appreciated by the person skilled in the art that the protocol may be adopted to use with individuals with different HLA type and different diseases.

Dendritic cells (DC) may be pulsed with 50 µg/ml HLA-restricted peptide (synthesized at GMP quality) for 1 h at 37° C. peptide and $5 \times 10^6$ cells are administered sub-cutaneously at day 1 and 14, subsequently every 4 weeks, additional leukapheresis after 5 vaccinations. The generation of DC for clinical use and quality control can be performed essentially as described in Nicolette et al., (2007).

Thus, in one embodiment of the present invention, a method for treating an individual suffering from a clinical condition characterized by the expression of TDO, preferably wherein the clinical condition is cancer or an infection, is one wherein the peptide is administered by presenting the peptide to the individual's antigen presenting cells (APCs) ex vivo followed by injecting the thus treated APCs back into the individual. There are at least two alternative ways of performing this. One alternative is to isolate APCs from the individual and incubate (load) the MHC class I molecules with the peptide. Loading the MHC class I molecules means incubating the APCs with the peptide so that the APCs with MHC class I molecules specific for the peptide will bind the peptide and therefore be able to present it to T cells. Subsequently, the APCs are re-injected into the individual. Another alternative way relies on the recent discoveries made in the field of dendritic cell biology. In this case, monocytes (being dendritic cell precursors) are isolated from the individual and differentiated in vitro into professional APC (or dendritic cells) by use of cytokines and antigen. Subsequently, the in vitro generated DCs are pulsed with the peptide and injected into the individual.

Adoptive Immunotherapy/Adoptive Transfer

An important aspect the invention relates to cultivating TDO specific T-cells in vitro and adoptive transfer of these to individuals. Adoptive transfer means that the physician directly transfers the actual components of the immune system that are already capable of producing a specific immune response, into an individual.

It is one objective to the present invention to provide TDO specific T-cells, which may be useful for example for adoptive transfer. Isolated T-cells comprising T-cell receptors capable of binding specifically to TDO peptide/MHC class I or TDO peptide/MHC class II complexes can be adoptively transferred to individuals, said T-cells preferably being T-cells that have been expanded in vitro, wherein the TDO peptide may be any of the immunogenically active peptide fragments of TDO mentioned herein above. Methods of expanding T-cells in vitro are well known to the skilled person. The invention also relates to methods of treatment comprising administering T-cells comprising T-cell receptors capable of binding specifically to a MHC-restricted TDO peptide complex to an individual, such as a human being suffering from a cancer disease, wherein the TDO derived peptide may be any of the TDO peptides mentioned herein above. The invention furthermore relates to use of T-cells comprising T-cell receptors capable of binding specifically to TDO or peptide fragments thereof for the preparation of a medicament for the treatment of a cancer or infection. Autologous T-cell transfer may be performed essentially as described in Walter et al., (1995).

TCR Transfer

In yet another embodiment, such T-cells could be irradiated before adoptive transfer to control proliferation in the individual. It is possible to genetically engineer the specificity of T cells by TCR gene transfer (Engels et al., 2007). This allows the transfer of T cells bearing TDO peptide specificity into individuals. In general, the use of T cells for adoptive immunotherapy is attractive because it allows the expansion of T cells in a tumor- or virus-free environment, and the analysis of T cell function prior to infusion. The application of TCR gene-modified T cells (such as T-cells transformed with an expression construct directing expressing of a heterologous TCR) in adoptive transfer has several advantages in comparison to the transfer of T cell lines: (i) the generation of redirected T cells is generally applicable. (ii) High-affinity or very high-affinity TCRs can be selected or created and used to engineer T cells. (iii) High-avidity T cells can be generated using codon optimized or murinized TCRs allowing better surface expression of the stabilized TCRs. Genetic engineering of T cell specificity by T cell receptor (TCR) gene transfer may be performed essentially as described in Morgan et al., (2006).

TCR Transfection

TCR with known anti-tumor reactivity can be genetically introduced into primary human T lymphocytes. Genes encoding TCR alpha and beta chains from a tumor specific CTL clone can be transfected into primary T cells and in this way reprogram T cells with specificity against the tumor antigen. TCR RNA is transfected into PBL by electroporation (Schaft et al., 2006). Alternatively, T cells can be provided with at new specificity by TCR gene transfer using retroviral vectors (Morgan et al., 2006). However, the provirus from the retroviral vector might integrate at random in the genome of the transfected cells and subsequently disturb cell growth. Electroporation of T cells with TCR-coding RNA overcome this disadvantage, since RNA is only transiently present in the transfected cells and cannot be integrated in the genome (Schaft et al., 2006). Furthermore, transfection of cells is routinely used in the laboratory.

Adjuvants and Carriers

The vaccine composition according to the invention preferably comprises an adjuvant and/or a carrier. Examples of useful adjuvants and carriers are given herein below. Thus the TDO polypeptide, the immunogenically active peptide fragments of TDO or functional homologues thereof, the polypeptides comprising same or nucleic acid encoding same may in a composition of the present invention be associated with an adjuvant and/or a carrier.

Adjuvants are any substance whose admixture into the vaccine composition increases or otherwise modifies the immune response to the TDO or to immunogenically active peptide fragments of TDO, see further in the below. Carriers are scaffold structures, for example a polypeptide or a polysaccharide, to which the TDO or peptide fragment thereof is capable of being associated and which aids in the presentation of especially the peptides of the present invention.

Many of the peptides of the invention are relatively small molecules and it may therefore be required in compositions as described herein to combine the peptides with various materials such as adjuvants and/or carriers, to produce vaccines, immunogenic compositions, etc. Adjuvants, broadly defined, are substances which promote immune responses. A general discussion of adjuvants is provided in Goding, Monoclonal Antibodies: Principles & Practice (2nd edition, 1986) at pages 61-63. Goding notes, that when the antigen of interest is of low molecular weight, or is poorly immunogenic, coupling to an immunogenic carrier is recommended. Examples of such carrier molecules include keyhole limpet haemocyanin, bovine serum albumin, ovalbumin and fowl immunoglobulin. Various saponin extracts have also been suggested to be useful as adjuvants in immunogenic compositions. It has been proposed to use granulocyte-macrophage colony stimulating factor (GM-CSF), a well-known cytokine, as an adjuvant (WO 97/28816).

A carrier may be present independently of an adjuvant. The function of a carrier can for example be to increase the molecular weight of in particular peptide fragments in order to increase their activity or immunogenicity, to confer stability, to increase the biological activity, or to increase serum half-life. Furthermore, a carrier may aid in presenting the TDO protein, polypeptide, functional homologue or peptide fragments thereof to T-cells. The carrier may be any suitable carrier known to a person skilled in the art, for example a protein or an antigen presenting cell. A carrier protein could be, but is not limited to, keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diptheria toxoid are suitable carriers in one embodiment of the invention. Alternatively, the carrier may be dextrans for example sepharose.

Thus it is an aspect of the present invention that the TDO protein, polypeptide fragment, variant or peptide derived here from present in the composition is associated with a carrier such as e.g. a protein of the above or an antigen-presenting cell such as e.g. a dendritic cell (DC).

Adjuvants could for example be selected from the group consisting of: $AlK(SO_4)_2$, $AlNa(SO_4)_2$, $AlNH_4 (SO_4)$, silica, alum, $Al(OH)_3$, $Ca_3 (PO_4)_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2% squalene/Tween-80. ®. emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from Mycobacterium, tuberculosis, substances found in Corynebacterium parvum, Bordetella pertussis, and members of the genus Brucella, Titermax, ISCOMS, Quil A, ALUN (see U.S. Pat. Nos. 58767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Preferred adjuvants to be used with the invention include oil/surfactant based adjuvants such as Montanide adjuvants (available from Seppic, Belgium), preferably Montanide ISA-51. Other preferred adjuvants are bacterial DNA based adjuvants, such as adjuvants including CpG oligonucleotide sequences. Yet other preferred adjuvants are viral dsRNA based adjuvants, such as poly I:C. Imidazochinilines are yet another example of preferred adjuvants. The most preferred adjuvants are adjuvants suitable for human use.

Montanide adjuvants (all available from Seppic, Belgium), may be selected from the group consisting of Montanide ISA-51, Montanide ISA-50, Montanide ISA-70, Montanide ISA-206, Montanide ISA-25, Montanide ISA-720, Montanide ISA-708, Montanide ISA-763A, Montanide ISA-207, Montanide ISA-264, Montanide ISA-27, Montanide ISA-35, Montanide ISA 51F, Montanide ISA 016D and Montanide IMS, preferably from the group consisting of Montanide ISA-51, Montanide IMS and Montanide ISA-720, more preferably from the group consisting of Montanide ISA-51. Montanide ISA-51 (Seppic, Inc.) is oil/surfactant based adjuvants in which different surfactants are combined with a non-metabolizable mineral oil, a metabolizable oil, or a mixture of the two. They are prepared for use as an emulsion with an aqueous solution comprising TDO or peptide fragment thereof. The surfactant is mannide oleate. QS-21 (Antigenics; Aquila Biopharmaceuticals, Framingham, Mass.) is a highly purified, water-soluble saponin that handles as an aqueous solution. QS-21 and Montanide ISA-51 adjuvants can be provided in sterile, single-use vials.

The well-known cytokine GM-CSF is another preferred adjuvant of the present invention. GM-CSF has been used as an adjuvant for a decade and may preferably be GM-CSF as described in WO 97/28816.

Desirable functionalities of adjuvants capable of being used in accordance with the present invention are listed in the below table.

TABLE 3

Modes of adjuvant action

| Action | Adjuvant type | Benefit |
| --- | --- | --- |
| 1. Immunomodulation | Generally small molecules or proteins which modify the cytokine network | Upregulation of immune response. Selection of Th1 or Th2 |
| 2. Presentation | Generally amphipathic molecules or complexes which interact with immunogen in its native conformation | Increased neutralizing antibody response. Greater duration of response |
| 3. CTL induction | Particles which can bind or enclose immunogen and which can fuse with or disrupt cell membranes | Cytosolic processing of protein yielding correct class 1 restricted peptides |
| | w/o emulsions for direct attachment of peptide to cell surface MHC-1 | Simple process if promiscuous peptide(s) known |
| 4. Targeting | Particulate adjuvants which bind immunogen. Adjuvants which saturate Kupffer cells | Efficient use of adjuvant and immunogen |
| | Carbohydrate adjuvants which target lectin receptors on macrophages and DCs | As above. May also determine type of response if targeting selective |
| 5. Depot Generation | w/o emulsion for short term | Efficiency |
| | Microspheres or nanospheres for long term | Potential for single-dose vaccine |

Source: Cox, J. C., and Coulter, A. R. (1997). Vaccine 15, 248-56.

A vaccine composition according to the present invention may comprise more than one adjuvant. Furthermore, the invention encompasses a therapeutic composition further comprising any adjuvant substance and/or carrier including any of the above or combinations thereof. It is also contemplated that the TDO protein, variants or peptide fragments thereof, and the adjuvant can be administered separately in any appropriate sequence. Preferably, the vaccine compositions of the present invention comprise a Montanide adjuvant such as Montanide ISA 51 or Montanide ISA 720 or the GM-CSF adjuvant.

Accordingly, the invention encompasses a therapeutic composition further comprising an adjuvant substance including any of the above or combinations thereof. It is also contemplated that the antigen, i.e. the peptide of the invention and the adjuvant can be administered simultaneously or separately in any appropriate sequence.

Dosis and Administration

The amount of TDO or the immunogenically active peptide fragments of TDO of the invention in the vaccine composition may vary, depending on the particular application. However, a single dose of the peptide composition is preferably anywhere from about 10 μg to about 5000 μg, more preferably from about 50 μg to about 2500 μg such as about 100 μg to about 1000 μg. In particular, in embodiments of the invention where the individual to be treated is a human being, then a single dose may be in the range of 50 µg to 500 µg, for example in the range of 80 µg to 300 µg, such as in the range of 100 µg to 250 µg of TDO or said immunogenically active peptide fragment of TDO. Frequently, the vaccine compositions are administered repeatedly over time. For example the vaccine composition may be administered at least 2 times, preferably at least 5 times, more preferably at least 10 times, such as in the range of 10 to 20 times. The vaccine composition may also be administered continuously. Administration may be repeated at any useful frequency. Thus, for example the vaccine compositions may be administered once every week, such as once every two weeks, for example once every 3 weeks, such as once per month, for example once per two months, such as once per three months, for example once per half year, such as once per year. In particular, the vaccine compositions may be administered continuously. The frequency of administration may alter during said time. In one embodiment the vaccine compositions are administered continuously once per 1 to 3 months. Modes of administration include intradermal, subcutaneous and intravenous administration, implantation in the form of a time release formulation, etc. Any and all forms of administration known to the art are encompassed herein. Also any and all conventional dosage forms that are known in the art to be appropriate for formulating injectable immunogenic peptide composition are encompassed, such as lyophilized forms and solutions, suspensions or emulsion forms containing, if required, conventional pharmaceutically acceptable carriers, diluents, preservatives, adjuvants, buffer components, etc.

The pharmaceutical compositions may be prepared and administered using any conventional protocol known by a person skilled in the art. In examples 3-5 non-limiting examples of preparation of a vaccine composition according to the invention is given as well as a non-limiting example of administration of such as a vaccine. It will be appreciated by the person skilled in the art that the protocol may be easily adapted to any of the vaccine compositions described herein. In a further embodiment of the invention, the pharmaceutical composition of the invention is useful for treating an individual suffering from a clinical condition characterized by expression of TDO, such as cancer and infections.

The immunoprotective effect of the composition of the invention can be determined using several approaches known to those skilled in the art. A successful immune response may also be determined by the occurrence of DTH reactions after immunization and/or the detection of antibodies specifically recognizing the peptide(s) of the vaccine composition.

Vaccine compositions according to the invention may be administered to an individual in therapeutically effective amounts. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the methods of prophylaxis and treatment with the vaccine composition.

For example, the vaccine compositions can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the vaccine, comprising any of the herein described compounds can be employed as a prophylactic or therapeutic agent. Also any and all conventional dosage forms that are known in the art to be appropriate for formulating injectable immunogenic peptide composition are encompassed, such as lyophilized forms and solutions, suspensions or emulsion forms containing, if required, conventional pharmaceutically acceptable carriers, diluents, preservatives, adjuvants, buffer components, etc.

Preferred modes of administration of the vaccine composition according to the invention include, but are not limited to systemic administration, such as intravenous or subcutaneous administration, intradermal administration, intramuscular administration, intranasal administration, oral administration, rectal administration, vaginal administration, pulmonary administration and generally any form of mucosal administration. Furthermore, it is within the scope of the present invention that the means for any of the administration forms mentioned in the herein are included in the present invention.

A vaccine according to the present invention can be administered once, or any number of times such as two, three, four or five times. Administering the vaccine more than once has the effect of boosting the resulting immune response. The vaccine can further be boosted by administering the vaccine in a form or body part different from the previous administration. The booster shot is either a homologous or a heterologous booster shot. A homologous booster shot is a where the first and subsequent vaccinations comprise the same constructs and more specifically the same delivery vehicle especially the same viral vector. A heterologous booster shot is where identical constructs are comprised within different viral vectors.

Second Active Ingredient

It is an aspect of the present invention that the vaccine composition herein provided is used in combination with a second active ingredient. The administration of the vaccine composition and the second active ingredient may be sequential or combined. Examples of second active ingredients are given above for both cancers and infections. It is a further aspect that the vaccine composition may be used in combination with other therapy of relevance for the given clinical condition to be treated. Such therapy may include surgery, chemotherapy or gene therapy, immunostimulating substances or antibodies; a person skilled in the art is able to determine the appropriate combination treatment for a given scenario.

In some cases it will be appropriate to combine the treatment method of the invention with a further medical treatment such as chemotherapy, radiotherapy, treatment with immunostimulating substances, gene therapy, treatment with antibodies and/or antibiotics and treatment using dendritic cells.

Diagnostic and Prognostic Tools

The peptides of the present invention provide the basis for developing widely applicable diagnostic and prognostic procedures in respect of cancer diseases and infections. Thus, in other useful embodiments the composition of the invention is a composition for ex vivo or in situ diagnosis of the presence of TDO expressing cells in an individual. The diagnostic procedure is based on the detection of TDO reactive T cells among PBLs or in tumor tissue.

Accordingly, there is provided a diagnostic kit for ex vivo or in situ diagnosis of the presence in an individual of TDO reactive T cells among PBLs or in tumour tissue comprising one or more peptides of the invention, and a method of detecting in an individual the presence of such reactive T cells, the method comprising contacting a tumour tissue or a blood sample with a complex of a peptide of the invention and a Class I or Class II HLA molecule or a fragment of such molecule and detecting binding of the complex to the tissue or the blood cells. In one aspect, the invention provides a complex of a peptide of the invention and a Class I or Class II HLA molecule or a fragment of such molecule, which is useful as a diagnostic reagent such as it is described herein. Such a complex may be monomeric or multimeric.

Another useful diagnostic or prognostic approach is based on generating antibodies in a heterologous animal species, e.g. murine antibodies directed against a human immunogenically active peptide fragments of TDO of the invention, which can then be used, e.g. to diagnose for the presence of cancer cells presenting the peptide. For such immunization purposes, the amount of peptide may be less than that used in the course of in vivo therapy, such as that mentioned above. In general, a preferred dose can range from about 1 μg to about 750 μg of peptide. It is also possible to produce monoclonal antibodies based on immunization with a peptide of the invention.

Accordingly, the present invention also relates to a molecule, in particular a monoclonal or polyclonal antibody including a fragment hereof, that is capable of binding specifically to a peptide of the invention and to a molecule that is capable of blocking such a binding, e.g. an antibody raised against the monoclonal or polyclonal antibody directed against a peptide of the invention. The invention furthermore relates to isolated T-cell receptors capable of binding specifically to a peptide or a protein of the invention as well as to isolated nucleic acids encoding same. Such T-cell receptors may for example be cloned from protein or peptide specific T-cells using standard techniques well known to the skilled person.

In one aspect the invention also relates to isolated T-cells comprising T-cell receptors capable of binding specifically to TDO and/or peptide fragments thereof described herein. The isolated T-cells may be CD8 T-cells or CD4 T-cells. The isolated T-cells are preferably T-cells that have been expanded in vitro. Methods of expanding T-cells in vitro are well known to the skilled person. Such T-cells may in particular be useful in the treatment of cancer by adaptive transfer or autologous cell transfer. Thus, the invention also relates to pharmaceutical compositions comprising T-cells as well as methods of treatment comprising administering T-cells comprising T-cell receptors capable of binding specifically to TDO or peptide fragments thereof to an individual, in need thereof such as an individual suffering from cancer and/or infections. Autologous cell transfer may be performed essentially as described in Walter et al., (1995).

The present invention provides the means for treating, preventing, alleviating or curing a clinical condition characterized by expression of TDO such as cancers and infections preferably a cancer, comprising administering to an individual suffering from the disease an effective amount of a composition as defined herein, a molecule that is capable of binding specifically to a peptide fragment, which may for example be an antibody or a T-cell receptor or the kit-of-parts described herein. Accordingly, it is a further aspect of the invention to provide a method of treating a clinical condition associated with the expression of TDO of SEQ ID NO: 1. Said clinical condition may e.g. be cancer or an inflammatory condition.

Monitoring Immunization

In preferred embodiments, the pharmaceutical composition of the invention is a vaccine composition. It is therefore of interest, and an aspect of the present invention to monitor the immunization in an individual to whom the vaccine composition of the present invention is administered. The pharmaceutical composition may thus be an immunogenic composition or vaccine capable of eliciting an immune response to a cancer and/or infection. As used herein, the expression "immunogenic composition or vaccine" refers to a composition eliciting at least one type of immune response directed against TDO expressing cells such as cancer cells, APCs or DCs. Thus, such an immune response may be any of the following: A CTL response where CTLs are generated that are capable of recognizing the HLA/peptide complex presented on cell surfaces resulting in cell lysis, i.e. the vaccine elicits the production in the vaccinated subject of effector T-cells having a cytotoxic effect against the cancer cells; a B-cell response giving rise to the production of anti-cancer antibodies; and/or a DTH type of immune response. It is on object of the present invention to monitor the immunization of an individual by monitoring any of the above reactions subsequent to administering the composition of the present invention to said individual.

In one aspect the invention relates to methods of monitoring immunization, said method comprising the steps of
  i) providing a blood sample from an individual
  ii) providing TDO or a peptide fragment hereof, wherein said protein or peptide may be any of the proteins or peptides described herein
  iii) determining whether said blood sample comprises antibodies or T-cells comprising T-cell receptors specifically binding the protein or peptide
  iv) thereby determining whether an immune response to said protein or peptide has been raised in said individual.

The individual is preferably a human being, for example a human being that has been immunized with TDO or immunogenically active peptide fragments of TDO or a nucleic acid encoding said protein or peptide.

Kit of Parts

The invention also relates to a kit-of-parts comprising
  any of the vaccine compositions described herein and/or
  an TDO protein or functional homologue hereof and/or
  any of the immunogenically active peptide fragments of TDO, functional homologues hereof, and/or peptides derived here from as described herein and/or
  any of the nucleic acids encoding the proteins of the above two bullet points and instructions on how to use the kit of parts.

The invention also relates to a kit-of-parts comprising
  any of the vaccine compositions described herein and/or
  an TDO protein or functional homologue hereof and/or
  any of the immunogenically active peptide fragments of TDO, functional homologues hereof, and/or peptides derived here from as described herein and/or any of the nucleic acids encoding the proteins of the above two bullet points and a second active ingredient.

Preferably, the second active ingredient is chosen in correspondence with the clinical condition to be treated so that in the case where a cancer is to be treated the second active ingredient is chosen among e.g. chemotherapeutic agents as listed above. Likewise, if treating a microbial/viral infection, the second active ingredient is preferably an anti-biotic and/or an anti-viral agent.

The components of the kit-of-parts are preferably comprised in individual compositions, it is however within the scope of the present invention that the components of the kit-of-parts all are comprised within the same composition. The components of the kit-of-parts may thus be administered simultaneously or sequentially in any order.

Sequence Listing

| SEQ ID NO | Description |
|---|---|
| SEQ ID NO: 1 | Amino acid sequence of TDO of homo sapiens |
| SEQ ID NO: 2 | Polypeptide fragment of human TDO, $TDO_{159-168}$ |
| SEQ ID NO: 3 | Polypeptide fragment of human TDO, $TDO_{200-208}$ |
| SEQ ID NO: 4 | Polypeptide fragment of human TDO, $TDO_{72-81}$ |
| SEQ ID NO: 5 | Polypeptide fragment of human TDO, $TDO_{40-48}$ |
| SEQ ID NO: 6 | Polypeptide fragment of human TDO, $TDO_{123-132}$ |
| SEQ ID NO: 7 | Polypeptide fragment of human TDO, $TDO_{65-74}$ |
| SEQ ID NO: 8 | Polypeptide fragment of human TDO, $TDO_{192-201}$ |
| SEQ ID NO: 9 | Polypeptide fragment of human TDO, $TDO_{309-317}$ |
| SEQ ID NO: 10 | Polypeptide fragment of human TDO, $TDO_{85-93}$ |
| SEQ ID NO: 11 | Polypeptide fragment of human TDO, $TDO_{130-138}$ |
| SEQ ID NO: 12 | Polypeptide fragment of human TDO, $TDO_{276-284}$ |
| SEQ ID NO: 13 | Polypeptide fragment of human TDO, $TDO_{364-372}$ |
| SEQ ID NO: 14 | Polypeptide fragment of human TDO, $TDO_{225-234}$ |
| SEQ ID NO: 15 | Polypeptide fragment of human TDO, $TDO_{372-381}$ |
| SEQ ID NO: 16 | Polypeptide fragment of human TDO, $TDO_{380-389}$ |
| SEQ ID NO: 17 | Polypeptide fragment of human TDO, $TDO_{118-137}$ |
| SEQ ID NO: 18 | Polypeptide fragment of human TDO, $TDO_{303-322}$ |
| SEQ ID NO: 19 | Polypeptide fragment of HIV, $HIVpol_{468-476}$ |
| SEQ ID NO: 20 | Polypeptide fragment of CMV pp65, CMV $pp65_{495-503}$ |

EXAMPLES

The invention is further illustrated by the following examples, which should however not be construed as limiting for the invention.

Example 1

In this example different TDO-derived epitopes that give rise to T cell reactivity are disclosed. Furthermore, spontaneous CD8+ and CD4+ T-cell mediated reactivity against TDO in both healthy donors and cancer patients is described. However, interestingly the phenotype of TDO-specific T cells varied between healthy individuals and patients with a malignant disease.

Materials and Methods

Patients

Peripheral blood mononuclear cells (PBMC) were collected from patients with Melanoma (MM), Breast Cancer (BC) and healthy donors (HD). For cancer patients there was an at least 4 week interval between blood draws and any kind of anticancer therapy. PBMCs were isolated using Lymphoprep separation, HLA-typed (Department of Clinical Immunology, University Hospital, Copenhagen, Denmark), and frozen in fetal calf serum (FCS) (Gibco, Naerum, Denmark) with 10% dimethyl sulfoxide (DMSO) (Sigma-Aldrich, Brøndby, Denmark). Written informed consent from the patients was obtained before any of these measures. The protocol was approved by the scientific ethics committee for the Capital Region of Denmark and conducted in accordance with the provisions of the declaration of Helsinki. HD PBMCs were obtained from the State Hospital blood bank.

Tumor Cell Lines

Cell lines FM-55M1 and FM-86 were provided from EST-DAB, A2058 and MDA-MB 231 were obtained from ATCC, UKE-1(Zeeberg et al., 2013) was a kind gift from W. Fiedler (University Hospital of Eppedorf, Hamburg, Germany). All cell lines were maintained in RPMI 1640 (Gibco) supplied with 10% FBS (Gibco).

Peptides

The TDO amino acid sequence was screened by the use of the publicly available database SYFPEITHI for possible epitopes restricted to HLA-A2. Fifteen peptides were selected, synthesized by TAG Copenhagen (Copenhagen, Denmark). Once lyophilized peptides were dissolved in water or DMSO (Sigma-Aldrich) according to the recommendation of the manufacturer, they were stored at −20° C. in aliquots avoiding freeze-thaw cycles. The peptides were $TDO_{40-48}$(LIYGNYLHL)(SEQ ID NO:5), $TDO_{65-74}$ (KIHDEHLFII)(SEQ ID NO:7), $TDO_{72-81}$ (FIITHQAYEL)(SEQ ID NO:4), $TDO_{85-93}$ (QILWELDSV)(SEQ ID NO:10), $TDO_{123-132}$ (KLLVQQFSIL)(SEQ ID NO: 6), $TDO_{130-138}$ (SILETMTAL)(SEQ ID NO:11), $TDO_{159-168}$ (RLLENKIGVL)(SEQ ID NO:2), $TDO_{192-201}$ (LLKSEQEKTL) (SEQ ID NO:8), $TDO_{200-208}$ (TLLELVEAWL) (SEQ ID NO:3), $TDO_{225-234}$ (KLEKNITRGL)(SEQ ID NO:14), $TDO_{276-284}$ (LLSKGERRL)(SEQ ID NO:12), $TDO_{309-317}$ (QLLTSLMDI)(SEQ ID NO:9), $TDO_{364-372}$ (DLFNLSTYL)(SEQ ID NO:13), $TDO_{372-381}$ (LIPRHWIPKM) (SEQ ID NO:15) and $TDO_{380-389}$ (KMNPTIHKFL)(SEQ ID NO:16). For negative and positive controls, the HIV derived peptide $HIVpol_{468-476}$ (ILKEPVHGV)(SEQ ID NO:19) and the CMV $pp65_{495-503}$ (NLVPMVATV)(SEQ ID NO:20) were used, respectively. Additionally, longer peptides (20 amino acids) comprising $TDO_{123-132}$ and $TDO_{309-317}$, respectively, were synthesized. These were named $TDO_{118-137}$ (VSVILKLLVQQFSILETMTA)(SEQ ID NO:17) and $TDO_{303-322}$ (RFQVPFQLLTSLMDIDSLMT) (SEQ ID NO:18) and both included several potential class II-restricted epitopes as suggested by the predictive algorithm SYFPEITHI.

HLA Peptide Exchange Technology and MHC ELISA

The HLA-peptide affinity was measured by a UV exchange method in combination with a sandwich ELISA as previously described (Toebes et al. 2006). In short, HLA-A2 light and heavy chains were produced in E. Coli and refolded with a UV-sensitive ligand. This conditional ligand was cleaved upon 1 hour of UV light exposure and substituted with the peptide of interest. After adding the HLA-A2-peptide complex to an ELISA, the affinity of the complex was measured as the absorbance. Two peptides with well described high affinity towards HLA-A2 (HIV $pol_{468-476}$ and CMV $pp65_{495-503}$) were used as positive control peptides, while a sample without substitution peptide was used as a negative control. Positive controls were made in quadruplicates and TDO peptides in triplicates.

ELISPOT Assay

In the present study the ELISPOT was performed according to the guidelines provided by CIP. The ELISPOT assay was used to quantify peptide epitope specific effector cells that release cytokines (IFNγ, TNFα,IL-17A or :IL-10) as described previously (Sorensen et al., 2012). In some experiments, PBMCs were stimulated once in vitro with peptide prior to analysis. In some experiments, $10^4$ autologous DCs were added to the wells as antigen presenting cells. The spots were counted using the ImmunoSpot Series 2.0 Analyzer (C.T.L.—Europe, Bonn, Germany). In some experiments, CD4+ cells were isolated by EasySep human CD4+ T cell enrichment kit (Stem Cell technologies, Grenoble, France) following manufacturers' instructions. This yielded highly pure cultures (>97% CD4+), which was confirmed by staining with surface antibodies as described below for intracellular cytokine staining (ICS) and flow cytometry (FCM).

Figure 6A:
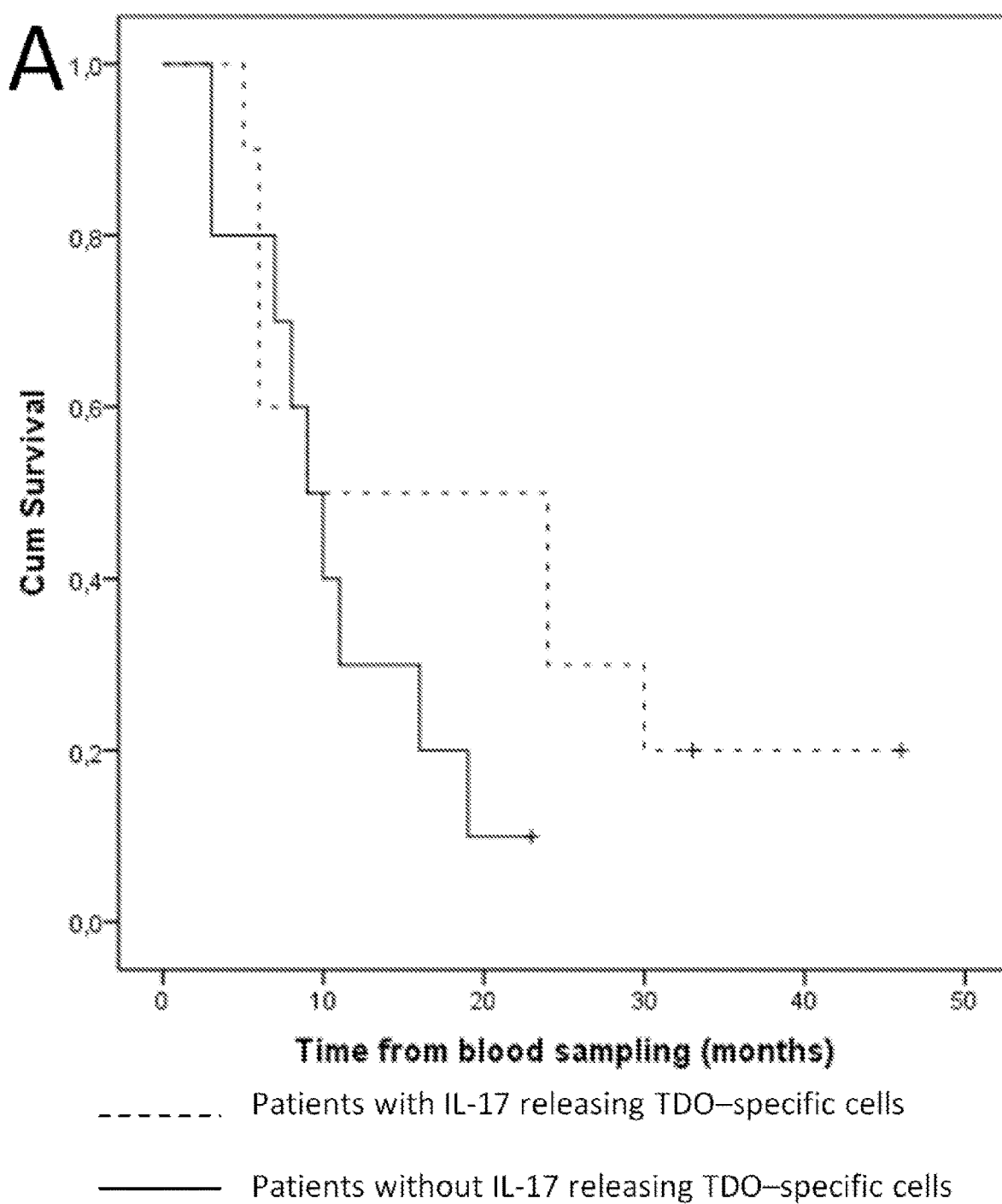
FIG. 6 shows clinical course of the examined melanoma patients. (A), Kaplan Meier estimate of OS defiend as date of blood sample to date of death for melanoma patients with $TDO_{303-322}$-specific IL-17-releasing T cells (dottet line) and for melanoma patients without $TDO_{303-322}$-specific IL-17 T cells (solid line). (B), Kaplan Meier estimate of OS defined as date of blood sample to date of death for melanoma patients with $TDO_{303-322}$-specific IL-10-releasing T cells (dottet line) and for melanoma patients without $TDO_{303-322}$-specific IL-10 T cells (solid line). (C), Kaplan Meier estimate of OS defined as date of blood sample to date of death for melanoma patients with $TDO_{303-322}$-specific IL-17-releasing T cells without IL-10 releasing cells (dottet line) and for melanoma patients with $TDO_{303-322}$-specific IL-10 T cells without IL-17 releasing cells (solid line).
Figure 6B:
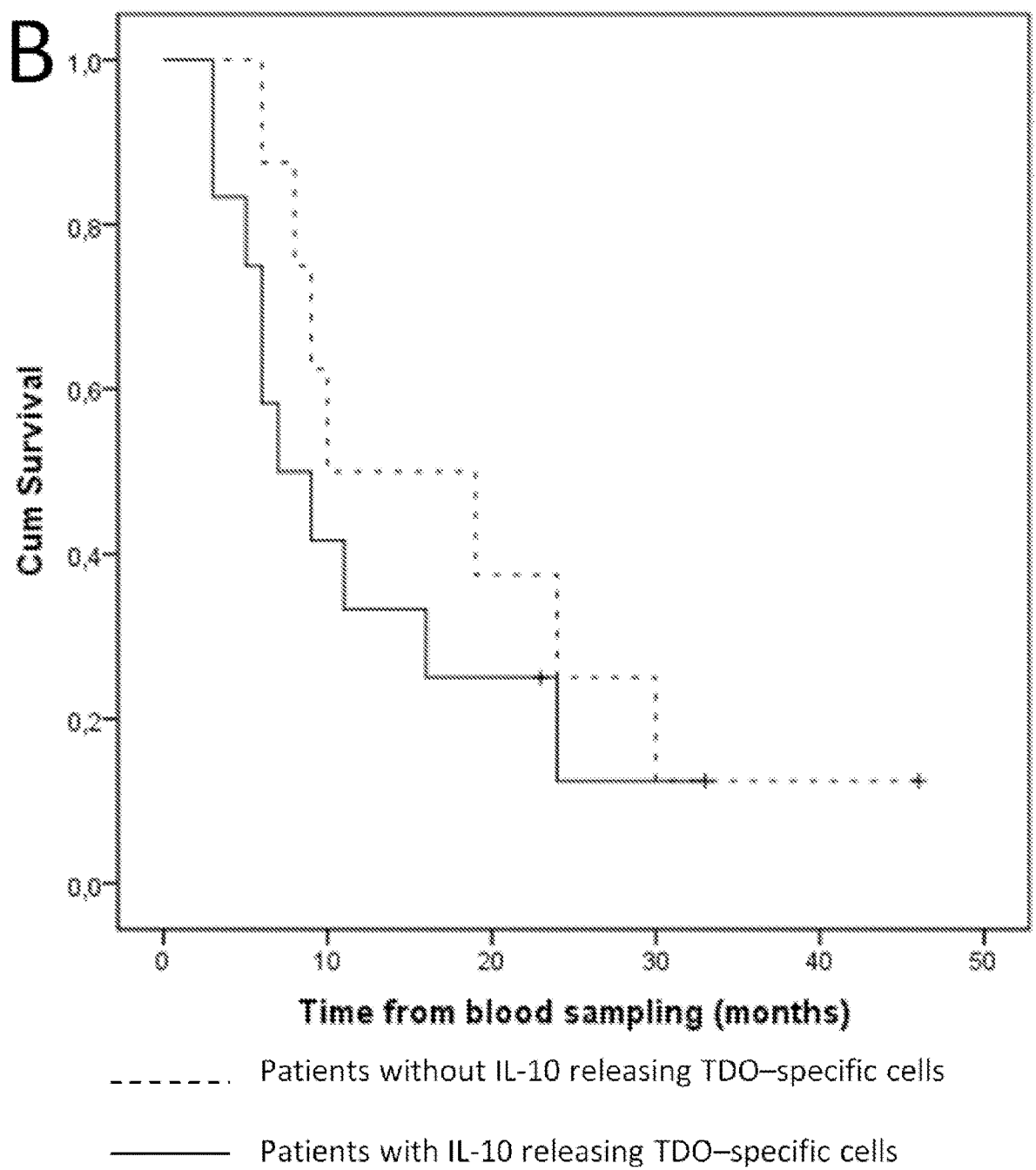
Figure 6C:
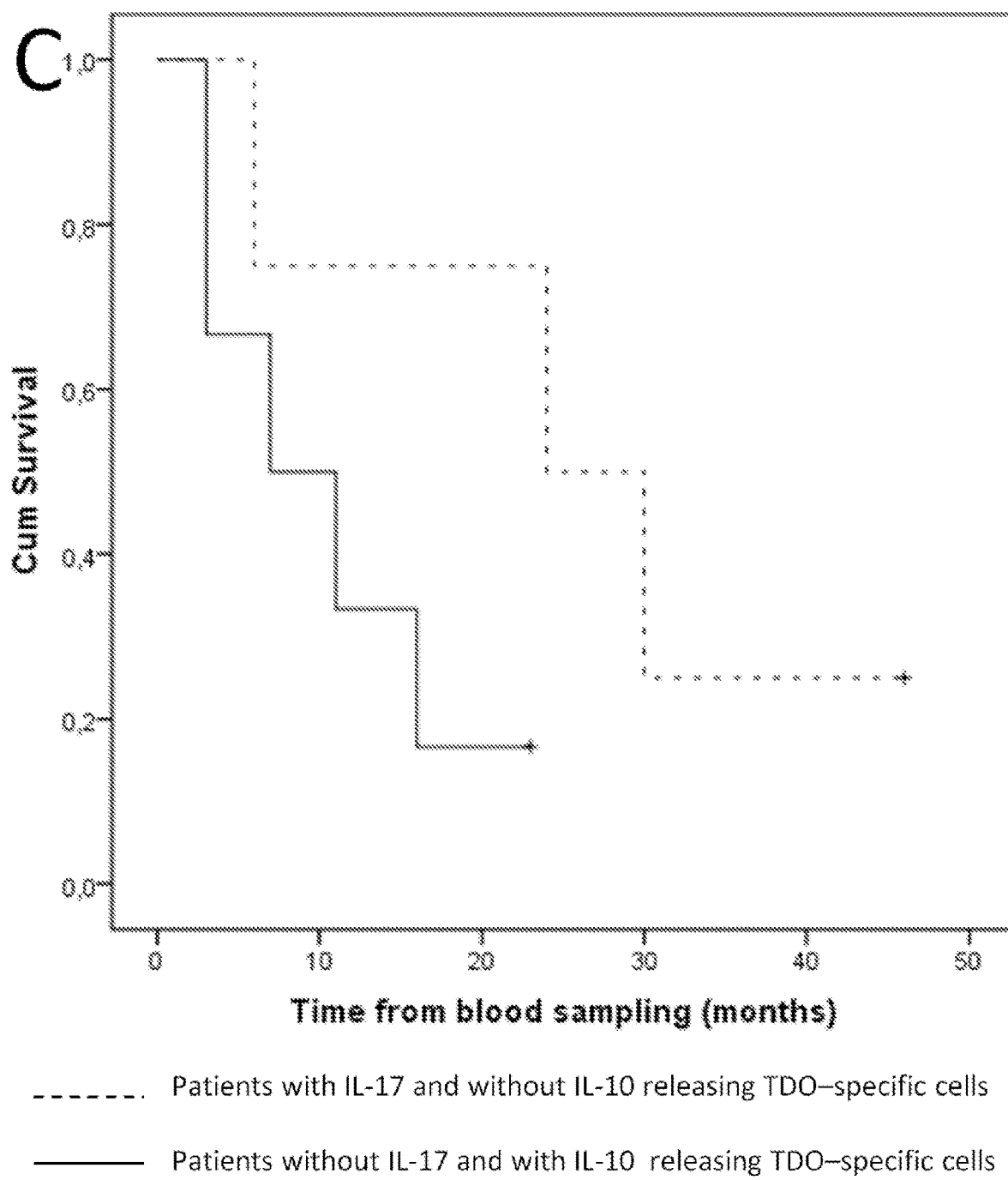
Figure 8:
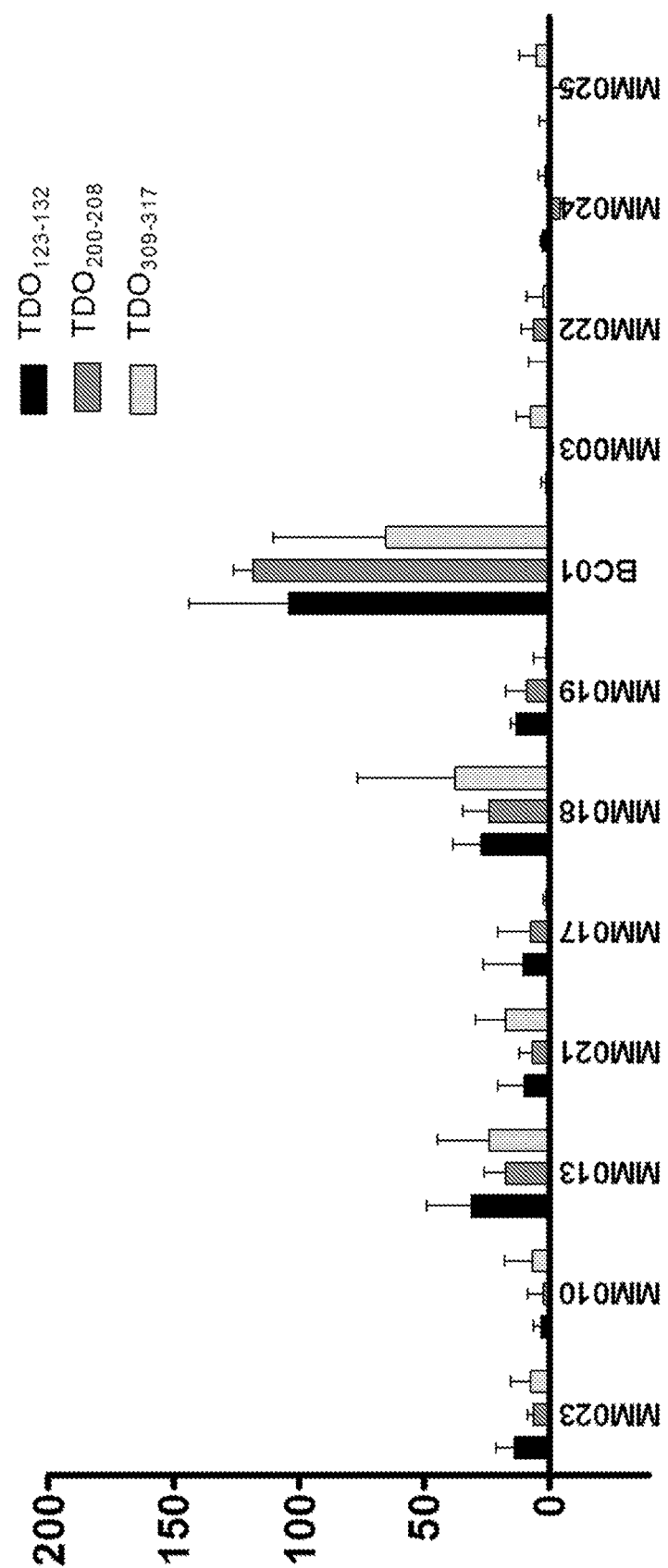
FIG. 8 shows responses towards TDO-derived peptides are detectable directly ex vivo. Ex vivo IFNγ ELISPOT in response to $TDO_{123-132}$ (black), $TDO_{200-208}$ (dark gray) and $TDO_{309-317}$ (light gray) in PBMC from different cancer patients. All experiments were performed in triplicates. The cell numbers were $9*10^5$ cells/well.

Definition of an ELISPOT response was either an empirical or statistical approach. The empirical approach is based on the "signal-to-noise" ratio and suggests that the threshold for response definition should be defined as >6 specific spots per $10^5$ PBMCs. In the FIG. 6 we have increased this to >40 specific spots per $5 \times 10^5$ PBMCs. The non-parametric distribution free resampling (DFR) method allows statistical comparison of antigen-stimulated wells and negative control wells as exemplified in FIG. 8. The release of a given cytokine in response to $TDO_{118-137}$ or $TDO_{303-322}$ was compared between patient and healthy donor groups by a Mann-Whitney test. P-values <0,05 were considered significant.

Generation of TDO Specific T Cell Lines

DC were generated by adherence of PBMCs to the plastic surface of a well for one hour in RPMI 1640 (Gibco) before removal of non-adherent cells. The adherent cells were treated with 1000 U/ml GM-CSF (PeproTech, London, UK) and 250 U/ml IL-4 (Peprotech) in X-vivo 15 (Lonza, Copenhagen, Denmark) supplied with 5% human AB serum (Sigma-Aldrich) and placed in a 37° C., 5% $CO_2$ and humidified environment. On day six, maturation cocktail consisting of 1000 U/ml of each TNFα, IL-1β and IL-6 and 1 μg/ml PGE2 (Peprotech) was added to the cells. On day eight, mature DCs were harvested, loaded with 100 μM TDO peptide in X-vivo 15 (Lonza) for four hours in the incubator. After washing, peptide-loaded DCs were mixed with autologous PBLs in X-vivo 15 (Lonza) supplied with 5% human AB serum (Sigma-Aldrich). The next day, IL-12 and IL-7 (Peprotech) were added to final concentrations of 20 and 40 U/ml, respectively. Cultures were stimulated this way twice seven days apart. Further stimulations were performed using autologous, irradiated (25 Gy) PBLs loaded with 100 μM TDO peptide. The day after stimulation with PBLs the cultures were supplied with IL-2 (Proleukin; Novartis, Copenhagen, Denmark) to a final concentration of 40 U/ml.

FCM and Cell Sorting

Peptide loaded MHC tetramers were e ( ) were stained with 2,5 μl of each phycoerytrhin (PE). No more than $2 \times 10^6$ T cells were stained and allophycocyanin (APC) conjugated tetramers loaded with either a TDO peptide or the $HIVpol_{468-476}$ peptide as a negative control were used. The stainings were performed in 50 μl PBS (Lonza) supplied with 2% FCS (Gibco) for 15 minutes in the incubator. Then an antibody mix consisting of αCD3-AmCyan, αCD4-Fitc (BD Bioscience, Albertslund, Denmark), aCD8-Pacific Blue (DAKO, Glostrup, Denmark) and the near IR Dead Cell Stain Kit (Life technologies, Naerum, Denmark) was added directly and the cells placed at 4° C. in the dark for 30 minutes. After washing in PBS (Lonza) supplied with 2% FCS (Gibco), tetramer positive CD8+ cells were sorted by FACS Aria (BD Biosciences). TDO-specific CD4+ T cells were stimulated with 5 μM $TDO_{303-322}$ in X-vivo 15 medium (Lonza) and IFNy secreting cells were detected using MACS IFNy secretion assay-detection kit (PE) (Miltenyi Biotec, Lund, Sweden). PE positive cells were subsequently sorted into $10^4$ autologous, irradiated (30 Gy) PBMC by a FACS Aria (BD Biosciences).

Rapid Expansion Protocol (REP)

The rapid expansion of sorted specific T cells was performed as follows: Cells were rested in X-vivo 15 (Lonza) supplemented with 5% human serum (Sigma-Aldrich) and 6000 U/ml IL-2 (proleukin; Novartis) over night at 5% CO2 at 37° C. The next day, feeder cells were prepared: a total of $20*10^6$ PBLs from three healthy donors were irradiated (25 Gy), washed and mixed in a ratio of 1:1:1 in 2 ml X-vivo 15 (Lonza) containing 5% human serum (Sigma-Aldrich). After two hours, sample cells were mixed with the feeder cells and IL-2 (Novartis) was added to a final concentration of 6000 U/ml along with αCD3 ab OKT3 (ebioscience, Frankfurt, Germany) to a final concentration of 30 ng/ml in 20 ml medium. Every 3-4 days, cell numbers were adjusted to a maximum of $5*10^5$ cells/ml and fresh IL-2 (Novartis) was added to 6000 U/ml.

Intracellular Cytokine Staining (ICS)

PBMCs were stimulated with 5 μM relevant peptide or control peptide in the presence of GolgiPlug (diluted 1:1000, BD Biosciences) for five hours in the incubator. Then, cells were washed twice in PBS (Lonza) supplied with 2% FCS (Gibco) and stained with surface antibodies as described for cell sorting. After washing of cells in PBS (Lonza) with of 2% FCS (Gibco), cells were fixed and permeabilized with fixation/permebilization buffer (ebioscience) for at least 30 minutes, washed twice and then stained with antibodies specific for IFNy-PE (BD Biosciences) and TNFα-APC (ebioscience). At least 50.000 CD4+ T cells were recorded on a FACS Canto II flow cytometer and data were analyzed with the Diva software package (BD Biosciences).

Cytotoxicity Assay

Assessment of the cytotoxic capability of the generated T-cell lines was evaluated using a conventional chromium release assay as described. Briefly, target tumor cell lines were labeled with 100 μCi $^{51}Cr$ (Perkin Elmer, Skovlunde, Denmark) in 100 μl RPMI 1640 (Gibco) supplied with 10% FCS (Gibco) for one hour at 37° C. After washing of target cells, they were incubated with effector cells at different effector:target (E:T) ratios for four hours in the incubator. Subsequently, the amount of radioactivity in the supernatant was measured using a gamma cell counter (Perkin Elmer Wallac Wizard 1470 Automatic gamma counter).

Results

Presence of TDO-reactive CD8+ T Cell in Peripheral Blood of Healthy Donors and Cancer Patients Potential HLA-A2-restricted T-cell epitopes derived from the TDO amino acid sequence were identified based on the well-defined H LA-binding motif (Rammensee et al., 1999). The fifteen 9- to 10-mer peptides with the highest predicted binding affinity were synthesized and subsequently used to screen PBMC from six cancer patients for the presence of spontaneous T-cell responses by means of the ELISPOT assay. This analysis revealed the presence of IFNγ producing T-cell in response to the peptides $TDO_{123-132}$(KLLVQQF-SIL)(SEQ ID NO:6), $TDO_{200-208}$, (TLLELVEAWL)(SEQ ID NO:3), $TDO_{309-317}$(QLLTSLMDI)(SEQ ID NO:9), and $TDO_{364-372}$ (DLFNLSTYL)(SEQ ID NO:13) after one round of in vitro stimulation (see FIG. 1A). Notably, for several of these peptides T-cell responses were detected in more than one patient. Prompted by these encouraging observations, we used four TDO-derived HLA-A2-restricted T-cell epitopes to analyze PBMCs obtained from 14 additional cancer patients as well as PBMCs from 14 healthy donors for the presence of TDO-reactive T cells; again analyses were performed after one round of in vitro stimulation. As depicted in FIG. 1, T-cell responses were detected against all four peptides both in cancer patients as well as in healthy donors. Surprisingly, the magnitude and frequency of responses were similar in both groups. The non-parametric distribution free resampling (DFR) method allows statistical comparison of antigen-stimulated wells and negative control. Examples of significant responses are given in supplementary FIG. 1. Moreover, TDO-reactive T cells were detected directly ex vivo (see FIG. 8).

Generation and Functional Characterization of TDO-specific CD8+ T-cell Lines

The detection and characterization of specific CD8+ T cells was revolutionized by the introduction of soluble peptide/MHC complexes (Rammensee et al., 1999). To establish TDO-specific CD8+ T cell lines, we repeatedly stimulated PBMCs from a cancer patient with autologous dendritic cells loaded with the TDO peptides $TDO_{123-132}$ or $TDO_{309-317}$ 5- or 4-times respectively. These in vitro stimulations dramatically increased the frequency of TDO-specific CD8+ T cells as measured by two color tetramer staining (see FIG. 2). For further expansion by means of the rapid expansion protocol (REP) $TDO_{123-132}$ and $TDO_{309-317}$ reactive T cells were enriched by fluorescence-activated cell sorting. After applying REP the specificity of the resulting T-cell lines was confirmed by tetramer staining demonstrating 97.1% and 99.6% purity (see FIG. 2). These T-cell lines were tested for their capabilities to lyse either TAP-deficient peptide-pulsed T2 cells or H LA-matched TDO-expressing tumor cells. As depicted in FIG. 3A and B, TDO-specific T-cell cultures effectively lysed T2 cells when these had been pulsed with the same TDO peptide used for expansion, but not T2 cells pulsed with an irrelevant different TDO-derived peptide. Most important, TDO-specific T cells efficiently lysed HLA-A2+ cancer cell lines of different tissue origin, but not HLA-A2− cancer cells (see FIGS. 3C and D). The lysis of TDO-expressing cancer cell lines was not uniform. Specifically, the breast cancer cell line MDA-MB 231 was killed by both $TDO_{123-132}$ and $TDO_{309-317}$ specific T-cell lines; the latter T-cell line demonstrating more efficient killing. On the other hand, the HLA-A2+ leukemia cell line UKE-1 was very effectively lysed by $TDO_{123-132}$ specific T cells, but only scarcely by $TDO_{309-317}$ specific T cells. $TDO_{123-132}$ specific T cells did not lyse HLA-A2+ melanoma cell lines FM-55M1 and FM-86, which were efficiently lysed by $TDO_{309-317}$ specific T cells. Finally, the HLA-A2−TDO+ melanoma cell line A2058 was not lysed by either T-cell line.

TDO Dependent Recognition of Immune Cells

To test whether TDO-specific T cells were able to recognize autologous, mature DC transfected with TDO mRNA, autologous DC, transfected them with TDO mRNA were generated before analysis in ELISPOT. This experiment revealed that $TDO_{309-317}$-specific T-cells specifically recognized DC transfected with TDO (see FIG. 4A). It has previously been shown that the TAP-deficient cell line T2 very efficiently process and present long peptides on the surface on HLA-A2. Two 20 amino acid peptides were synthesized, which included two of the minimal epitopes ($TDO_{123-132}$ (KLLVQQFSIL)(SEQ ID NO:6) and $TDO_{309-317}$(QLLTSLMDI)(SEQ ID NO:9). $TDO_{118-137}$ (VSV ILK LLV QQF SIL ETM TA)(SEQ ID NO:17) includes the epitope $TDO_{123-132}$ and $TDO_{303-322}$ (RFQ VPF QLL TSL MDI DSL MT)(SEQ ID NO:18) includes the epitope $TDO_{309-317}$. It was then analyzed if T2 cells could cross-present the two long peptides. In this regard, T2-cells were loaded overnight with either $TDO_{118-137}$ or $TDO_{303-322}$ before they were used in a standard cytotoxicity assay. As demonstrated in FIG. 4B lysis of T2 cells was observed both when loaded with the short peptide and the corresponding long peptide, i.e. $TDO_{123-132}$ specific cells lysed T2 cells pulsed with $TDO_{123-132}$ peptide or $TDO_{118-137}$ but not when pulsed either $TDO_{309-317}$ or $TDO_{303-322}$. Hence, the long TDO-derived peptides are taken up and cross presented in context of HLA-A2 in T2 cells.

CD4+ T Cells Recognize TDO

To further scrutinize the immunogenicity of TDO we utilized the two long peptides $TDO_{118-137}$ and $TDO_{303-322}$ in ELISPOT assays for IFNγ, TNFα, IL-10, and IL-17A (results are shown in FIG. 5). Peptide-specific CD4 T-cell responses were present in both cancer patients and healthy donors. Wth respect to IFNy producing CD4+ T cells there was no difference between the 2 cohorts. However, cells producing TNFα in response to long TDO peptides were more frequent in healthy donors; for $TDO_{118-137}$ this difference was highly significant (p<0.0001). IL-10 and IL-17 production in response to peptide stimulation was restricted to cancer patients. For $TDO_{303-322}$ these differences were statistically significant (p=0.0051 and p<0.0001, respectively). IL-17 and IL-10, which were only released in response to long TDO peptides by PBMCs obtained from cancer patients, exert profound immune modulating functions and have been implicated with the clinical course of cancer patients. The frequency of CD4+ T cells producing IL-17A and IL-10 in response to the long $TDO_{303-322}$ peptides with the clinical course were correlated, which revealed a clear impact of the presence of IL-17 and IL-10 producing cells on the overall survival (OS): Patients characterized by CD4+ cells releasing IL-17A had a trend towards an improved OS compared to the non-IL-17A responders (see FIG. 6A); whereas patients with IL-10 releasing CD4+ T cell in response to the TDO peptides have an impaired OS (see FIG. 6B). These OS difference was even more pronounced when patients harboring either IL-17+/IL-10- or IL-17−/IL-10+ producing T cells were compared. Patients with the presence of cells producing 17+/IL-10-in response to $TDO_{303-322}$ peptides had a much better survival (see FIG. 6C).

The present invention discloses that TDO is a target for natural T-cell responses, which were readily detectable both in cancer patients as well as in healthy donors. Notably, TDO-specific CD4 and CD8 T-cell responses were present in health and disease in the same frequency. Thus, healthy donors apparently harbor strong immune responses against the self-protein TDO. Interestingly, however, TDO-specific CD4+ T cells differed in their functional characteristics in health and cancer. In healthy donors TDO-specific CD4+ T cells released TNFα and IFNγ, but not the regulatory cytokines IL-17 or IL-10. In fact, TDO-specific CD4+ T cells producing TNFα were significantly more frequent in healthy donors as compared to cancer patients. This indicates that TDO does not necessarily induce tolerance in healthy individuals.

CD8+ and CD4+ T cells may exert immune regulatory functions by release of cytokines—or even by cytolysis—in response to epitopes derived from the immunosuppressive molecule TDO. Hence, both TDO-specific CD8+ and CD4+ T cells may play a role in the fine-tuning of the immune response by suppression of the immune permissive state induced by TDO-expressing cells. In cancer patients, however, the phenotype of the CD4+ TDO-reactive T cells was more complex: In addition to IFNγ and TNFα the cells also produced IL-17 and IL-10 in response to TDO epitopes. Production of IL-17 defines a subset of CD4+ T-helper cells (Th17 cells) involved in many pathologic situations including autoimmunity and cancer. Notably, Th17 cells have been attributed a protective role against cancer by promoting antitumor immunity. Tumor-infiltrating Th17 cells express other cytokines in addition to IL-17 such as IFNγ, IL-2, and TNF. Notably, some TDO-specific Th17 cells exhibit a similar effector T-cell cytokine profile. Moreover, cancer patients hosting a TDO-specific IL-17 response showed a trend towards an improved OS.

On the other hand, in cancer patients the release of IL-10 in response to the TDO epitopes was observed. IL-10 is an immunosuppressive cytokine, which is produced among other cells by Tregs. Tregs are important to maintain immune homeostasis and to insure tolerance to self-antigens. Thus, TDO-specific Tregs might enhance the TDO-mediated immune suppression and thereby boost cancer cells immune escape. Accordingly, patients with IL-10 producing, TDO-reactive CD4+ T cells showed a trend towards an impaired OS. The OS difference of patients harboring IL-17+/IL-10− or IL-17−/IL-10+ producing T cells in response to TDO peptides was pronounced Functional characterization of in vitro expanded CD8+ TDO-reactive T cells revealed that these killed HLA-matched tumor cells of different origin.

REFERENCES

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A. Cancer regression in patients after transfer of genetically engineered lymphocytes. Science. 2006 Oct. 6; 314(5796): 126-9. Epub 2006 Aug. 31.

Nicolette CA, Healey D, Tcherepanova I, Whelton P, Monesmith T, Coombs L, Finke L H, Whiteside T, Miesowicz F, (2007). Dendritic cells for active immunotherapy: optimizing design and manufacture in order to develop commercially and clinically viable products. Vaccine, September 27; 25 Suppl 2:B47-60. Epub 2007

Pilotte L, Larrieu P, Stroobant V, Colau D, Dolusic E, Frédérick R, et al. Reversal of tumoral immune resistance by inhibition of tryptophan 2,3-dioxygenase. Proc Natl Acad Sci U S A [Internet]. 2012 [cited 2013 Apr. 6]; 109:2497-502

Rammensee H, Bachmann J, Emmerich N P, Bachor O a, StevanovićS. SYFPEITHI: database for MHC ligands and peptide motifs. Immunogenetics [Internet]. 1999; 50:213-9.

Sørensen R B, Berge-Hansen L, Junker N, Hansen C A, Hadrup S R, Schumacher T N M, et al. The immune system strikes back: cellular immune responses against indoleamine 2,3-dioxygenase. PLoS One [Internet]. 2009 [cited 2012 Aug. 15]; 4:e6910

Toebes M, Coccoris M, Bins A, Rodenko B, Gomez R, Nieuwkoop N J, et al. Design and use of conditional MHC class I ligands. Nat Med. 2006; 12:246

Walter E A, Greenberg P D, Gilbert M J, Finch R J, Watanabe K S, Thomas E D, Riddell S R (1995). Reconstitution of cellular immunity against cytomegalovirus in recipients of allogeneic bone marrow by transfer of T-cell clones from the donor. N Engl J Med. 1995 Oct. 19; 333(16):1038-44

Zeeberg Iversen T, Engell-Noerregaard L, Ellebaek E, Andersen R, Kiaer Larsen S, Bjoern J, et al. Long-lasting disease stabilization in the absence of toxicity in metastatic lung cancer patients vaccinated with an epitope derived from indoleamine 2,3 dioxygenase. Clin cancer Res [Internet]. 2013 [cited 2013 Nov. 14]

The invention claimed is:

1. A vaccine composition comprising an immunogenically active peptide fragment consisting of at the most 40 consecutive amino acids of tryptophan 2,3-dioxygenase (TDO) of SEQ ID NO:1, wherein the immunogenically active peptide fragment comprises a polypeptide selected from the group consisting of:
   a) SEQ ID NO: 3 (TDO$_{200-208}$);
   b) SEQ ID NO: 6 (TDO$_{123-132}$);
   c) SEQ ID NO: 9 (TDO$_{309-317}$);
   d) SEQ ID NO: 13 (TDO$_{364-372}$);
   e) SEQ ID NO: 17 (TDO$_{118-137}$); and
   f) SEQ ID NO: 18 (TDO$_{303-322}$); and
   an effective amount of an adjuvant or preservative.

2. The vaccine composition according to claim 1, wherein the peptide fragment consists of at the most 30 amino acid residues.

3. The vaccine composition according to claim 1, wherein the peptide fragment consists of a sequence selected from the group of SEQ ID NO: 3, SEQ ID NO: 6, SEQ ID NO: 9, SEQ ID NO: 13, SEQ ID NO: 17, or SEQ ID NO: 18.

4. The vaccine composition according to claim 1, wherein said polypeptide is a polypeptide of at the most 20 amino acids comprising a consecutive sequence of amino acids of SEQ ID NO:1.

5. The vaccine composition according to claim 1, wherein the vaccine composition further comprises antigen presenting cells comprising the immunogenically active peptide fragment or a nucleic acid encoding said immunogenically active peptide fragment.

6. A vaccine composition according to claim 1, further comprising an immunogenically active protein or peptide fragment selected from a protein or peptide fragment, which is not TDO.

7. A vaccine composition according to claim 1, wherein the adjuvant is selected from the group consisting of bacterial DNA based adjuvants, oil/surfactant based adjuvants, viral dsRNA based adjuvants and imidazochinilines.

8. A vaccine composition according to claim 1, wherein the adjuvant is GM-SF or a Montanide ISA adjuvant, optionally wherein the Montanide ISA adjuvant is Montanide ISA 51 or Montanide ISA 720, optionally wherein the Montanide ISA adjuvant is Montanide ISA 51.

9. An immunogenically active peptide fragment consisting of at the most 40 consecutive amino acids of TDO of SEQ ID NO:1, wherein the immunogenically active peptide fragment comprises a polypeptide selected from the group consisting of:
 a) SEQ ID NO: 3 ($TDO_{200-208}$);
 b) SEQ ID NO: 6 ($TDO_{123-132}$);
 c) SEQ ID NO: 9 ($TDO_{309-317}$);
 d) SEQ ID NO: 13 ($TDO_{364-372}$);
 e) SEQ ID NO: 17 ($TDO_{118-137}$); and
 f) SEQ ID NO: 18 ($TDO_{303-322}$).

10. An immunogenically active peptide fragment according to claim 9 which consists of a sequence selected from the group of SEQ ID NO: 3, SEQ ID NO: 6, SEQ ID NO: 9, SEQ ID NO: 13, SEQ ID NO: 17, and SEQ ID NO: 18.

11. A method of treating cancer characterized by the expression of TDO, the method comprising administering to an individual suffering from cancer an effective amount of the composition of claim 1.

12. The method of to claim 11, which is combined with a further cancer treatment.

13. The method according to claim 11, wherein the immunogenically active peptide fragment of TDO from the composition of claim 1 is administered at a dose in the range of 50 µg to 500 µg, for example in the range of 80 µg to 300 µg, such as in the range of 100 µg to 250 µg per individual, wherein the individual preferably is a human being.

* * * * *

SEQUENCE LISTING

```
<160> NUMBER OF SEQ ID NOS: 20

<210> SEQ ID NO 1
<211> LENGTH: 406
<212> TYPE: PRT
<213> ORGANISM: homo sapiens

<400> SEQUENCE: 1

Met Ser Gly Cys Pro Phe Leu Gly Asn Asn Phe Gly Tyr Thr Phe Lys
1               5                   10                  15

Lys Leu Pro Val Glu Gly Ser Glu Asp Lys Ser Gln Thr Gly Val
            20                  25                  30

Asn Arg Ala Ser Lys Gly Gly Leu Ile Tyr Gly Asn Tyr Leu His Leu
        35                  40                  45

Glu Lys Val Leu Asn Ala Gln Glu Leu Gln Ser Glu Thr Lys Gly Asn
    50                  55                  60

Lys Ile His Asp Glu His Leu Phe Ile Ile Thr His Gln Ala Tyr Glu
65                  70                  75                  80

Leu Trp Phe Lys Gln Ile Leu Trp Glu Leu Asp Ser Val Arg Glu Ile
                85                  90                  95

Phe Gln Asn Gly His Val Arg Asp Glu Arg Asn Met Leu Lys Val Val
            100                 105                 110

Ser Arg Met His Arg Val Ser Val Ile Leu Lys Leu Leu Val Gln Gln
        115                 120                 125

Phe Ser Ile Leu Glu Thr Met Thr Ala Leu Asp Phe Asn Asp Phe Arg
    130                 135                 140
```

```
Glu Tyr Leu Ser Pro Ala Ser Gly Phe Gln Ser Leu Gln Phe Arg Leu
145                 150                 155                 160

Leu Glu Asn Lys Ile Gly Val Leu Gln Asn Met Arg Val Pro Tyr Asn
            165                 170                 175

Arg Arg His Tyr Arg Asp Asn Phe Lys Gly Glu Glu Asn Glu Leu Leu
        180                 185                 190

Leu Lys Ser Glu Gln Glu Lys Thr Leu Leu Glu Leu Val Glu Ala Trp
    195                 200                 205

Leu Glu Arg Thr Pro Gly Leu Glu Pro His Gly Phe Asn Phe Trp Gly
210                 215                 220

Lys Leu Glu Lys Asn Ile Thr Arg Gly Leu Glu Glu Phe Ile Arg
225                 230                 235                 240

Ile Gln Ala Lys Glu Glu Ser Glu Glu Lys Glu Gln Val Ala Glu
                245                 250                 255

Phe Gln Lys Gln Lys Glu Val Leu Leu Ser Leu Phe Asp Glu Lys Arg
            260                 265                 270

His Glu His Leu Leu Ser Lys Gly Glu Arg Arg Leu Ser Tyr Arg Ala
        275                 280                 285

Leu Gln Gly Ala Leu Met Ile Tyr Phe Tyr Arg Glu Glu Pro Arg Phe
290                 295                 300

Gln Val Pro Phe Gln Leu Leu Thr Ser Leu Met Asp Ile Asp Ser Leu
305                 310                 315                 320

Met Thr Lys Trp Arg Tyr Asn His Val Cys Met Val His Arg Met Leu
                325                 330                 335

Gly Ser Lys Ala Gly Thr Gly Gly Ser Ser Gly Tyr His Tyr Leu Arg
            340                 345                 350

Ser Thr Val Ser Asp Arg Tyr Lys Val Phe Val Asp Leu Phe Asn Leu
        355                 360                 365

Ser Thr Tyr Leu Ile Pro Arg His Trp Ile Pro Lys Met Asn Pro Thr
    370                 375                 380

Ile His Lys Phe Leu Tyr Thr Ala Glu Tyr Cys Asp Ser Ser Tyr Phe
385                 390                 395                 400

Ser Ser Asp Glu Ser Asp
                405

<210> SEQ ID NO 2
<211> LENGTH: 10
<212> TYPE: PRT
<213> ORGANISM: artificial sequence
<220> FEATURE:
<223> OTHER INFORMATION: Peptide fragment of human TDO

<400> SEQUENCE: 2

Arg Leu Leu Glu Asn Lys Ile Gly Val Leu
1               5                   10

<210> SEQ ID NO 3
<211> LENGTH: 10
<212> TYPE: PRT
<213> ORGANISM: artificial sequence
<220> FEATURE:
<223> OTHER INFORMATION: Peptide fragment of human TDO

<400> SEQUENCE: 3

Thr Leu Leu Glu Leu Val Glu Ala Trp Leu
1               5                   10

<210> SEQ ID NO 4
```

```
<211> LENGTH: 10
<212> TYPE: PRT
<213> ORGANISM: artificial sequence
<220> FEATURE:
<223> OTHER INFORMATION: Peptide fragment of human TDO

<400> SEQUENCE: 4

Phe Ile Ile Thr His Gln Ala Tyr Glu Leu
 1               5                  10

<210> SEQ ID NO 5
<211> LENGTH: 9
<212> TYPE: PRT
<213> ORGANISM: artificial sequence
<220> FEATURE:
<223> OTHER INFORMATION: Peptide fragment of human TDO

<400> SEQUENCE: 5

Leu Ile Tyr Gly Asn Tyr Leu His Leu
 1               5

<210> SEQ ID NO 6
<211> LENGTH: 10
<212> TYPE: PRT
<213> ORGANISM: artificial sequence
<220> FEATURE:
<223> OTHER INFORMATION: Peptide fragment of human TDO

<400> SEQUENCE: 6

Lys Leu Leu Val Gln Gln Phe Ser Ile Leu
 1               5                  10

<210> SEQ ID NO 7
<211> LENGTH: 10
<212> TYPE: PRT
<213> ORGANISM: artificial sequence
<220> FEATURE:
<223> OTHER INFORMATION: Peptide fragment of human TDO

<400> SEQUENCE: 7

Lys Ile His Asp Glu His Leu Phe Ile Ile
 1               5                  10

<210> SEQ ID NO 8
<211> LENGTH: 10
<212> TYPE: PRT
<213> ORGANISM: artificial sequence
<220> FEATURE:
<223> OTHER INFORMATION: Peptide fragment of human TDO

<400> SEQUENCE: 8

Leu Leu Lys Ser Glu Gln Glu Lys Thr Leu
 1               5                  10

<210> SEQ ID NO 9
<211> LENGTH: 9
<212> TYPE: PRT
<213> ORGANISM: artificial sequence
<220> FEATURE:
<223> OTHER INFORMATION: Peptide fragment of human TDO

<400> SEQUENCE: 9

Gln Leu Leu Thr Ser Leu Met Asp Ile
 1               5

<210> SEQ ID NO 10
<211> LENGTH: 9
```

<212> TYPE: PRT
<213> ORGANISM: artificial sequence
<220> FEATURE:
<223> OTHER INFORMATION: Peptide fragment of human TDO

<400> SEQUENCE: 10

Gln Ile Leu Trp Glu Leu Asp Ser Val
1               5

<210> SEQ ID NO 11
<211> LENGTH: 9
<212> TYPE: PRT
<213> ORGANISM: artificial sequence
<220> FEATURE:
<223> OTHER INFORMATION: Peptide fragment of human TDO

<400> SEQUENCE: 11

Ser Ile Leu Glu Thr Met Thr Ala Leu
1               5

<210> SEQ ID NO 12
<211> LENGTH: 9
<212> TYPE: PRT
<213> ORGANISM: artificial sequence
<220> FEATURE:
<223> OTHER INFORMATION: Peptide fragment of human TDO

<400> SEQUENCE: 12

Leu Leu Ser Lys Gly Glu Arg Arg Leu
1               5

<210> SEQ ID NO 13
<211> LENGTH: 9
<212> TYPE: PRT
<213> ORGANISM: artificial sequence
<220> FEATURE:
<223> OTHER INFORMATION: Peptide fragment of human TDO

<400> SEQUENCE: 13

Asp Leu Phe Asn Leu Ser Thr Tyr Leu
1               5

<210> SEQ ID NO 14
<211> LENGTH: 10
<212> TYPE: PRT
<213> ORGANISM: artificial sequence
<220> FEATURE:
<223> OTHER INFORMATION: Peptide fragment of human TDO

<400> SEQUENCE: 14

Lys Leu Glu Lys Asn Ile Thr Arg Gly Leu
1               5                   10

<210> SEQ ID NO 15
<211> LENGTH: 10
<212> TYPE: PRT
<213> ORGANISM: artificial sequence
<220> FEATURE:
<223> OTHER INFORMATION: Peptide fragment of human TDO

<400> SEQUENCE: 15

Leu Ile Pro Arg His Trp Ile Pro Lys Met
1               5                   10

<210> SEQ ID NO 16
<211> LENGTH: 10
<212> TYPE: PRT

```
<213> ORGANISM: artificial sequence
<220> FEATURE:
<223> OTHER INFORMATION: Peptide fragment of human TDO

<400> SEQUENCE: 16

Lys Met Asn Pro Thr Ile His Lys Phe Leu
1               5                   10

<210> SEQ ID NO 17
<211> LENGTH: 20
<212> TYPE: PRT
<213> ORGANISM: artificial sequence
<220> FEATURE:
<223> OTHER INFORMATION: Peptide fragment of human TDO

<400> SEQUENCE: 17

Val Ser Val Ile Leu Lys Leu Leu Val Gln Gln Phe Ser Ile Leu Glu
1               5                   10                  15

Thr Met Thr Ala
            20

<210> SEQ ID NO 18
<211> LENGTH: 20
<212> TYPE: PRT
<213> ORGANISM: artificial sequence
<220> FEATURE:
<223> OTHER INFORMATION: Peptide fragment of human TDO

<400> SEQUENCE: 18

Arg Phe Gln Val Pro Phe Gln Leu Leu Thr Ser Leu Met Asp Ile Asp
1               5                   10                  15

Ser Leu Met Thr
            20

<210> SEQ ID NO 19
<211> LENGTH: 9
<212> TYPE: PRT
<213> ORGANISM: artificial sequence
<220> FEATURE:
<223> OTHER INFORMATION: Peptide fragment of HIVpol

<400> SEQUENCE: 19

Ile Leu Lys Glu Pro Val His Gly Val
1               5

<210> SEQ ID NO 20
<211> LENGTH: 9
<212> TYPE: PRT
<213> ORGANISM: artificial sequence
<220> FEATURE:
<223> OTHER INFORMATION: Peptide fragment of CMV pp65

<400> SEQUENCE: 20

Asn Leu Val Pro Met Val Ala Thr Val
1               5
```